US008669074B2

(12) United States Patent
Violin et al.

(10) Patent No.: US 8,669,074 B2
(45) Date of Patent: Mar. 11, 2014

(54) CHIMERIC PHOSPHORYLATION INDICATOR

(75) Inventors: Jonathan D. Violin, Durham, NC (US); Alexandra C. Newton, San Diego, CA (US); Roger Y. Tsien, La Jolla, CA (US); Jin Zhang, Baltimore, MD (US)

(73) Assignee: The Regents of the University of California, Oakland, CA (US)

( * ) Notice: Subject to any disclaimer, the term of this patent is extended or adjusted under 35 U.S.C. 154(b) by 2722 days.

(21) Appl. No.: 10/857,622

(22) Filed: May 28, 2004

(65) Prior Publication Data

US 2005/0026234 A1 Feb. 3, 2005

Related U.S. Application Data

(63) Continuation-in-part of application No. 09/865,291, filed on May 24, 2001, now Pat. No. 6,900,304, which is a continuation-in-part of application No. 09/396,003, filed on Sep. 13, 1999, now abandoned, which is a continuation of application No. 08/792,553, filed on Jan. 31, 1997, now Pat. No. 5,981,200, which is a continuation-in-part of application No. 08/594,575, filed on Jan. 31, 1996, now Pat. No. 6,803,188.

(51) Int. Cl.
*C12P 21/04* (2006.01)

(52) U.S. Cl.
USPC ............... 435/69.7; 435/7; 435/21; 435/67.7; 435/320.1; 530/352; 530/350; 530/300

(58) Field of Classification Search
None
See application file for complete search history.

(56) References Cited

U.S. PATENT DOCUMENTS

| | | |
|---|---|---|
| 5,795,729 A | 8/1998 | Lee |
| 6,376,257 B1 | 4/2002 | Persechini |
| 6,410,255 B1 | 6/2002 | Pollok et al. |
| 6,465,199 B1 | 10/2002 | Craig et al. |
| 6,656,696 B2 * | 12/2003 | Craig et al. ............ 435/7.6 |

FOREIGN PATENT DOCUMENTS

| | | |
|---|---|---|
| WO | WO 98/02571 A1 | 1/1998 |
| WO | WO 00/71565 A2 | 11/2000 |

OTHER PUBLICATIONS

Wells, Biochemistry, vol. 29, pp. 8509-8517, 1990.*
Seffernick et al. (J. Bacteriology, vol. 183, pp. 2405-2410, 2001).*
Nagai, Yasuo et al.; "A fluorescent indicator for visualizing cAMP-induced phosphorylation in vivo"; 2000, *Nature Biotechnology*, vol. 18, pp. 313-316.

* cited by examiner

*Primary Examiner* — Hope Robinson
(74) *Attorney, Agent, or Firm* — Morgan, Lewis & Bockius LLP

(57) ABSTRACT

A chimeric phosphorylation indicator (CPI) as provided herein can contain a donor molecule, a phosphorylatable domain, a phosphoaminoacid binding domain (PAABD), and an acceptor molecule. Where the phosphorylatable domain is phosphorylatable by protein kinase C (PKC), the CPI is a c-kinase activity reporter (CKAR). Donor and acceptor molecules may be, independently, fluorescent proteins such as non-oligomerizing fluorescent proteins. A CPI can contain a phosphorylatable polypeptide and a fluorescent protein; the phosphorylatable polypeptide may be contained within the sequence of the fluorescent protein, or the fluorescent protein may be contained within the sequence of the phosphorylatable polypeptide. The spatiotemporal properties of the PKC signal pathway may be tested with CKAR, calcium-sensing fluorophores and FRET-based translocation assays. Polynucleotides encoding such CPIs, and kits containing the indicators and/or the polynucleotides, are provided. A method of using the chimeric phosphorylation indicators to detect a kinase or phosphatase in a sample is provided.

23 Claims, 14 Drawing Sheets

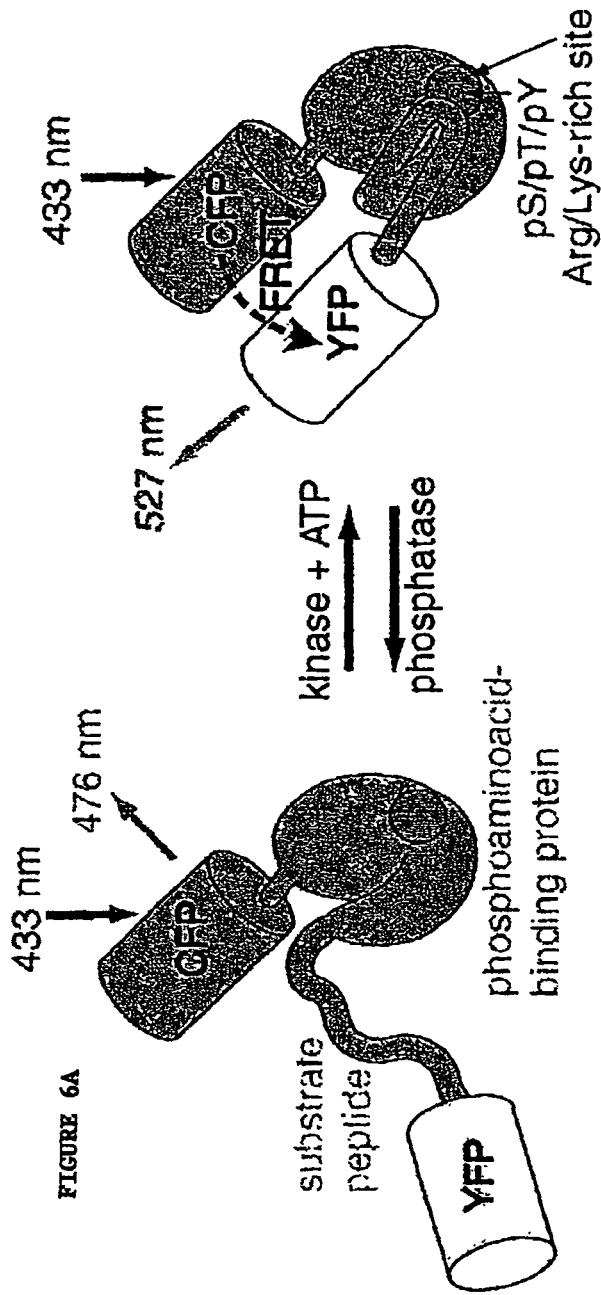
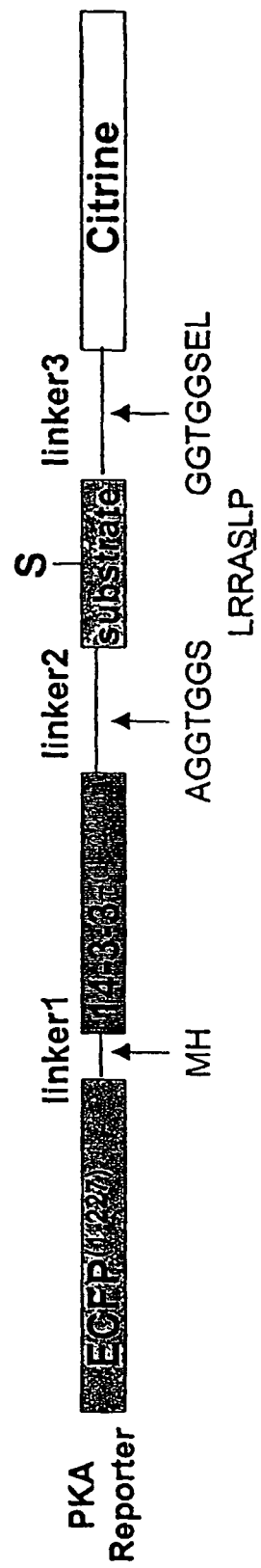
FIGURE 6A
FIGURE 6B

EGFR Reporter

Src Reporter c-kinase Reporter

SEQUENCE LISTING

```
<160> NUMBER OF SEQ ID NOS: 64

<210> SEQ ID NO 1
<211> LENGTH: 716
<212> TYPE: DNA
<213> ORGANISM: Aequorea victoria
<220> FEATURE:
<221> NAME/KEY: CDS
<222> LOCATION: (1)..(714)
<223> OTHER INFORMATION: green fluorescent protein (GFP)

<400> SEQUENCE: 1 atg agt aaa gga gaa gaa ctt ttc act gga gtt gtc cca att ctt gtt    48
Met Ser Lys Gly Glu Glu Leu Phe Thr Gly Val Val Pro Ile Leu Val
1               5                   10                  15 gaa tta gat ggt gat gtt aat ggg cac aaa ttt tct gtc agt gga gag    96
Glu Leu Asp Gly Asp Val Asn Gly His Lys Phe Ser Val Ser Gly Glu
            20                  25                  30 ggt gaa ggt gat gca aca tac gga aaa ctt acc ctt aaa ttt att tgc   144
Gly Glu Gly Asp Ala Thr Tyr Gly Lys Leu Thr Leu Lys Phe Ile Cys
        35                  40                  45 act act gga aaa cta cct gtt cca tgg cca aca ctt gtc act act ttc   192
Thr Thr Gly Lys Leu Pro Val Pro Trp Pro Thr Leu Val Thr Thr Phe
    50                  55                  60 tct tat ggt gtt caa tgc ttt tca aga tac cca gat cat atg aaa cag   240
Ser Tyr Gly Val Gln Cys Phe Ser Arg Tyr Pro Asp His Met Lys Gln
65                  70                  75                  80
```

```
cat gac ttt ttc aag agt gcc atg ccc gaa ggt tat gta cag gaa aga        288
His Asp Phe Phe Lys Ser Ala Met Pro Glu Gly Tyr Val Gln Glu Arg
                85                  90                  95 act ata ttt ttc aaa gat gac ggg aac tac aag aca cgt gct gaa gtc        336
Thr Ile Phe Phe Lys Asp Asp Gly Asn Tyr Lys Thr Arg Ala Glu Val
            100                 105                 110 aag ttt gaa ggt gat acc ctt gtt aat aga atc gag tta aaa ggt att        384
Lys Phe Glu Gly Asp Thr Leu Val Asn Arg Ile Glu Leu Lys Gly Ile
        115                 120                 125 gat ttt aaa gaa gat gga aac att ctt gga cac aaa ttg gaa tac aac        432
Asp Phe Lys Glu Asp Gly Asn Ile Leu Gly His Lys Leu Glu Tyr Asn
    130                 135                 140 tat aac tca cac aat gta tac atc atg gca gac aaa caa aag aat gga        480
Tyr Asn Ser His Asn Val Tyr Ile Met Ala Asp Lys Gln Lys Asn Gly
145                 150                 155                 160 atc aaa gtt aac ttc aaa att aga cac aac att gaa gat gga agc gtt        528
Ile Lys Val Asn Phe Lys Ile Arg His Asn Ile Glu Asp Gly Ser Val
                165                 170                 175 caa cta gca gac cat tat caa caa aat act cca att ggc gat ggc cct        576
Gln Leu Ala Asp His Tyr Gln Gln Asn Thr Pro Ile Gly Asp Gly Pro
            180                 185                 190 gtc ctt tta cca gac aac cat tac ctg tcc aca caa tct gcc ctt tcg        624
Val Leu Leu Pro Asp Asn His Tyr Leu Ser Thr Gln Ser Ala Leu Ser
        195                 200                 205 aaa gat ccc aac gaa aag aga gac cac atg gtc ctt ctt gag ttt gta        672
Lys Asp Pro Asn Glu Lys Arg Asp His Met Val Leu Leu Glu Phe Val
    210                 215                 220 aca gct gct ggg att aca cat ggc atg gat gaa cta tac aaa ta             716
Thr Ala Ala Gly Ile Thr His Gly Met Asp Glu Leu Tyr Lys
225                 230                 235

<210> SEQ ID NO 2
<211> LENGTH: 238
<212> TYPE: PRT
<213> ORGANISM: Aequorea victoria
<220> FEATURE:
<223> OTHER INFORMATION: green fluorescent protein (GFP)

<400> SEQUENCE: 2

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160
```

```
Ile Lys Val Asn Phe Lys Ile Arg His Asn Ile Glu Asp Gly Ser Val
            165                 170                 175

Gln Leu Ala Asp His Tyr Gln Gln Asn Thr Pro Ile Gly Asp Gly Pro
        180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 3
<211> LENGTH: 720
<212> TYPE: DNA
<213> ORGANISM: Artificial Sequence
<220> FEATURE:
<223> OTHER INFORMATION: synthetic enhanced green fluorescent protein
      (EGFP)
<220> FEATURE:
<221> NAME/KEY: CDS
<222> LOCATION: (1)..(720)
<223> OTHER INFORMATION: synthetic enhanced green fluorescent protein
      (EGFP), Aequorea GFP spectral variant

<400> SEQUENCE: 3 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
            20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
    50                  55                  60 ctg acc tac ggc gtg cag tgc ttc agc cgc tac ccc gac cac atg aag     240
Leu Thr Tyr Gly Val Gln Cys Phe Ser Arg Tyr Pro Asp His Met Lys
65                  70                  75                  80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag     336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc     384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac     432
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac     480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc     528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc     576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg     624
```

```
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc      672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag taa      720
Val Thr Ala Ala Gly Ile Thr Leu Gly Met Asp Glu Leu Tyr Lys
225                 230                 235

<210> SEQ ID NO 4
<211> LENGTH: 239
<212> TYPE: PRT
<213> ORGANISM: Artificial Sequence
<220> FEATURE:
<223> OTHER INFORMATION: synthetic enhanced green fluorescent protein
      (EGFP), Aequorea GFP spectral variant

<400> SEQUENCE: 4

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 5
<211> LENGTH: 720
<212> TYPE: DNA
<213> ORGANISM: Artificial Sequence
<220> FEATURE:
<223> OTHER INFORMATION: synthetic enhanced cyan fluorescent protein
      (ECFP), Aequorea GFP spectral variant
<220> FEATURE:
<221> NAME/KEY: CDS
<222> LOCATION: (1)..(720)
<223> OTHER INFORMATION: synthetic enhanced cyan fluorescent protein
      (ECFP), Aequorea GFP spectral variant
```

```
<400> SEQUENCE: 5 atg gtg agc aag ggc gag gag ctg ttc acc ggg gtg gtg ccc atc ctg        48
Met Val Ser Lys Gly Glu Glu Leu Phe Thr Gly Val Val Pro Ile Leu
1               5                   10                  15 gtc gag ctg gac ggc gac gta aac ggc cac agg ttc agc gtg tcc ggc        96
Val Glu Leu Asp Gly Asp Val Asn Gly His Arg Phe Ser Val Ser Gly
            20                  25                  30 gag ggc gag ggc gat gcc acc tac ggc aag ctg acc ctg aag ttc atc       144
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc       192
Cys Thr Thr Gly Lys Leu Pro Val Pro Trp Pro Thr Leu Val Thr Thr
50                  55                  60 ctg acc tgg ggc gtg cag tgc ttc agc cgc tac ccc gac cac atg aag       240
Leu Thr Trp Gly Val Gln Cys Phe Ser Arg Tyr Pro Asp His Met Lys
65                  70                  75                  80 cag cac gac ttc ttc aag tcc gcc atg ccc gaa ggc tac gtc cag gag       288
Gln His Asp Phe Phe Lys Ser Ala Met Pro Glu Gly Tyr Val Gln Glu
                85                  90                  95 cgt acc atc ttc ttc aag gac gac ggc aac tac aag acc cgc gcc gag       336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc       384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac       432
Ile Asp Phe Lys Glu Asp Gly Asn Ile Leu Gly His Lys Leu Glu Tyr
    130                 135                 140 aac tac atc agc cac aac gtc tat atc acc gcc gac aag cag aag aac       480
Asn Tyr Ile Ser His Asn Val Tyr Ile Thr Ala Asp Lys Gln Lys Asn
145                 150                 155                 160 ggc atc aag gcc cac ttc aag atc cgc cac aac atc gag gac ggc agc       528
Gly Ile Lys Ala His Phe Lys Ile Arg His Asn Ile Glu Asp Gly Ser
                165                 170                 175 gtg cag ctc gcc gac cac tac cag cag aac acc ccc atc ggc gac ggc       576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg       624
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc       672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag taa       720
Val Thr Ala Ala Gly Ile Thr Leu Gly Met Asp Glu Leu Tyr Lys
225                 230                 235
```

<210> SEQ ID NO 6
<211> LENGTH: 239
<212> TYPE: PRT
<213> ORGANISM: Artificial Sequence
<220> FEATURE:
<223> OTHER INFORMATION: synthetic enhanced cyan fluorescent protein
      (ECFP), Aequorea GFP spectral variant

<400> SEQUENCE: 6

```
Met Val Ser Lys Gly Glu Glu Leu Phe Thr Gly Val Val Pro Ile Leu
1               5                   10                  15

Val Glu Leu Asp Gly Asp Val Asn Gly His Arg Phe Ser Val Ser Gly
            20                  25                  30
```

```
Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
 50                  55                  60

Leu Thr Trp Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 7
<211> LENGTH: 720
<212> TYPE: DNA
<213> ORGANISM: Artificial Sequence
<220> FEATURE:
<223> OTHER INFORMATION: synthetic enhanced yellow fluorescent protein
      (EYFP), Aequorea GFP spectral variant
<220> FEATURE:
<221> NAME/KEY: CDS
<222> LOCATION: (1)..(720)
<223> OTHER INFORMATION: synthetic enhanced yellow fluorescent protein
      (EYFP), Aequorea GFP spectral variant

<400> SEQUENCE: 7 atg gtg agc aag ggc gag gag ctg ttc acc ggg gtg gtg ccc atc ctg       48
Met Val Ser Lys Gly Glu Glu Leu Phe Thr Gly Val Val Pro Ile Leu
 1               5                  10                  15 gtc gag ctg gac ggc gac gta aac ggc cac aag ttc agc gtg tcc ggc       96
Val Glu Leu Asp Gly Asp Val Asn Gly His Lys Phe Ser Val Ser Gly
            20                  25                  30 gag ggc gag ggc gat gcc acc tac ggc aag ctg acc ctg aag ttc atc      144
Glu Gly Glu Gly Asp Ala Thr Tyr Gly Lys Leu Thr Leu Lys Phe Ile
         35                  40                  45 tgc acc acc ggc aag ctg ccc gtg ccc tgg ccc acc ctc gtg acc acc      192
Cys Thr Thr Gly Lys Leu Pro Val Pro Trp Pro Thr Leu Val Thr Thr
 50                  55                  60 ttc ggc tac ggc gtg cag tgc ttc gcc cgc tac ccc gac cac atg aag      240
Phe Gly Tyr Gly Val Gln Cys Phe Ala Arg Tyr Pro Asp His Met Lys
 65                  70                  75                  80 cag cac gac ttc ttc aag tcc gcc atg ccc gaa ggc tac gtc cag gag      288
Gln His Asp Phe Phe Lys Ser Ala Met Pro Glu Gly Tyr Val Gln Glu
                 85                  90                  95 cgc acc atc ttc ttc aag gac gac ggc aac tac aag acc cgc gcc gag      336
Arg Thr Ile Phe Phe Lys Asp Asp Gly Asn Tyr Lys Thr Arg Ala Glu
```

```
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc      384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac      432
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac      480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc      528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc      576
Val Gln Leu Ala Asp His Tyr Gln Gln Asn Thr Pro Ile Gly Asp Gly
            180                 185                 190 ccc gtg ctg ctg ccc gac aac cac tac ctg agc tac cag tcc gcc ctg      624
Pro Val Leu Leu Pro Asp Asn His Tyr Leu Ser Tyr Gln Ser Ala Leu
        195                 200                 205 agc aaa gac ccc aac gag aag cgc gat cac atg gtc ctg ctg gag ttc      672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag taa      720
Val Thr Ala Ala Gly Ile Thr Leu Gly Met Asp Glu Leu Tyr Lys
225                 230                 235

<210> SEQ ID NO 8
<211> LENGTH: 239
<212> TYPE: PRT
<213> ORGANISM: Artificial Sequence
<220> FEATURE:
<223> OTHER INFORMATION: synthetic enhanced yellow fluorescent protein
      (EYFP), Aequorea GFP spectral variant

<400> SEQUENCE: 8

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Val Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
```

```
                   180                 185                 190
Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 9
<211> LENGTH: 720
<212> TYPE: DNA
<213> ORGANISM: Artificial Sequence
<220> FEATURE:
<223> OTHER INFORMATION: synthetic enhanced yellow fluorescent protein
      (EYFP), citrine, Aequorea GFP spectral variant, EYFP-V68L/Q69K
<220> FEATURE:
<221> NAME/KEY: CDS
<222> LOCATION: (1)..(720)
<223> OTHER INFORMATION: synthetic enhanced yellow fluorescent protein
      (EYFP), citrine, Aequorea GFP spectral variant, EYFP-V68L/Q69K

<400> SEQUENCE: 9 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
            20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
    50                  55                  60 ttc ggc tac ggc ctg aag tgc ttc gcc cgc tac ccc gac cac atg aag     240
Phe Gly Tyr Gly Leu Lys Cys Phe Ala Arg Tyr Pro Asp His Met Lys
65                  70                  75                  80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag     336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc     384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac     432
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac     480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc     528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc     576
Val Gln Leu Ala Asp His Tyr Gln Gln Asn Thr Pro Ile Gly Asp Gly
            180                 185                 190 ccc gtg ctg ctg ccc gac aac cac tac ctg agc tac cag tcc gcc ctg     624
Pro Val Leu Leu Pro Asp Asn His Tyr Leu Ser Tyr Gln Ser Ala Leu
        195                 200                 205 agc aaa gac ccc aac gag aag cgc gat cac atg gtc ctg ctg gag ttc     672
```

```
Ser Lys Asp Pro Asn Glu Lys Arg Asp His Met Val Leu Leu Glu Phe
    210                 215                 220
gtg acc gcc gcc ggg atc act ctc ggc atg gac gag ctg tac aag taa        720
Val Thr Ala Ala Gly Ile Thr Leu Gly Met Asp Glu Leu Tyr Lys
225                 230                 235
```

<210> SEQ ID NO 10
<211> LENGTH: 239
<212> TYPE: PRT
<213> ORGANISM: Artificial Sequence
<220> FEATURE:
<223> OTHER INFORMATION: synthetic enhanced yellow fluorescent protein
      (EYFP), citrine, Aequorea GFP spectral variant, EYFP-V68L/Q69K

<400> SEQUENCE: 10

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Phe Gly Tyr Gly Leu Lys Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 11
<211> LENGTH: 859
<212> TYPE: DNA
<213> ORGANISM: Discosoma sp.
<220> FEATURE:
<221> NAME/KEY: CDS
<222> LOCATION: (54)..(731)
<223> OTHER INFORMATION: DsRed red fluorescent protein (RFP)

<400> SEQUENCE: 11

```
gtttcagcca gtgacggtca gtgacagggt gagccacttg gtataccaac aaa atg        56
                                                          Met
                                                          1 agg tct tcc aag aat gtt atc aag gag ttc atg agg ttt aag gtt cgc      104
```

-continued

```
                    Arg Ser Ser Lys Asn Val Ile Lys Glu Phe Met Arg Phe Lys Val Arg
                                    5                   10                  15 atg gaa gga acg gtc aat ggg cac gag ttt gaa ata gaa ggc gaa gga            152
Met Glu Gly Thr Val Asn Gly His Glu Phe Glu Ile Glu Gly Glu Gly
            20                  25                  30 gag ggg agg cca tac gaa ggc cac aat acc gta aag ctt aag gta acc            200
Glu Gly Arg Pro Tyr Glu Gly His Asn Thr Val Lys Leu Lys Val Thr
        35                  40                  45 aag ggg gga cct ttg cca ttt gct tgg gat att ttg tca cca caa ttt            248
Lys Gly Gly Pro Leu Pro Phe Ala Trp Asp Ile Leu Ser Pro Gln Phe
50                  55                  60                  65 cag tat gga agc aag gta tat gtc aag cac cct gcc gac ata cca gac            296
Gln Tyr Gly Ser Lys Val Tyr Val Lys His Pro Ala Asp Ile Pro Asp
                    70                  75                  80 tat aaa aag ctg tca ttt cct gaa gga ttt aaa tgg gaa agg gtc atg            344
Tyr Lys Lys Leu Ser Phe Pro Glu Gly Phe Lys Trp Glu Arg Val Met
                85                  90                  95 aac ttt gaa gac ggt ggc gtc gtt act gta acc cag gat tcc agt ttg            392
Asn Phe Glu Asp Gly Gly Val Val Thr Val Thr Gln Asp Ser Ser Leu
            100                 105                 110 cag gat ggc tgt ttc atc tac aag gtc aag ttc att ggc gtg aac ttt            440
Gln Asp Gly Cys Phe Ile Tyr Lys Val Lys Phe Ile Gly Val Asn Phe
        115                 120                 125 cct tcc gat gga cct gtt atg caa aag aag aca atg ggc tgg gaa gcc            488
Pro Ser Asp Gly Pro Val Met Gln Lys Lys Thr Met Gly Trp Glu Ala
130                 135                 140                 145 agc act gag cgt ttg tat cct cgt gat ggc gtg ttg aaa gga gag att            536
Ser Thr Glu Arg Leu Tyr Pro Arg Asp Gly Val Leu Lys Gly Glu Ile
                    150                 155                 160 cat aag gct ctg aag ctg aaa gac ggt ggt cat tac cta gtt gaa ttc            584
His Lys Ala Leu Lys Leu Lys Asp Gly Gly His Tyr Leu Val Glu Phe
                165                 170                 175 aaa agt att tac atg gca aag aag cct gtg cag cta cca ggg tac tac            632
Lys Ser Ile Tyr Met Ala Lys Lys Pro Val Gln Leu Pro Gly Tyr Tyr
            180                 185                 190 tat gtt gac tcc aaa ctg gat ata aca agc cac aac gaa gac tat aca            680
Tyr Val Asp Ser Lys Leu Asp Ile Thr Ser His Asn Glu Asp Tyr Thr
        195                 200                 205 atc gtt gag cag tat gaa aga acc gag gga cgc cac cat ctg ttc ctt            728
Ile Val Glu Gln Tyr Glu Arg Thr Glu Gly Arg His His Leu Phe Leu
210                 215                 220                 225 taa ggctgaactt ggctcagacg tgggtgagcg gtaatgacca caaaaggcag                 781
cgaagaaaaa ccatgatcgt ttttttttagg ttggcagcct gaaatcgtag gaaatacatc        841
agaaatgtta caaacagg                                                        859
```

```
<210> SEQ ID NO 12
<211> LENGTH: 225
<212> TYPE: PRT
<213> ORGANISM: Discosoma sp.
<220> FEATURE:
<223> OTHER INFORMATION: DsRed fluorescent protein

<400> SEQUENCE: 12

Met Arg Ser Ser Lys Asn Val Ile Lys Glu Phe Met Arg Phe Lys Val
1               5                   10                  15

Arg Met Glu Gly Thr Val Asn Gly His Glu Phe Glu Ile Glu Gly Glu
            20                  25                  30

Gly Glu Gly Arg Pro Tyr Glu Gly His Asn Thr Val Lys Leu Lys Val
        35                  40                  45
```

```
Thr Lys Gly Gly Pro Leu Pro Phe Ala Trp Asp Ile Leu Ser Pro Gln
     50                  55                  60

Phe Gln Tyr Gly Ser Lys Val Tyr Val Lys His Pro Ala Asp Ile Pro
 65                  70                  75                  80

Asp Tyr Lys Lys Leu Ser Phe Pro Glu Gly Phe Lys Trp Glu Arg Val
                 85                  90                  95

Met Asn Phe Glu Asp Gly Gly Val Val Thr Val Thr Gln Asp Ser Ser
             100                 105                 110

Leu Gln Asp Gly Cys Phe Ile Tyr Lys Val Lys Phe Ile Gly Val Asn
         115                 120                 125

Phe Pro Ser Asp Gly Pro Val Met Gln Lys Lys Thr Met Gly Trp Glu
     130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225

<210> SEQ ID NO 13
<211> LENGTH: 18
<212> TYPE: PRT
<213> ORGANISM: Artificial Sequence
<220> FEATURE:
<223> OTHER INFORMATION: synthetic peptide linker

<400> SEQUENCE: 13

Gly Ser Thr Ser Gly Ser Gly Lys Pro Gly Ser Gly Glu Ser Thr
 1               5                  10                  15

Lys Gly

<210> SEQ ID NO 14
<211> LENGTH: 8
<212> TYPE: PRT
<213> ORGANISM: Artificial Sequence
<220> FEATURE:
<223> OTHER INFORMATION: synthetic phosphopeptide from PDGF receptor
<220> FEATURE:
<221> NAME/KEY: MOD_RES
<222> LOCATION: (2)..(2)
<223> OTHER INFORMATION: phosphorylated Tyr

<400> SEQUENCE: 14

Asp Tyr Ile Ile Pro Leu Pro Asp
 1               5

<210> SEQ ID NO 15
<211> LENGTH: 9
<212> TYPE: PRT
<213> ORGANISM: Artificial Sequence
<220> FEATURE:
<223> OTHER INFORMATION: synthetic phosphopeptide from TrkA
<220> FEATURE:
<221> NAME/KEY: MOD_RES
<222> LOCATION: (8)..(8)
<223> OTHER INFORMATION: phosphorylated Tyr
```

-continued

```
<400> SEQUENCE: 15

His Ile Ile Glu Asn Pro Gln Tyr Phe
1               5

<210> SEQ ID NO 16
<211> LENGTH: 8
<212> TYPE: PRT
<213> ORGANISM: Artificial Sequence
<220> FEATURE:
<223> OTHER INFORMATION: synthetic phosphopeptide
<220> FEATURE:
<221> NAME/KEY: MOD_RES
<222> LOCATION: (5)..(5)
<223> OTHER INFORMATION: phosphorylated Ser

<400> SEQUENCE: 16

Ala Arg Ser His Ser Tyr Pro Ala
1               5

<210> SEQ ID NO 17
<211> LENGTH: 6
<212> TYPE: PRT
<213> ORGANISM: Artificial Sequence
<220> FEATURE:
<223> OTHER INFORMATION: synthetic tetracysteine motif
<220> FEATURE:
<221> NAME/KEY: VARIANT
<222> LOCATION: (3)..(4)
<223> OTHER INFORMATION: Xaa = any amino acid

<400> SEQUENCE: 17

Cys Cys Xaa Xaa Cys Cys
1               5

<210> SEQ ID NO 18
<211> LENGTH: 15
<212> TYPE: PRT
<213> ORGANISM: Artificial Sequence
<220> FEATURE:
<223> OTHER INFORMATION: synthetic translocating domain peptide

<400> SEQUENCE: 18

Cys Arg Gln Ile Lys Trp Phe Gln Arg Arg Met Lys Trp Lys Lys
1               5                   10                  15

<210> SEQ ID NO 19
<211> LENGTH: 7
<212> TYPE: PRT
<213> ORGANISM: Artificial Sequence
<220> FEATURE:
<223> OTHER INFORMATION: synthetic PKA reporter linker 2 peptide,
      short linker peptide

<400> SEQUENCE: 19

Ala Gly Gly Thr Gly Gly Ser
1               5

<210> SEQ ID NO 20
<211> LENGTH: 7
<212> TYPE: PRT
<213> ORGANISM: Artificial Sequence
<220> FEATURE:
<223> OTHER INFORMATION: synthetic PKA reporter modified kemptide
      substrate peptide, serine/theronine kinase domain

<400> SEQUENCE: 20

Leu Arg Arg Ala Ser Leu Pro
1               5
```

```
<210> SEQ ID NO 21
<211> LENGTH: 8
<212> TYPE: PRT
<213> ORGANISM: Artificial Sequence
<220> FEATURE:
<223> OTHER INFORMATION: synthetic PKA reporter linker 3 peptide,
      second short linker peptide, flexible linker

<400> SEQUENCE: 21

Gly Gly Thr Gly Gly Ser Glu Leu
1               5

<210> SEQ ID NO 22
<211> LENGTH: 9
<212> TYPE: PRT
<213> ORGANISM: Artificial Sequence
<220> FEATURE:
<223> OTHER INFORMATION: synthetic EGFR reporter linker peptide

<400> SEQUENCE: 22

Gly Ser His Ser Gly Ser Gly Lys Pro
1               5

<210> SEQ ID NO 23
<211> LENGTH: 13
<212> TYPE: PRT
<213> ORGANISM: Artificial Sequence
<220> FEATURE:
<223> OTHER INFORMATION: synthetic EGFR reporter substrate domain
      peptide, tyrosine kinase phosphorylatable domain

<400> SEQUENCE: 23

Glu Glu Glu Ala Glu Tyr Met Asn Met Ala Pro Gln Ser
1               5                   10

<210> SEQ ID NO 24
<211> LENGTH: 15
<212> TYPE: PRT
<213> ORGANISM: Artificial Sequence
<220> FEATURE:
<223> OTHER INFORMATION: synthetic Src reporter linker peptide

<400> SEQUENCE: 24

Gly Ser Thr Ser Gly Ser Gly Lys Pro Gly Ser Gly Glu Gly Ser
1               5                   10                  15

<210> SEQ ID NO 25
<211> LENGTH: 6
<212> TYPE: PRT
<213> ORGANISM: Artificial Sequence
<220> FEATURE:
<223> OTHER INFORMATION: synthetic Src reporter substrate domain
      peptide, tyrosine kinase phosphorylatable domain

<400> SEQUENCE: 25

Glu Ile Tyr Gly Glu Phe
1               5

<210> SEQ ID NO 26
<211> LENGTH: 34
<212> TYPE: DNA
<213> ORGANISM: Artificial Sequence
<220> FEATURE:
<223> OTHER INFORMATION: synthetic PCR forward primer

<400> SEQUENCE: 26
gggcatgcat atggagaaga ctgagctgat ccag                              34
```

```
<210> SEQ ID NO 27
<211> LENGTH: 92
<212> TYPE: DNA
<213> ORGANISM: Artificial Sequence
<220> FEATURE:
<223> OTHER INFORMATION: synthetic PCR reverse primer

<400> SEQUENCE: 27
cgcggagctc gctgccgccg gtgccgccca ggctggcgcg acggaggctg ccgccggtgc      60
cgcctgcaga gtctgatgtc caaagtgtta gg                                   92

<210> SEQ ID NO 28
<211> LENGTH: 33
<212> TYPE: DNA
<213> ORGANISM: Artificial Sequence
<220> FEATURE:
<223> OTHER INFORMATION: synthetic mutagenesis primer

<400> SEQUENCE: 28
cgtcgcgcca gcctgccagg caccggcggc agc                                  33

<210> SEQ ID NO 29
<211> LENGTH: 33
<212> TYPE: DNA
<213> ORGANISM: Artificial Sequence
<220> FEATURE:
<223> OTHER INFORMATION: synthetic mutagenesis primer

<400> SEQUENCE: 29
gctgccgccg gtggctggca ggctggcgcg acg                                  33

<210> SEQ ID NO 30
<211> LENGTH: 32
<212> TYPE: DNA
<213> ORGANISM: Artificial Sequence
<220> FEATURE:
<223> OTHER INFORMATION: synthetic PCR primer for S475A mutant

<400> SEQUENCE: 30
gcctccgtcg cgccgcactg ccaggcaccg gc                                   32

<210> SEQ ID NO 31
<211> LENGTH: 32
<212> TYPE: DNA
<213> ORGANISM: Artificial Sequence
<220> FEATURE:
<223> OTHER INFORMATION: synthetic PCR primer for S475A mutant

<400> SEQUENCE: 31
gccggtgcct ggcagtgcgg cgcgacggag gc                                   32

<210> SEQ ID NO 32
<211> LENGTH: 7
<212> TYPE: PRT
<213> ORGANISM: Artificial sequence
<220> FEATURE:
<223> OTHER INFORMATION: synthetic kemptide substrate peptide,
      serine/theronine kinase domain

<400> SEQUENCE: 32

Leu Arg Arg Ala Ser Leu Gly
1               5

<210> SEQ ID NO 33
<211> LENGTH: 9
<212> TYPE: PRT
```

```
<213> ORGANISM: Artificial Sequence
<220> FEATURE:
<223> OTHER INFORMATION: synthetic substrate peptide derived from
      Raf-259

<400> SEQUENCE: 33

Ala Gln Arg Ser Thr Ser Thr Pro Asn
1               5

<210> SEQ ID NO 34
<211> LENGTH: 6
<212> TYPE: PRT
<213> ORGANISM: Artificial Sequence
<220> FEATURE:
<223> OTHER INFORMATION: synthetic consensus sequence recognized by
      14-3-3
<220> FEATURE:
<221> NAME/KEY: VARIANT
<222> LOCATION: (3)..(5)
<223> OTHER INFORMATION: Xaa = any amino acid

<400> SEQUENCE: 34

Arg Ser Xaa Ser Xaa Pro
1               5

<210> SEQ ID NO 35
<211> LENGTH: 4
<212> TYPE: PRT
<213> ORGANISM: Artificial Sequence
<220> FEATURE:
<223> OTHER INFORMATION: synthetic consensus PKA phosphorylation site
<220> FEATURE:
<221> NAME/KEY: VARIANT
<222> LOCATION: (3)..(3)
<223> OTHER INFORMATION: Xaa = any amino acid

<400> SEQUENCE: 35

Arg Arg Xaa Ser
1

<210> SEQ ID NO 36
<211> LENGTH: 4
<212> TYPE: PRT
<213> ORGANISM: Artificial Sequence
<220> FEATURE:
<223> OTHER INFORMATION: synthetic CaMKII kinase consensus sequence
<220> FEATURE:
<221> NAME/KEY: VARIANT
<222> LOCATION: (2)..(3)
<223> OTHER INFORMATION: Xaa = any amino acid
<220> FEATURE:
<221> NAME/KEY: VARIANT
<222> LOCATION: (4)..(4)
<223> OTHER INFORMATION: Xaa = Ser or Thr

<400> SEQUENCE: 36

Arg Xaa Xaa Xaa
1

<210> SEQ ID NO 37
<211> LENGTH: 4
<212> TYPE: PRT
<213> ORGANISM: Artificial Sequence
<220> FEATURE:
<223> OTHER INFORMATION: synthetic PKCbetaII kinase consensus sequence
<220> FEATURE:
<221> NAME/KEY: VARIANT
<222> LOCATION: (1)..(1)
<223> OTHER INFORMATION: Xaa = Lys or Arg
<220> FEATURE:
<221> NAME/KEY: VARIANT
<222> LOCATION: (2)..(3)
```

```
<223> OTHER INFORMATION: Xaa = any amino acid
<220> FEATURE:
<221> NAME/KEY: VARIANT
<222> LOCATION: (4)..(4)
<223> OTHER INFORMATION: Xaa = Ser or Thr

<400> SEQUENCE: 37

Xaa Xaa Xaa Xaa
1

<210> SEQ ID NO 38
<211> LENGTH: 39
<212> TYPE: DNA
<213> ORGANISM: Artificial Sequence
<220> FEATURE:
<223> OTHER INFORMATION: synthetic PCR amplification forward primer 2
      EGFR.Fwd

<400> SEQUENCE: 38
gccgcccgca tgcattggtt ccacgggaag ctgagccgg                              39

<210> SEQ ID NO 39
<211> LENGTH: 99
<212> TYPE: DNA
<213> ORGANISM: Artificial Sequence
<220> FEATURE:
<223> OTHER INFORMATION: synthetic PCR amplification reverse primer
      EGFRoptsub.Rev

<400> SEQUENCE: 39
taccatgagc tctgattgcg gagccatgtt catgtactca gcttcctctt caggcttccc       60
agatccagag tgagacccca cgggttgctc taggcacag                              99

<210> SEQ ID NO 40
<211> LENGTH: 35
<212> TYPE: DNA
<213> ORGANISM: Artificial Sequence
<220> FEATURE:
<223> OTHER INFORMATION: synthetic PCR amplification forward primer 3
      SrcSH2.Fwd

<400> SEQUENCE: 40
gccgctcgca tgcattggta ttttgggaag atcac                                  35

<210> SEQ ID NO 41
<211> LENGTH: 93
<212> TYPE: DNA
<213> ORGANISM: Artificial Sequence
<220> FEATURE:
<223> OTHER INFORMATION: synthetic PCR amplification reverse primer
      SrcSH2.Rev

<400> SEQUENCE: 41
caccatgagc tcaaattcac cgtagatctc agaaccctca ccagaacccg gcttcccaga       60
tccagatgta gacccacaga cgttagtcag gcg                                    93

<210> SEQ ID NO 42
<211> LENGTH: 7
<212> TYPE: PRT
<213> ORGANISM: Artificial Sequence
<220> FEATURE:
<223> OTHER INFORMATION: synthetic consensus sequence for 14-3-3eta
      recognition, phosphoserine/phosphothreonine binding domain
<220> FEATURE:
<221> NAME/KEY: VARIANT
<222> LOCATION: (2)..(2)
<223> OTHER INFORMATION: Xaa = Arg or Lys
<220> FEATURE:
```

```
<221> NAME/KEY: VARIANT
<222> LOCATION: (3)..(3)
<223> OTHER INFORMATION: Xaa = Phe, Arg, Ser or Asn
<220> FEATURE:
<221> NAME/KEY: VARIANT
<222> LOCATION: (4)..(4)
<223> OTHER INFORMATION: Xaa = Arg, His or Lys
<220> FEATURE:
<221> NAME/KEY: MOD_RES
<222> LOCATION: (5)..(5)
<223> OTHER INFORMATION: phosphorylated Ser
<220> FEATURE:
<221> NAME/KEY: VARIANT
<222> LOCATION: (6)..(6)
<223> OTHER INFORMATION: Xaa = Trp, Tyr, Phe or Leu

<400> SEQUENCE: 42

Arg Xaa Xaa Xaa Ser Xaa Pro
1               5

<210> SEQ ID NO 43
<211> LENGTH: 24
<212> TYPE: PRT
<213> ORGANISM: Artificial Sequence
<220> FEATURE:
<223> OTHER INFORMATION: synthetic phosphorylatable domain, PKC
      substrate sequence, consensus phosphorylation sequence for PKC
      flanked by flexible linker sequence

<400> SEQUENCE: 43

Gly Gly Ser Gly Gly Arg Phe Arg Arg Phe Gln Thr Leu Lys Ile Lys
1               5                   10                  15

Ala Lys Ala Gly Gly Ser Gly Gly
            20

<210> SEQ ID NO 44
<211> LENGTH: 14
<212> TYPE: PRT
<213> ORGANISM: Artificial Sequence
<220> FEATURE:
<223> OTHER INFORMATION: synthetic PKC phosphorylatable domain, PKC
      substrate sequence, consensus phosphorylation sequence for PKC

<400> SEQUENCE: 44

Arg Phe Arg Arg Phe Gln Thr Leu Lys Ile Lys Ala Lys Ala
1               5                   10

<210> SEQ ID NO 45
<211> LENGTH: 5
<212> TYPE: PRT
<213> ORGANISM: Artificial Sequence
<220> FEATURE:
<223> OTHER INFORMATION: synthetic flexible linker sequence

<400> SEQUENCE: 45

Gly Gly Ser Gly Gly
1               5

<210> SEQ ID NO 46
<211> LENGTH: 25
<212> TYPE: PRT
<213> ORGANISM: Artificial Sequence
<220> FEATURE:
<223> OTHER INFORMATION: synthetic PKC phosphorylatable domain

<400> SEQUENCE: 46

Lys Lys Lys Lys Lys Arg Phe Ser Phe Lys Lys Ser Phe Lys Leu Ser
1               5                   10                  15

Gly Phe Ser Phe Lys Lys Asn Leu Leu
```

<210> SEQ ID NO 47
<211> LENGTH: 11
<212> TYPE: PRT
<213> ORGANISM: Artificial Sequence
<220> FEATURE:
<223> OTHER INFORMATION: phosphorylatable domain

<400> SEQUENCE: 47

Lys Lys Arg Phe Ser Phe Lys Lys Phe Lys Leu
1               5                   10

<210> SEQ ID NO 48
<211> LENGTH: 23
<212> TYPE: PRT
<213> ORGANISM: Artificial Sequence
<220> FEATURE:
<223> OTHER INFORMATION: synthetic PKC phosphorylatable domain

<400> SEQUENCE: 48

Lys Arg Phe Ser Ser Lys Lys Ser Phe Lys Leu Ser Gly Phe Ser Phe
1               5                   10                  15

Lys Lys Asn Lys Lys Glu Ala
            20

<210> SEQ ID NO 49
<211> LENGTH: 23
<212> TYPE: PRT
<213> ORGANISM: Artificial Sequence
<220> FEATURE:
<223> OTHER INFORMATION: synthetic PKC phosphorylatable domain

<400> SEQUENCE: 49

Lys Arg Phe Ser Ser Lys Lys Ser Phe Lys Leu Ser Gly Phe Ser Phe
1               5                   10                  15

Lys Lys Ser Lys Lys Glu Ala
            20

<210> SEQ ID NO 50
<211> LENGTH: 17
<212> TYPE: PRT
<213> ORGANISM: Artificial Sequence
<220> FEATURE:
<223> OTHER INFORMATION: phosphorylatable domain

<400> SEQUENCE: 50

Lys Lys Phe Ser Ser Lys Lys Pro Phe Lys Leu Ser Gly Phe Ser Phe
1               5                   10                  15

Arg

<210> SEQ ID NO 51
<211> LENGTH: 23
<212> TYPE: PRT
<213> ORGANISM: Artificial Sequence
<220> FEATURE:
<223> OTHER INFORMATION: synthetic PKC phosphorylatable domain

<400> SEQUENCE: 51

Glu Thr Thr Ser Ser Phe Lys Lys Phe Phe Thr His Gly Thr Ser Phe
1               5                   10                  15

Lys Lys Ser Lys Glu Asp Asp
            20

<210> SEQ ID NO 52

```
<211> LENGTH: 23
<212> TYPE: PRT
<213> ORGANISM: Artificial Sequence
<220> FEATURE:
<223> OTHER INFORMATION: synthetic PKC phosphorylatable domain

<400> SEQUENCE: 52

Lys Leu Phe Ser Ser Ser Gly Leu Lys Lys Leu Ser Gly Lys Lys Gln
1               5                   10                  15

Lys Gly Lys Arg Gly Gly Gly
            20

<210> SEQ ID NO 53
<211> LENGTH: 23
<212> TYPE: PRT
<213> ORGANISM: Artificial Sequence
<220> FEATURE:
<223> OTHER INFORMATION: synthetic PKC phosphorylatable domain

<400> SEQUENCE: 53

Glu Gly Ile Thr Pro Trp Ala Ser Phe Lys Lys Met Val Thr Pro Lys
1               5                   10                  15

Lys Arg Val Arg Arg Pro Ser
            20

<210> SEQ ID NO 54
<211> LENGTH: 23
<212> TYPE: PRT
<213> ORGANISM: Artificial Sequence
<220> FEATURE:
<223> OTHER INFORMATION: synthetic PKC phosphorylatable domain

<400> SEQUENCE: 54

Glu Gly Val Ser Thr Trp Glu Ser Phe Lys Arg Leu Val Thr Pro Arg
1               5                   10                  15

Lys Lys Ser Lys Ser Lys Leu
            20

<210> SEQ ID NO 55
<211> LENGTH: 4
<212> TYPE: PRT
<213> ORGANISM: Artificial Sequence
<220> FEATURE:
<223> OTHER INFORMATION: synthetic PKC phosphorylatable domain

<400> SEQUENCE: 55

Arg Thr Pro Ser
1

<210> SEQ ID NO 56
<211> LENGTH: 68
<212> TYPE: PRT
<213> ORGANISM: Artificial Sequence
<220> FEATURE:
<223> OTHER INFORMATION: synthetic phosphoaminoacid binding domain
      (PAABD), FHA1 phosphothreonine binding domain from yeast
      checkpoint protein rad53p

<400> SEQUENCE: 56

Trp Thr Phe Gly Arg Asn Pro Ala Cys Asp Tyr His Leu Gly Asn Ile
1               5                   10                  15

Ser Arg Leu Ser Asn Lys His Phe Gln Ile Leu Leu Gly Glu Asp Gly
            20                  25                  30

Asn Leu Leu Leu Asn Asp Ile Ser Thr Asn Gly Thr Trp Leu Asn Gly
        35                  40                  45
```

```
Gln Lys Val Glu Lys Asn Ser Asn Gln Leu Leu Ser Gln Gly Asp Glu
        50                  55                  60

Ile Thr Val Gly
 65

<210> SEQ ID NO 57
<211> LENGTH: 81
<212> TYPE: PRT
<213> ORGANISM: Artificial Sequence
<220> FEATURE:
<223> OTHER INFORMATION: synthetic phosphoaminoacid binding domain
      (PAABD), FHA2 phosphothreonine binding domain from yeast
      checkpoint protein rad53p

<400> SEQUENCE: 57

Phe Phe Ile Gly Arg Ser Glu Asp Cys Asn Cys Lys Ile Glu Asp Asn
 1               5                  10                  15

Arg Leu Ser Arg Val His Cys Phe Ile Phe Lys Lys Arg His Ala Val
            20                  25                  30

Gly Lys Ser Met Tyr Glu Ser Pro Ala Gln Gly Leu Asp Asp Ile Trp
        35                  40                  45

Tyr Cys His Thr Gly Thr Asn Val Ser Tyr Leu Asn Asn Asn Arg Met
    50                  55                  60

Ile Gln Gly Thr Lys Phe Leu Leu Gln Asp Gly Asp Glu Ile Lys Ile
 65                  70                  75                  80

Ile

<210> SEQ ID NO 58
<211> LENGTH: 4
<212> TYPE: PRT
<213> ORGANISM: Artificial Sequence
<220> FEATURE:
<223> OTHER INFORMATION: synthetic membrane targeting domain

<400> SEQUENCE: 58

Cys Leu Leu Leu
 1

<210> SEQ ID NO 59
<211> LENGTH: 10
<212> TYPE: PRT
<213> ORGANISM: Artificial Sequence
<220> FEATURE:
<223> OTHER INFORMATION: synthetic membrane targeting domain

<400> SEQUENCE: 59

Met Leu Cys Cys Met Arg Arg Thr Lys Gln
 1               5                  10

<210> SEQ ID NO 60
<211> LENGTH: 16
<212> TYPE: PRT
<213> ORGANISM: Artificial Sequence
<220> FEATURE:
<223> OTHER INFORMATION: synthetic membrane targeting domain

<400> SEQUENCE: 60

Met Gly Cys Ile Lys Ser Lys Arg Lys Asp Asn Leu Asn Asp Asp Glu
 1               5                  10                  15

<210> SEQ ID NO 61
<211> LENGTH: 12
<212> TYPE: PRT
<213> ORGANISM: Artificial Sequence
<220> FEATURE:
```

```
<223> OTHER INFORMATION: synthetic polypeptide linker

<400> SEQUENCE: 61

Gly His Gly Thr Gly Ser Thr Gly Ser Gly Ser Ser
1               5                   10

<210> SEQ ID NO 62
<211> LENGTH: 13
<212> TYPE: PRT
<213> ORGANISM: Artificial Sequence
<220> FEATURE:
<223> OTHER INFORMATION: synthetic polypeptide linker

<400> SEQUENCE: 62

Arg Met Gly Ser Thr Ser Gly Ser Thr Lys Gly Gln Leu
1               5                   10

<210> SEQ ID NO 63
<211> LENGTH: 22
<212> TYPE: PRT
<213> ORGANISM: Artificial Sequence
<220> FEATURE:
<223> OTHER INFORMATION: synthetic polypeptide linker

<400> SEQUENCE: 63

Arg Met Gly Ser Thr Ser Gly Ser Gly Lys Pro Gly Ser Gly Glu Gly
1               5                   10                  15

Ser Thr Lys Gly Gln Leu
            20

<210> SEQ ID NO 64
<211> LENGTH: 6
<212> TYPE: PRT
<213> ORGANISM: Artificial Sequence
<220> FEATURE:
<223> OTHER INFORMATION: synthetic N-terminal His-6 tag

<400> SEQUENCE: 64

His His His His His His
1               5
```

CHIMERIC PHOSPHORYLATION INDICATOR

This application is a continuation-in-part (CIP) of U.S. Ser. No. 09/865,291, filed May 24, 2001, now U.S. Pat. No. 6,900,304, which is a CIP of U.S. Ser. No. 09/396,003, filed Sep. 13, 1999, which is a continuation (CON) of U.S. Ser. No. 08/792,553, filed Jan. 31, 1997 (now U.S. Pat. No. 5,981,200), which is a CIP of U.S. Ser. No. 08/594,575, filed Jan. 31, 1996 (now U.S. Pat. No. 6,803,188), the entire contents of each of which is incorporated herein by reference.

This invention was made with government support under Grant No. GM 62114 awarded by the National Institutes of Health. The government has certain rights in this invention.

BACKGROUND OF THE INVENTION

1. Field of the Invention

The present invention relates generally to reagents for determining kinase and phosphatase activity, and more specifically to chimeric proteins containing two fluorescent proteins and a phosphorylatable domain, and methods of using such chimeric proteins to detect kinase or phosphatase activity.

2. Background Information

Phosphorylation is the most important way that individual proteins are post-translationally modified to modulate their function, while practically all signal transduction involves dynamics of protein-protein interaction. Phosphorylation is catalyzed and controlled by kinases such as Calcium modulated kinase (CaM kinase, such as CaMKII), protein kinase A (PKA), protein kinase C (PKC), and other kinases. Various technologies have been used to enumerate the main phosphorylation/dephosphorylation events and interacting protein partners involved in cell function, including, for example, function of cardiomyocytes and B lymphocytes. However, the most common currently used technologies such as two dimensional gel electrophoresis, mass spectrometry, co-immunoprecipitation assays, and two-hybrid screens require destroying large numbers of the cells or transferring genes to heterologous organisms. As such, these methods have poor temporal and spatial resolution, and are insufficient to directly probe physiological functions such as contracture or chemotaxis, which occur on the time scale of milliseconds to minutes.

The most widely used method for detecting phosphorylation of specific proteins in single cells utilizes antibodies that discriminate between the phosphorylated and dephosphorylated forms of an antigen. Such antibodies can, in principle, reveal the phosphorylation state of the endogenous protein just prior to the time the cells were fixed for examination, without any introduction of exogenous substrates. However, the identification of antibodies that can discriminate between a phosphorylated and unphosphorylated form of a protein is time consuming and expensive. In addition, the necessary immunocytochemistry is tedious, and is difficult to reassemble into a quantitative time course.

PKC is known to play a key role in maintaining balance between normal growth and transformation (Nishizuka, 1995). PKC function in cells is exquisitely controlled by three major mechanisms: phosphorylation, required for catalytic competence, membrane-targeting, required for conformational activation, and protein:protein interactions which poise the enzyme at specific intracellular locations (Mellor and Parker, 1998; Newton, 2002b). Pertubation of any of these mechanisms disrupts cell function by altering the degree of substrate phosphorylation. A fluorescent protein, Green Fluorescent Protein (GFP) has been used to visualize translocation of PKC to membranes upon generation of diacylglycerol (DAG) and increases in calcium in living cells. (Oancea and Meyer, 1998; Sakai et al., 1997; Shirai et al., 1998b). These studies have revealed a wealth of information on the kinetics and localization of PKC inside the cell. However, GFP-labeling has not proven sufficient to determine the activation state of PKC or PKC-substrate phosphorylation. However, translocation and activation are different processes. Thus, it is not clear to what extent visualization of PKC translocation provides a measure of PKC activation or of PKC substrate phosphorylation.

Previous techniques for imaging protein heterodimerization in single cells have included observing luminescence resonance energy transfer (LRET) from a lanthanide donor attached to an antibody against one member of the heterodimer to a red dye attached to an antibody against the other partner (Root, Proc. Natl. Acad. Sci., USA 94:5685-5690, 1997). This approach has the same advantages and disadvantages as phosphorylation-specific antibodies, including it is applicable to examining endogenous proteins in intact non-transfected tissues, but has poor time resolution and difficulty in generating a continuous time course. Another mode of energy transfer is bioluminescence resonance energy transfer, in which the donor is a luciferase and the acceptor is a GFP (Xu et al., Proc. Natl. Acad. Sci., USA 96:151-156, 1999). However, although emission from multiple cells may be detectable, the feebleness of bioluminescence would be expected to make the technique difficult or impossible to use with single mammalian cells, especially if high spatial resolution is desired.

Additionally, reporters have been designed that alter fluorescence resonance energy transfer (FRET) between fluorescent proteins (Miyawaki and Tsien, 2000) or the intrinsic fluorescent properties of a fluorescent protein (Llopis et al., 1998; Nagai et al., 2001). Reporters based on FRET between fluorescent proteins can be used to glean information from living cells, provided that such reporters do not significantly perturb cell function (for example by buffering of cell signals resulting from reporter overexpression), and provided reporter specificity is maintained in cells. FRET reporters for kinase activity have been described (Sato et al., 2002; Ting et al., 2001; Zhang et al., 2001).

In order to achieve dynamic recording of phosphorylation in single cells, peptides have been labeled with acrylodan, a probe whose fluorescence can be sensitive to the phosphorylation of the peptide. For example, when acrylodan was attached to a peptide from myosin light chain, an approximately 40% decrease in emission peak amplitude upon phosphorylation in vitro was observed. When microinjected into fibroblasts, the peptide incorporated into stress fibers, but no dynamic changes were observable. Substrates for CaMKII and PKA also have been labeled with acrylodan and, after exposure to the kinase, fluorescence was about 200% and 97%, respectively, of initial values. These peptides were hydrophobic enough to stain live cells, and local intensity changes of up to 10% to 20% of initial fluorescence were seen in some regions. The fluorescence of the PKA substrate simultaneously decreased in the cytosol and increased in the nucleus by an amount that was greater than could be explained by the in vitro sensitivity, indicating that more complex factors such as translocation were dominating.

Although the use of acrylodan-labeled peptides provides no rational mechanism for phosphorylation sensitivity, the approach of developing phosphorylation-sensitive fluorescent substrates may be worth pursuing. Thus, a need exists for phosphorylation-sensitive indicators that can be used to detect phosphorylation or dephosphorylation events in a cell. The present invention satisfies this need and provides additional advantages.

SUMMARY OF THE INVENTION

The present invention relates to a chimeric phosphorylation indicator, which may comprise, in operative linkage, a first fluorescent protein, a phosphoaminoacid binding domain comprising the forkhead-associated (FHA2) sequence FFIGRSEDCNCKIEDNRLSRVH-CFIFKKRHAVGKSMYESPAQGLDDIWYCHTGTN VSYLNNNRMIQGTKFLLQDGDEIKII (SEQ ID NO: 57), a protein kinase C (PKC)phosphorylatable domain comprising the amino acid sequence RFRRFQTLKIKAKA (SEQ ID NO:44), and a second fluorescent protein, wherein the first and the second fluorescent proteins are different, at least one of the first and second fluorescent proteins comprises a non-oligomerizing fluorescent protein, and the first and second fluorescent proteins are selected from the group consisting of green fluorescent proteins (GFPs), red fluorescent proteins (RFPs), and fluorescent proteins related to a GFP or an RFP, wherein a fluoresyent protein related to a GFP or related to an RFP comprises an amino acid sequence having at least 90% sequence homology to a GFP or an RFP. The first and the second fluorescent proteins exhibit a detectable resonance energy transfer when the first fluorescent protein is excited, while the PKC-phosphorylatable domain and phosphoaminoacid binding domain do not substantially emit light to excite the second fluorescent protein. The fluorescent protein may be a non-oligomerizing fluorescent protein. The chimeric phosphorylation indicator may further comprise a polypeptide linker adjacent the PKC substrate phosphorylatable domain. A polypeptide linker may comprise between about 3 to about 50 amino acid residues, or between about 4 to about 30 amino acid resdues, or between about 5 to about 15 amino acid residues. A polypeptide linker may comprise, for example, GGSGG (SEQ ID NO: 45), GHGTGSTGSGSS (SEQ ID NO: 61), RMGSTSGSTKGQL (SEQ ID NO: 62), or RMGSTSGSGKPGSGEGSTKGQL (SEQ ID NO: 63).

A fluorescent protein in a chimeric phosphorylation indictor can be a green fluorescent protein (GFP), a red fluorescent protein (RFP), or a fluorescent protein related to a GFP or an RFP, including a non-oligomerizing fluorescent protein. An RFP, for example, can be a Discosoma RFP or a fluorescent protein related to a Discosoma RFP such as Discosoma DsRed (SEQ ID NO:12) or a mutant thereof (SEQ ID NO:12, including an I125R mutation), or a non-oligomerizing tandem DsRed containing, for example, two RFP monomers operatively linked by a peptide linker. For example, a non-oligomerizing tandem RFP can contain two DsRed (SEQ ID NO:12) monomers or two mutant DsRed-I125R monomers operatively linked by a peptide having an amino acid sequence as set forth as SEQ ID NO: 13.

A GFP useful in a chimeric phosphorylation indicator can be an Aequorea GFP, a Renilla GFP, a Phialidium GFP, or a fluorescent protein related to an Aequorea GFP, a Renilla GFP, or a Phialidium GFP. A fluorescent protein related to an Aequorea GFP, for example, can be a cyan fluorescent protein (CFP), or a yellow fluorescent protein (YFP; e.g., citrine (SEQ ID NO: 10 with Q69M)), or a variant (e.g., a spectral variant) of CFP or YFP, including an enhanced GFP (EGFP; SEQ ID NO:4), an enhanced CFP (ECFP; SEQ ID NO:6), an ECFP(1-227) (amino acids 1 to 227 of SEQ ID NO:6), an EYFP-V68L/Q69K (SEQ ID NO:10), an enhanced YFP (EYFP; SEQ ID NO:8), or other variant. In particular, a fluorescent protein related to an Aequorea GFP, a Discosoma RFP, or other fluorescent protein may be a non-oligomerizing fluorescent protein. A non-oligomerizing fluorescent protein is a fluorescent protein having a reduced propensity to oligomerize as compared to a reference fluorescent protein. For example, a non-oligomerizing fluorescent protein related to a GFP may have a mutation of an amino acid residue corresponding to A206, L221, F223, or a combination thereof of SEQ ID NO:2, for example, an A206K mutation, an L221K mutation, an F223R mutation, or an L221K and F223R mutation of SEQ ID NO:2; or an A206K mutation, an L221K mutation, an F223R mutation, or an L221K and F223R mutation of SEQ ID NO:6 or SEQ ID NO:10. Non-oligomerizing fluorescent proteins having one or more of these mutations may be, for example, a monomeric GFP (mGFP), a monomeric CFP (mCFP) or a monomeric YFP (mYFP) where the mutations are with respect to a corresponding GFP, CFP, or YFP reference sequence. A non-oligomerizing fluorescent protein related to a Discosoma RFP may be, for example, an I125R DsRed mutant (SEQ ID NO:12, including an I125R mutation).

In embodiments of the invention, the PKC phosphorylatable domain in a chimeric phosphorylation indicator of the invention may be any domain that can be phosphorylated by PKC, or that can contain a phosphate group and can be dephosphorylated by a specific phosphatase. Thus, the phosphorylatable domain can be a synthetic peptide, a peptide portion of a naturally-occurring kinase or phosphatase substrate, a peptidomimetic, a polynucleotide, or the like. By way of example, a PKC phosphorylatable domain may include an amino acid sequence such as, for example, that set forth in SEQ ID NO:37 or SEQ ID NO:44 and SEQ ID NOs:46-55, where SEQ ID NO: 44 is RFRRFQTLKIKAKA; SEQ ID NO: 46 is KKKKKRFSFKKSFKLSGFSFKKNLL; SEQ ID NO: 47 is KKRFSFKKFKL, SEQ ID NO: 48 is KRFSSKKS-FKLSGFSFKKNKKEA; SEQ ID NO: 49 is KRFSSKKS-FKLSGFSFKKSKKEA; SEQ ID NO: 50 is KKF-SSKKPFKLSGFSFR; SEQ ID NO: 51 is ETTSSFKKFFTHGTSFKKSKEDD; SEQ ID NO: 52 is KLFSSSGLKKLSGKKQKGKRGGG; SEQ ID NO: 53 is EGITPWASFKKMVTPKKRVRRPS; SEQ ID NO: 54 is EGVSTWESFKRLVTPRKKSKSKL; and SEQ ID NO: 55 is RTPS.

In other embodiments, the specific amino acid that can be phosphorylated by a kinase in the phosphorylatable domain of a chimeric phosphorylation indicator is not phosphorylated, such that the indicator can be used to detect the presence of the kinase in a sample. In other embodiments, the specific amino acid that can be phosphorylated by a kinase in the phosphorylatable domain of a chimeric phosphorylation indicator is phosphorylated, such that the indicator can be used to detect the presence of a phosphatase in a sample. The specific amino acid can be any amino acid that can be phosphorylated by a kinase or dephosphorylated by a phosphatase, for example, serine, threonine, tyrosine, or a combination thereof.

The phosphoaminoacid binding domain (PAABD) in a chimeric phosphorylation indicator of the invention can be an PAABD that specifically binds the particular phosphoaminoacid that is present in the indicator or that can be formed due to phosphorylation of the indicator by a kinase. For example, where the phosphorylatable domain is a C-kinase substrate domain, the phosphoaminoacid binding domain may be a FHAI phosphothreonine binding domain from the yeast checkpoint protein rad53p (SEQ ID NO: 56), or a FHA2 phosphothreonine binding domain from the yeast checkpoint protein rad53p (SEQ ID NO: 57), and is preferably SEQ ID NO: 57. The forkhead-associated (FHA) domain is a small protein module shown to recognize phosphothreonine epitopes on proteins with a striking specificity (Durocher et al., FEBS Letters 513:58-66 (2002)).

A chimeric phosphorylation indicator specific for detecting activity of a C-Kinase may be termed a "C-Kinase Activity Reporter" (CKAR) and, for example, may be composed of a CFP and a YFP flanking a PKC substrate sequence tethered by a flexible linker to an FHA2 phosphothreonine binding domain from the yeast checkpoint protein rad53p SEQUENCES. The CFP may be, for example, an mCFP and the YFP may be, for example, an mYFP, wherein an mCFP and an mYFP are variants of CFP and YFP respectively having a mutation of an amino acid residue corresponding to A206, L221, F223, or a combination thereof of SEQ ID NO:2, for example, an A206K mutation, an L221K mutation, an F223R mutation, or an L221K and F223R mutation of SEQ ID NO:2; or an A206K mutation, an L221K mutation, an F223R mutation, or an L221K and F223R mutation of SEQ ID NO:6 or SEQ ID NO:10. Alternatively, or in addition, a CKAR may include a red fluorescent protein, such as a non-oligomerizing fluorescent protein related to DsRed, such as, for example, an I125R DsRed mutant (SEQ ID NO:12, including an I125R mutation).

A CKAR may be exemplified herein by a fusion protein containing, in an orientation from the amino terminus to carboxy terminus, a CFP, a linker, a phosphoaminoacid binding domain, a flexible linker GGSGG (SEQ ID NO: 45), an RFRRFQTLKIKAKA (SEQ ID NO:44) phosphorylatable domain, a GGSGG (SEQ ID NO:45) linker, and a YFP. For example, the phosphoaminoacid binding domain may be an FHA1 (SEQ ID NO: 56) or an FHA2 domain (SEQ ID NO: 57). The phosphoaminoacid binding domain is preferably FHA2 (SEQ ID NO: 57). In more preferred embodiments, CKAR may be exemplified herein by a fusion protein containing, in an orientation from the amino terminus to carboxy terminus, mCFP, a linker, a FHA2 (SEQ ID NO: 57) phosphoaminoacid binding domain, a flexible linker GGSGG (SEQ ID NO: 45), an RFRRFQTLKIKAKA (SEQ ID NO:44) phosphorylatable domain, a GGSGG (SEQ ID NO:45) linker, and mYFP, where an mCFP and an MYFP are as discussed above.

The present invention also relates to a chimeric phosphorylation indicator, which contains a phosphorylatable polypeptide and a fluorescent protein. The specific amino acid that can be phosphorylated by a kinase in the phosphorylatable polypeptide can be unphosphorylated, such that the indicator can be used to detect a kinase activity, or can be phosphorylated, such that the indicator can be used to detect a phosphatase activity.

In one embodiment of a chimeric phosphorylation indicator containing a phosphorylatable polypeptide and a fluorescent protein, the phosphorylatable polypeptide comprises an N-terminal portion and a C-terminal portion, and the fluorescent protein is operatively inserted between the N-terminal portion and C-terminal portion of the phosphorylatable polypeptide. The fluorescent protein can be any fluorescent protein, such as a non-oligomerizing fluorescent protein, and may be, for example, a GFP, an RFP, or a fluorescent protein related to a GFP or an RFP, and can be in a circularly permuted form. For example, a non-oligomerizing fluorescent protein may be, for example, an mGFP, an mCFP or an mYFP. The phosphorylatable polypeptide can be any substrate for a kinase, for example, a tyrosine kinase or a serine/threonine kinase, including PKC, or for a phosphatase. The fluorescent protein can be operatively inserted into any region of the phosphorylatable polypeptide, for example, in a hinge region or a turn, provided the ability of the polypeptide to act as a substrate is not disrupted.

In another embodiment, a chimeric phosphorylation indicator containing a phosphorylatable polypeptide and a fluorescent protein further contains a phosphoaminoacid binding domain operatively linked to the phosphorylatable polypeptide, wherein the fluorescent protein comprises an N-terminal portion and a C-terminal portion, and wherein the phosphorylatable polypeptide and operatively linked phosphoaminoacid binding domain is operatively inserted between the N-terminal portion and C-terminal portion of the fluorescent protein. The fluorescent protein can be any fluorescent protein, such as a non-oligomerizing fluorescent protein, including, a GFP, an RFP, or a fluorescent protein related to a GFP or an RFP. For example, the fluorescent protein can be an EYFP, and the phosphorylatable polypeptide and operatively linked phosphoaminoacid binding domain can operatively inserted between an amino acid sequence corresponding to amino acid positions 145 and 146 of the EYFP or can be substituted for amino acid 145. A fluorescent protein that is a non-oligomerizing fluorescent protein may be, for example, mCFP or mYFP, wherein an mCFP and an mYFP are variants of CFP and YFP respectively having a mutation of an amino acid residue corresponding to A206, L221, F223, or a combination thereof of SEQ ID NO:2, for example, an A206K mutation, an L221K mutation, an F223R mutation, or an L221K and F223R mutation of SEQ ID NO:2; or an A206K mutation, an L221K mutation, an F223R mutation, or an L221K and F223R mutation of SEQ ID NO:6 or SEQ ID NO:10. In a further example, a non-oligomerizing fluorescent protein may also be a mutant DsRed, which has an amino acid sequence of SEQ ID NO:12, and including an I125R mutation.

The present invention also relates to polynucleotide encoding chimeric phosphorylation indicator, which contains, in operative linkage, a donor molecule, a phosphorylatable domain, a phosphoaminoacid binding domain, and an acceptor molecule, wherein the phosphoaminoacid binding domain specifically binds to a phosphoaminoacid when present in the phosphorylatable domain, the donor molecule and the acceptor molecule exhibit a detectable resonance energy transfer when the donor is excited, and the phosphorylatable domain and phosphoaminoacid binding domain do not substantially emit light to excite the acceptor. The donor and/or acceptor molecules may be, independently, fluorescent proteins, such as, for example, non-oligomerizing fluorescent proteins. In addition, the present invention relates to a polynucleotide encoding a chimeric phosphorylation indicator containing a phosphorylatable polypeptide and a fluorescent protein, wherein the phosphorylatable polypeptide includes an N-terminal portion and a C-terminal portion, and the fluorescent protein is operatively inserted between the N-terminal portion and C-terminal portion of the phosphorylatable polypeptide. The present invention further relates to a polynucleotide encoding a chimeric phosphorylation indicator containing a phosphoaminoacid binding domain operatively linked to a phosphorylatable polypeptide and a fluorescent protein, wherein the fluorescent protein includes an N-terminal portion and a C-terminal portion, and wherein the phosphorylatable polypeptide and operatively linked phosphoaminoacid binding domain is operatively inserted between the N-terminal portion and C-terminal portion of the fluorescent protein. Such a fluorescent protein may be a non-oligomerizing fluorescent protein or other fluorescent protein.

Also provided is a vector containing a polynucleotide of the invention, including an expression vector, as well as host cells that contain a polynucleotide of the invention or a vector containing such a polynucleotide. In one embodiment, a polynucleotide of the invention is operatively linked to an expression control sequence, for example, a transcription regulatory element, a translation regulatory element, or a combination thereof. In another embodiment, the polynucleotide is operatively linked to a nucleotide sequence encoding a membrane translocating domain or a cell compartmentalization domain.

The present invention also relates to kits, which contain at least one chimeric phosphorylation indicator of the invention, or a polynucleotide encoding such an indicator. A kit of the invention also can contain a plurality of different chimeric phosphorylation indicators, or of encoding polynucleotides, as well as a combination thereof. Where a kit contains a plurality of different chimeric phosphorylation indicators, the different indicators can contain different phosphorylatable domains, or different donor molecules or acceptor molecules or both, or different fluorescent proteins (such as fluorescent proteins including at least one non-oligomerizing fluorescent protein, or including different non-oligomerizing fluorescent proteins), as appropriate to the chimeric phosphorylatable indicator. Where a kit contains a polynucleotide encoding a chimeric phosphorylatable indicator, the polynucleotide can be in a vector, or in a host cell, or can be operatively linked to one or more expression control sequences. Where a kit contains a plurality of different polynucleotides, the polynucleotides can encode a different chimeric phosphorylation indicator, or each can contain different expression control sequences, or be contained in different vectors, particularly different expression vectors.

The present invention further relates to a method for detecting a kinase or phosphatase in a sample. In one embodiment, a method of the invention is performed, for example, contacting the sample with a chimeric phosphorylatable indicator, which contains, in operative linkage, a donor molecule, a phosphorylatable domain, a phosphoaminoacid binding domain, and an acceptor molecule, wherein the phosphoaminoacid binding domain specifically binds to a phosphoaminoacid when present in the phosphorylatable domain, the donor molecule and the acceptor molecule exhibit a detectable resonance energy transfer when the donor is excited, and the phosphorylatable domain and phosphoaminoacid binding domain do not substantially emit light to excite the acceptor; exciting the donor molecule; and determining a fluorescence or luminescence property in the sample, such as fluorescent resonance energy transfer (FRET) or luminescent resonance energy transfer (LRET), wherein the presence of a kinase or phosphatase in the sample results in a change in the degree of FRET or LRET, thereby detecting the kinase or phosphatase in the sample. The change in the degree of FRET or LRET can be an increased amount of FRET or LRET, or can be a decreased amount of FRET or LRET, and the change can be indicative of the presence of a kinase in the sample, or, where the phosphorylatable domain is phosphorylated prior to contacting the sample with a chimeric phosphorylatable indicator, can be indicative of a phosphatase in the sample. Depending on the particular structure of the chimeric phosphorylation indicator as disclosed herein, FRET or LRET can be increased or decreased due to phosphorylation of the indicator by a kinase, and, likewise, can be increased or decreased due to phosphorylation of the indicator by a phosphatase. A change in FRET or LRET can be determined by monitoring the emission spectrum of the acceptor. Genetically encoded fluorescent reporters for protein kinase C (PKC) activity are provided herein that reversibly respond to stimuli activating PKC. Phosphorylation of the reporter expressed in mammalian cells causes changes in fluorescence resonance energy transfer (FRET), which may be used, for example, to monitor the activity of PKC by real time imaging of phosphorylation resulting from PKC activation.

In another embodiment, a method for detecting a kinase or phosphatase in a sample is performed by contacting the sample with a chimeric phosphorylatable indicator containing a phosphorylatable polypeptide and a fluorescent protein, determining a fluorescence property in the sample, wherein the presence of kinase or phosphatase activity in the sample results in a change in the fluorescence property as compared to the fluorescent property in the absence of a kinase or phosphatase activity, thereby detecting the kinase or phosphatase in the sample. The chimeric phosphorylation indicator can contain a phosphorylatable polypeptide that includes an N-terminal portion and a C-terminal portion, such that the fluorescent protein is operatively inserted between the N-terminal portion and C-terminal portion of the phosphorylatable polypeptide; or the chimeric phosphorylation indicator can contain a phosphoaminoacid binding domain operatively linked to a phosphorylatable polypeptide, which is operatively inserted between an N-terminal portion and a C-terminal portion of the fluorescent protein. Such a fluorescent protein may be a non-oligomerizing fluorescent protein, or other fluorescent protein.

The sample to be examined for kinase activity can be any sample, including, for example, a sample containing a synthetic product to be examined for kinase or phosphatase activity. In one embodiment, the sample is a biological sample, which can be cell, tissue or organ sample, or an extract of such a sample. In another embodiment, the method is performed on an intact cell, which can be in cell culture or can be in a tissue sample. For such a method, the chimeric phosphorylatable indicator can contain a targeting sequence such as a cell compartmentalization domain that can target the chimeric phosphorylatable indicator to a membrane (e.g., cell membrane or an internal membrane), cytosol, endoplasmic reticulum, mitochondrial matrix, chloroplast lumen, medial trans-Golgi cisternae, a lumen of a lysosome, or a lumen of an endosome. A membrane targeting domain can be a particularly useful to target the chimeric phosphorylation indicators to or near to a cell membrane. A membrane translocating domain can be a particularly useful cell compartmentalization domain is a membrane translocating domain, which can facilitate translocation of the chimeric phosphorylation indicator into an intact cell.

The phosphorylatable polypeptide in a chimeric phosphorylation indicator comprising a fluorescent protein and a phosphorylatable polypeptide can be unphosphorylated or phosphorylated at an amino acid position specific for a kinase or a phosphatase, depending on whether the method is for detecting a kinase or phosphatase. A method of the invention also can be used to detect an absence of kinase or phosphatase activity in the sample, for example, due to the presence of a kinase inhibitor or phosphatase inhibitor.

The present invention relates to a chimeric phosphorylation indicator, which contains, in operative linkage, a donor molecule, a phosphorylatable domain, a phosphoaminoacid binding domain, and an acceptor molecule, wherein the phosphoaminoacid binding domain specifically binds to a phosphoaminoacid when present in the phosphorylatable domain, the donor molecule and the acceptor molecule exhibit a detectable resonance energy transfer when the donor is excited, and the phosphorylatable domain and phosphoaminoacid binding domain do not substantially emit light to excite the acceptor. The donor molecule or the acceptor or both can be a fluorescent protein, such as, e.g., a non-oligomerizing fluorescent protein, or a luminescent molecule, or a combination thereof. In one embodiment, each of the donor molecule and the acceptor molecule is a fluorescent protein, such as, e.g., a non-oligomerizing fluorescent protein. In another embodiment, one of the donor or acceptor molecule is a luminescent molecule and the other is a fluorescent protein, such as, e.g., a non-oligomerizing fluorescent protein. In a third embodiment, each of the donor molecule and acceptor molecule is a luminescent molecule.

A luminescent molecule useful in a chimeric phosphorylation indicator can be, for example, a lanthanide, which can be in the form of a chelate, including a lanthanide complex containing the chelate. Thus, the luminescent molecule can be a terbium ion ($Tb^{3+}$) chelate, for example, a chelate of $Tb^{3+}$ and triethylenetetraamine hexaacetic acid (TTHA), and can further include carbostyril 124 operatively linked to the $Tb^{3+}$ chelate. Where the chimeric phosphorylation indicator is to be contacted with a cell, for example, to detect the presence of a kinase or phosphatase in the cell, the luminescent molecule can further include a membrane translocating domain such as that set forth as SEQ ID NO:18. Such a membrane translocating domain or other molecule to be linked to the luminescent molecule can be operatively linked using, for example, a tetracysteine motif such as that set forth in SEQ ID NO:17.

The phosphorylatable domain in a chimeric phosphorylation indicator of the invention can be any molecule that can be phosphorylated by a specific kinase, for example, a serine/threonine kinase, a tyrosine kinase, or PKC, or that can contain a phosphate group and can be dephosphorylated by a specific phosphatase. Thus, the phosphorylatable domain can be a synthetic peptide, a peptide portion of a naturally-occurring kinase or phosphatase substrate, a peptidomimetic, a polynucleotide, or the like. By way of example, a serine/threonine kinase domain can include an amino acid sequence as that set forth in SEQ ID NO:20 or SEQ ID NO:32, and a tyrosine kinase phosphorylatable domain can include an amino acid sequence as that set forth in SEQ ID NO:23 or SEQ ID NO:25. Another example of a serine/threonine kinase domain is a PKC phosphorylatable domain.

The present invention also relates to a method for detecting a kinase inhibitor or phosphatase inhibitor. Such a method can be performed, for example, by determining a first fluorescence property of a chimeric phosphorylatable indicator in the presence of a kinase or a phosphatase, contacting the chimeric phosphorylatable indicator with a composition suspected of being a kinase inhibitor or a phosphatase inhibitor, determining a second fluorescence property of a chimeric phosphorylatable indicator in the presence of the composition, wherein a difference in the first fluorescence property and second fluorescence property identifies the composition as a kinase inhibitor or phosphatase inhibitor. Such a method is particularly adaptable to high throughput screening methods and, therefore, provides a means to screen libraries of compounds to identify a composition that acts as a kinase inhibitor or a phosphatase inhibitor. Accordingly, the present invention also provides a kinase inhibitor or a phosphatase inhibitor identified by such method.

BRIEF DESCRIPTION OF THE DRAWINGS

FIG. 1A illustrates a CFP-PAABD-substrate-YFP chimeric reporter protein, in which phosphorylation of the substrate can increase FRET.

FIG. 1B illustrates a CFP-substrate-YFP-PAABD chimeric reporter protein, in which phosphorylation can decrease FRET.

FIG. 1C illustrates a YFP(1-144)-peptide-PAABD-YFP (146-238) chimeric reporter protein, in which phosphorylation can modulate the YFP protonation state and emission intensity (shown here as an increase).

FIG. 2A shows the SH2 domain from phospholipase C-γ complexed to a phosphopeptide (D-(pY)-IIPLPD; SEQ ID NO:14) from PDGF receptor (Pascal et al., Cell 77:461-472, 1994). This mitten-shaped SH2 domain was the model for the PAABD shown in FIG. 1.

FIG. 2B shows the PTB domain from Shc complexed with a phosphopeptide HIIENPQ-(pY)-F (SEQ ID NO:15) from TrkA (Zhou et al., Nature 378:584-592, 1995).

FIG. 2C shows the 14-3-3% domain complexed with the phosphopeptide ARSH-(pS)-YPA (SEQ ID NO:16; Yaffe et al., Cell 91:961-971, 1997).

FIG. 4A shows GFP fused to X and the coral RFP fused to Y. Proximity of X and Y promotes fluorescence resonance energy transfer (FRET) from GFP to RFP.

FIG. 4B shows a terbium chelate ("$Tb^{3+}$ chelate"), with a carbostyril antenna ("carbostyril"), attached to X via a biarsenical ligand ("biarsenical"), binding to a "tetracysteine motif" fused to or inserted within X. Proximity of X and Y promotes luminescence resonance energy transfer (LRET) from $Tb^{3+}$ to RFP. Detailed structures of the chelate, antenna, and ligand are provided in FIG. 5A (note that they are much smaller (1.4 kDa total) than GFP (27 kDa)). In-pointing and out-pointing arrows are as in FIG. 1.

FIG. 5A provides a detailed structure of the carbostyril 124-$Tb^{3+}$-triethylenetetraaminehexaacetic acid biarsenical ligand (TTHA)-Antennapedia peptide conjugate for intracellular labeling in live cells of proteins engineered to contain a tetracysteine motif (-Cys-Cys-X-X-Cys-Cys-; SEQ ID NO:17; Griffin et al., Science 281:269-272, 1998). The constituent units corresponding to those indicated in FIG. 4B. After passive internalization mediated by the membrane translocating peptide (SEQ ID NO:18), the latter is released by S—S bond cleavage in the reducing environment of the cytosol (Derossi et al., Trends Cell Biol. 8:84-87, 1998). The tetracysteine motif displaces two molecules of 1,2-ethanedithiol, which is membrane-permeant.

FIG. 5B shows the spectral overlap between carbostyril 124-$Tb^{3+}$-TTHA emission (dotted curve, from Li and Selvin, J. Am. Chem. Soc. 117:8132-8138, 1995) and coral RFP excitation and emission (solid and dash-dotted curves, respectively). The spikes in the solid and dash-dotted curves near 560 nm and 580 nm are scattering artifacts. As desirable for LRET, the dotted trace overlaps well with the solid trace, but very little with the dash-dotted trace.

FIGS. 6A and 6B illustrate the ratiometric indicator for visualizing serine/threonine phosphorylation.

FIG. 6A illustrates how FRET between GFPs can report phosphorylation and dephosphorylation. The ECFP(1-227) ("CFP"; amino acids 1 to 227 of SEQ ID NO:6) and citrine ("YFP"; SEQ ID NO:10, except containing a Q69M mutation) are shown as cylinders, reflecting their crystal structures. The phosphoaminoacid binding protein is shown, with a circle inside representing the phosphate-binding site rich in Arg and Lys residues (see FIG. 6B). The kinase/phosphatase substrate peptide domain, including linkers, also is indicated. The smaller circle within the phosphate-binding site (larger circle) represents phosphoaminoacids, as indicated. In-pointing and out-pointing arrows with respect to the GFPs indicate excitation (433 nm) and emission (476 nm) maxima, respectively. Upon phosphorylation by protein kinase, the adjacent phosphoaminoacid binding protein binds to the phosphorylated substrate peptide, which changes the efficiency of FRET between the GFP mutants.

FIG. 6B illustrates the domain structure of the PKA reporter, including, from N-terminus to C-terminus, ECFP(1-227) (amino acids 1 to 227 of SEQ ID NO:6), linker 1 (MH), 14-3-3τ (1-232), linker 2 (SEQ ID NO:19), the kemptide substrate (SEQ ID NO:20), linker 3 (SEQ ID NO:21), and citrine.

FIG. 7A shows, from N-terminus to C-terminus, the enhanced cyan fluorescent protein (CFP) domain, the SH2 domain from Shc, a linker peptide (SEQ ID NO: 22), the substrate domain, including a peptide portion showing the phosphorylation site (SEQ ID NO: 23), and the enhanced yellow fluorescent protein domain (YFP).

FIG. 7B shows, from N-terminus to C-terminus, the enhanced cyan fluorescent protein (CFP) domain, the SH2 domain from c-src, a linker peptide (SEQ ID NO: 24), the substrate domain, including a peptide-portion showing the phosphorylation site (SEQ ID NO:25), and the enhanced yellow fluorescent protein domain (YFP).

FIG. 7C shows, from N-terminus to C-terminus, the enhanced cyan fluorescent protein (CFP) domain, the FHA2 domain from Rad53, a linker peptide (SEQ ID NO:45), the substrate domain, including a peptide-portion showing the phosphorylation site (SEQ ID NO:44), and the enhanced yellow fluorescent protein domain (YFP).

DETAILED DESCRIPTION OF THE INVENTION

Definitions

Figure 1:
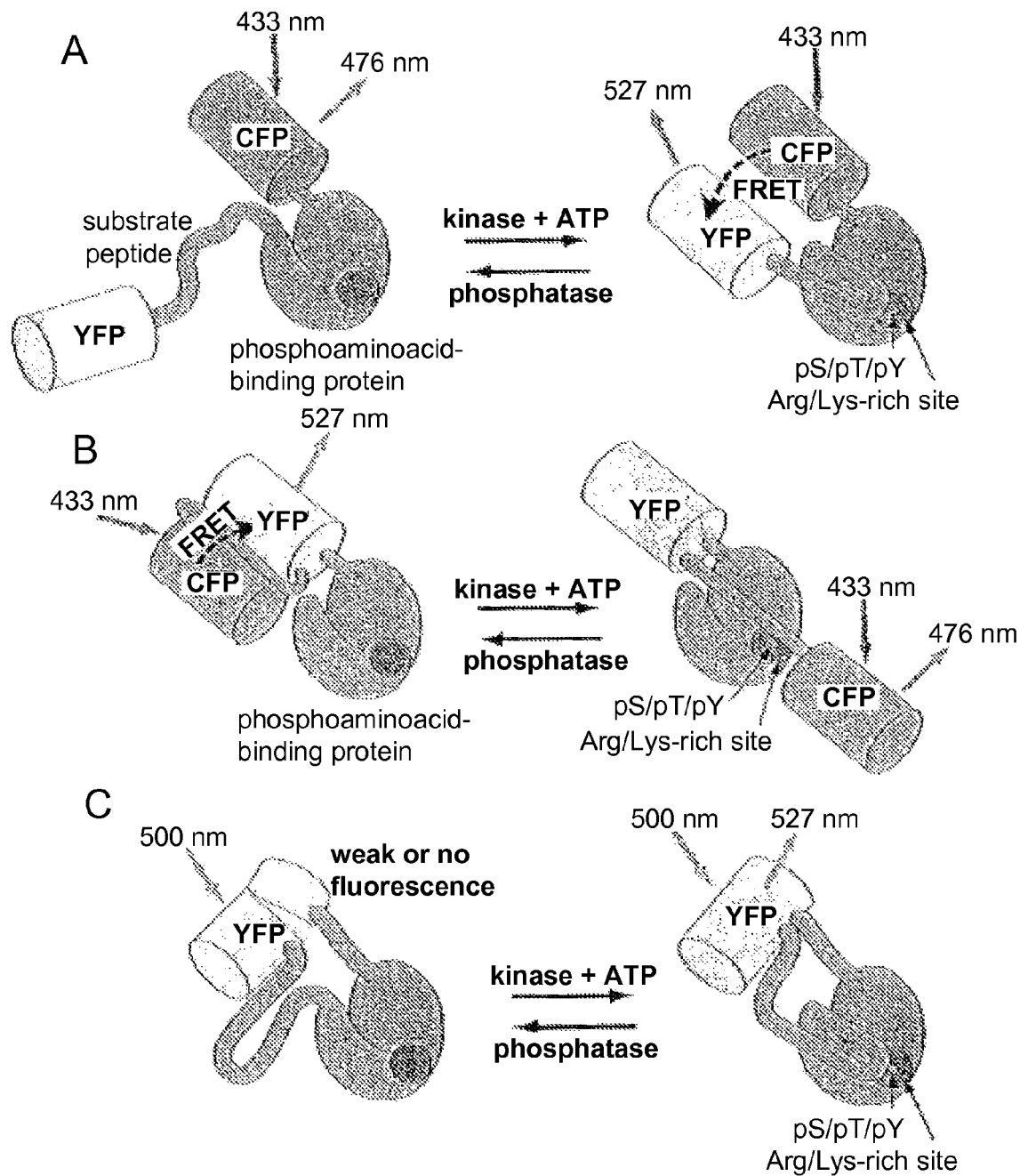
FIGS. 1A to 1C illustrate three generic designs for phosphorylation-specific chimeric reporter proteins, which change fluorescence upon phosphorylation. The fluorescent GFPs, "CFP" and "YFP", are indicated, as are the phosphoaminoacid binding domain (PAABD). The larger circle in the PAABD indicates the phosphate-binding site, which is rich in Arg and Lys residues, and the smaller circle within the larger circle indicates phosphoaminoacids (see FIG. 6B). The kinase/phosphatase substrate peptide also indicated ("substrate peptide"), and includes any spacers present in the construct. In-pointing and out-pointing arrows indicate excitation and emission maxima; respectively, for the GFPs, though the actual spectra are broader than the specific numbers shown in the illustration.

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice the present invention. For purposes of the present invention, the following terms are defined.

The term "nucleic acid molecule" or "polynucleotide" refers to a deoxyribonucleotide or ribonucleotide polymer in either single-stranded or double-stranded form, and, unless specifically indicated otherwise, encompasses polynucleotides containing known analogs of naturally occurring nucleotides that can function in a similar manner as naturally occurring nucleotides. It will be understood that when a nucleic acid molecule is represented by a DNA sequence, this also includes RNA molecules having the corresponding RNA sequence in which "U" replaces "T."

The term "recombinant nucleic acid molecule" refers to a non-naturally occurring nucleic acid molecule containing two or more linked polynucleotide sequences. A recombinant nucleic acid molecule can be produced by recombination methods, particularly genetic engineering techniques, or can be produced by a chemical synthesis method. A recombinant nucleic acid molecule can encode a fusion protein, for example, a chimeric phosphorylation indicator of the invention linked to a polypeptide of interest such as a cell compartmentalization domain. The term "recombinant host cell" refers to a cell that contains a recombinant nucleic acid molecule. As such, a recombinant host cell can express a polypeptide from a "gene" that is not found within the native (non-recombinant) form of the cell.

Reference to a polynucleotide "encoding" a polypeptide means that, upon transcription of the polynucleotide and translation of the mRNA produced therefrom, a polypeptide is produced. The encoding polynucleotide is considered to include both the coding strand, whose nucleotide sequence is identical to an mRNA, as well as its complementary strand. It will be recognized that such an encoding polynucleotide is considered to include degenerate nucleotide sequences, which encode the same amino acid residues. Nucleotide sequences encoding a polypeptide can include polynucleotides containing introns as well as the encoding exons.

The term "expression control sequence" refers to a nucleotide sequence that regulates the transcription or translation of a polynucleotide or the localization of a polypeptide to which to which it is operatively linked. Expression control sequences are "operatively linked" when the expression control sequence controls or regulates the transcription and, as appropriate, translation of the nucleotide sequence (i.e., a transcription or translation regulatory element, respectively), or localization of an encoded polypeptide to a specific compartment of a cell. Thus, an expression control sequence can be a promoter, enhancer, transcription terminator, a start codon (ATG), a splicing signal for intron excision and maintenance of the correct reading frame, a STOP codon, a ribosome binding site, or a sequence that targets a polypeptide to a particular location, for example, a cell compartmentalization signal, which can target a polypeptide to the cytosol, nucleus, plasma membrane, endoplasmic reticulum, mitochondrial membrane or matrix, chloroplast membrane or lumen, medial trans-Golgi cisternae, or a lysosome or endosome, or is a membrane translocating peptide, which allows a molecule operatively linked thereto to cross a cell membrane and enter an intact cell. Cell compartmentalization domains are well known in the art and include, for example, a peptide containing amino acid residues 1 to 81 of human type II membrane-anchored protein galactosyltransferase, or amino acid residues 1 to 12 of the presequence of subunit IV of cytochrome c oxidase (see, also, Hancock et al., EMBO J. 10:4033-4039, 1991; Buss et al., Mol. Cell. Biol. 8:3960-3963, 1988; U.S. Pat. No. 5,776,689).

The term "operatively linked" or "in operative linkage" also is used herein to indicate that the components of a chimeric phosphorylation indicator are joined together such that each component maintains its function relevant to phosphorylation detection, or can be induced to express its function. For example, the phosphorylatable domain is operatively linked to the PAABD such that, when an amino acid residue of the phosphorylatable domain is phosphorylated, the PAABD can bind to the phosphoaminoacid. Similarly, the donor molecule and acceptor molecule are in operative linkage, through the phosphorylatable domain and PAABD, as well as any linker molecules, such that, upon excitation of the donor molecule, FRET can occur so as to excite the acceptor, which, in response, fluoresces. Methods for operatively linking the components of a chimeric phosphorylation indicator, including the use of linker and spacer peptides and the like, can be determined rationally based, for example, on crystallographic information, can be extrapolated from the methods and compositions disclosed herein, or can be determined empirically. A linker molecule may be, for example, a polypeptide, and be capable of forming an operative linkage between other moieties, such as a donor and an acceptor. Linker polypeptides may have lengths, for example, of between about 3 amino acid residues to about 50 amino acid residues, or between about 4 amino acid residues to about 30 amino acid residues, or between about 5 amino acid residues to about 15 amino acid residues.

The term "operatively inserted" is used similarly herein to refer to the introduction of a first polypeptide into a second polypeptide, at a position between the N-terminus and C-terminus of the second polypeptide, such that each of the polypeptides maintains its original function or can be induced to express its original function. For example, where a phosphorylatable polypeptide is operatively inserted into a fluorescent protein, the phosphorylatable polypeptide maintains its ability to act as a substrate for a phosphatase or kinase, and the fluorescent protein maintains its characteristic fluorescence property, although the fluorescence property may not be exhibited due, for example, to the phosphorylation state of the phosphorylatable polypeptide.

The term "oligomer" refers to a complex formed by the specific interaction of two or more polypeptides. A "specific interaction" or "specific association" is one that is relatively stable under specified conditions, for example, physiologic conditions. Reference to a "propensity" of proteins to oligomerize indicates that the proteins can form dimers, trimers, tetramers, or the like under specified conditions. Generally, fluorescent proteins such as GFPs and DsRed have a propensity to oligomerize under physiologic conditions although, as disclosed herein, fluorescent proteins also can oligomerize, for example, under pH conditions other than physiologic conditions. Some fluorescent proteins have a reduced propensity to oligomerize as compared to a reference fluorescence protein, such as a naturally occurring amino acid sequence or to a particular synthetic amino acid sequence. Such fluorescent proteins may be termed "non-oligomerizing proteins" or "non-oligomerizing fluorescent proteins." Non-oligomerizing fluorescent proteins may be variants of a naturally occurring, or a synthetic, fluorescent protein, and have a mutation (e.g., an insertion, deletion or substitution) in their amino acid sequence as compared to the naturally occurring or to the particular synthetic amino acid sequence.

The term "probe" refers to a substance that specifically binds to another substance (a "target"). Probes include, for example, antibodies, polynucleotides, receptors and their ligands, and generally can be labeled so as to provide a means to identify or isolate a molecule to which the probe has specifically bound. The term "label" refers to a composition that is detectable with or without the instrumentation, for example, by visual inspection, spectroscopy, or a photochemical, biochemical, immunochemical or chemical reaction. Useful labels include, for example, phosphorus-32, a fluorescent dye, a fluorescent protein, an electron-dense reagent, an enzymes (such as is commonly used in an ELISA), a small molecule such as biotin, digoxigenin, or other haptens or peptide for which an antiserum or antibody, which can be a monoclonal antibody, is available. It will be recognized that a non-oligomerizing fluorescent protein of the invention, which is itself a detectable protein, can nevertheless be labeled so as to be detectable by a means other than its own fluorescence, for example, by incorporating a radionuclide label or a peptide tag into the protein so as to facilitate, for example, identification of the protein during its expression and isolation of the expressed protein, respectively. A label useful for purposes of the present invention generally generates a measurable signal such as a radioactive signal, fluorescent light, enzyme activity, and the like, either of which can be used, for example, to quantitate the amount of the non-oligomerizing fluorescent protein in a sample.

The term "nucleic acid probe" refers to a polynucleotide that binds to a specific nucleotide sequence or sub-sequence of a second (target) nucleic acid molecule. A nucleic acid probe generally is a polynucleotide that binds to the target nucleic acid molecule through complementary base pairing. It will be understood that a nucleic acid probe can specifically bind a target sequence that has less than complete complementarity with the probe sequence, and that the specificity of binding will depend, in part, upon the stringency of the hybridization conditions. A nucleic acid probes can be labeled as with a radionuclide, a chromophore, a lumiphore, a chromogen, a fluorescent protein, or a small molecule such as biotin, which itself can be bound, for example, by a streptavidin complex, thus providing a means to isolate the probe, including a target nucleic acid molecule specifically bound by the probe. By assaying for the presence or absence of the probe, one can detect the presence or absence of the target sequence or sub-sequence. The term "labeled nucleic acid probe" refers to a nucleic acid probe that is bound, either directly or through a linker molecule, and covalently or through a stable non-covalent bond such as an ionic, van der Waals or hydrogen bond, to a label such that the presence of the probe can be identified by detecting the presence of the label bound to the probe.

The term "polypeptide" or "protein" refers to a polymer of two or more amino acid residues. The terms apply to amino acid polymers in which one or more amino acid residue is an artificial chemical analogue of a corresponding naturally occurring amino acid, as well as to naturally occurring amino acid polymers. The term "recombinant protein" refers to a protein that is produced by expression of a nucleotide sequence encoding the amino acid sequence of the protein from a recombinant DNA molecule.

The term "isolated" or "purified" refers to a material that is substantially or essentially free from components that normally accompany the material in its native state in nature. Purity or homogeneity generally are determined using analytical chemistry techniques such as polyacrylamide gel electrophoresis, high performance liquid chromatography, and the like. A polynucleotide or a polypeptide is considered to be isolated when it is the predominant species present in a preparation. Generally, an isolated protein or nucleic acid molecule represents greater than 80% of the macromolecular species present in a preparation, often represents greater than 90% of all macromolecular species present, usually represents greater than 95%, of the macromolecular species, and, in particular, is a polypeptide or polynucleotide that purified to essential homogeneity such that it is the only species detected when examined using conventional methods for determining purity of such a molecule.

The term "antibody" refers to a polypeptide substantially encoded by an immunoglobulin gene or immunoglobulin genes, or antigen-binding fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Antibodies exist as intact immunoglobulins and as well characterized antigen-binding fragments of an antibody, which can be produced by digestion with a peptidase or can using recombinant DNA methods. Such antigen-binding fragments of an antibody include, for example, Fv, Fab' and F(ab)'$_2$ fragments. The term "antibody," as used herein, includes antibody fragments either produced by the modification of whole antibodies or those synthesized de novo using recombinant DNA methodologies. As such, the present invention also provides an antibody or antigen-binding fragment thereof that specifically binds a chimeric phosphorylation indicator of the invention. Preferably, an antibody of the invention does not specifically bind the individual components that comprise the chimeric indicator, except when the components are part of the chimeric phosphorylation indicator. The term "immunoassay" refers to an assay that utilizes an antibody to specifically bind an analyte. An immunoassay is characterized by the use of specific binding properties of a particular antibody to isolate, target, and/or quantify the analyte.

The term "identical," when used in reference to two or more polynucleotide sequences or two or more polypeptide sequences, refers to the residues in the sequences that are the same when aligned for maximum correspondence. When percentage of sequence identity is used in reference to a polypeptide, it is recognized that one or more residue positions that are not otherwise identical can differ by a conservative amino acid substitution, in which a first amino acid residue is substituted for another amino acid residue having similar chemical properties such as a similar charge or hydrophobic or hydrophilic character and, therefore, does not change the functional properties of the polypeptide. Where polypeptide sequences differ in conservative substitutions, the percent sequence identity can be adjusted upwards to correct for the conservative nature of the substitution. Such an adjustment can be made using well known methods, for example, scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions can be calculated using any well known algorithm (see, for example, Meyers and Miller, Comp. Appl. Biol. Sci. 4:11-17, 1988; Smith and Waterman, Adv. Appl. Math. 2:482, 1981; Needleman and Wunsch, J. Mol. Biol. 48:443, 1970; Pearson and Lipman, Proc. Natl. Acad. Sci., USA 85:2444 (1988); Higgins and Sharp, Gene 73:237-244, 1988; Higgins and Sharp, CABIOS 5:151-153; 1989; Corpet et al., Nucl. Acids Res. 16:10881-10890, 1988; Huang, et al., Comp. Appl. Biol. Sci. 8:155-165, 1992; Pearson et al., Meth. Mol. Biol., 24:307-331, 1994). Alignment also can be performed by simple visual inspection and manual alignment of sequences.

The term "conservatively modified variation," when used in reference to a particular polynucleotide sequence, refers to different polynucleotide sequences that encode identical or essentially identical amino acid sequences, or where the polynucleotide does not encode an amino acid sequence, to essentially identical sequences. Because of the degeneracy of the genetic code, a large number of functionally identical polynucleotides encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleotide sequence variations are "silent variations," which can be considered a species of "conservatively modified variations." As such, it will be recognized that each polynucleotide sequence disclosed herein as encoding a non-oligomerizing fluorescent protein also describes every possible silent variation. It will also be recognized that each codon in a polynucleotide, except AUG, which is ordinarily the only codon for methionine, and UUG, which is ordinarily the only codon for tryptophan, can be modified to yield a functionally identical molecule by standard techniques. Accordingly, each silent variation of a polynucleotide that does not change the sequence of the encoded polypeptide is implicitly described herein. Furthermore, it will be recognized that individual substitutions, deletions or additions that alter, add or delete a single amino acid or a small percentage of amino acids (typically less than 5%, and generally less than 1%) in an encoded sequence can be considered conservatively modified variations, provided alteration results in the substitution of an amino acid with a chemically similar amino acid. Conservative amino acid substitutions providing functionally similar amino acids are well known in the art, including the following six groups, each of which contains amino acids that are considered conservative substitutes for each another:

1) Alanine (Ala, A), Serine (Ser, S), Threonine (Thr, T);
2) Aspartic acid (Asp, D), Glutamic acid (Glu, E);
3) Asparagine (Asn, N), Glutamine (Gln, Q);
4) Arginine (Arg, R), Lysine (Lys, K);
5) Isoleucine (Ile, I), Leucine (Leu, L), Methionine (Met, M), Valine (Val, V); and
6) Phenylalanine (Phe, F), Tyrosine (Tyr, Y), Tryptophan (Trp, W).

Two or more amino acid sequences or two or more nucleotide sequences are considered to be "substantially identical" or "substantially similar" if the amino acid sequences or the nucleotide sequences share at least 80% sequence identity with each other, or with a reference sequence over a given comparison window. Thus, substantially similar sequences include those having, for example, at least 85% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity. One protein or polypeptide is related to another protein or polypeptide where the proteins are substantially identical or substantially similar. Thus, for example, one protein or polypeptide is related to another protein or polypeptide where the amino acid sequences of the proteins or polypeptides have for example, at least 85% sequence identity. Similarly, two or more proteins or polypeptides may be termed related proteins or polypeptides if they share at least 90% sequence identity. In addition, two or more proteins or polypeptides may be termed related proteins or polypeptides if they share at least 95% sequence identity, or if they share at least 99% sequence identity. Thus, for example, a protein related to a GFP is a protein having an amino acid sequence having at least 85% sequence identity, or at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity, with the amino acid sequence of GFP.

A subject nucleotide sequence is considered "substantially complementary" to a reference nucleotide sequence if the complement of the subject nucleotide sequence is substantially identical to the reference nucleotide sequence. The term "stringent conditions" refers to a temperature and ionic conditions used in a nucleic acid hybridization reaction. Stringent conditions are sequence dependent and are different under different environmental parameters. Generally, stringent conditions are selected to be about 5° C. to 20° C. lower than the thermal melting point (Tm) for the specific sequence at a defined ionic strength and pH. The Tm is the temperature, under defined ionic strength and pH, at which 50% of the target sequence hybridizes to a perfectly matched probe.

The term "allelic variants" refers to polymorphic forms of a gene at a particular genetic locus, as well as cDNAs derived from mRNA transcripts of the genes, and the polypeptides encoded by them. The term "preferred mammalian codon" refers to the subset of codons from among the set of codons encoding an amino acid that are most frequently used in proteins expressed in mammalian cells as chosen from the following list: Gly (GGC, GGG); Glu (GAG); Asp (GAC); Val (GUG, GUC); Ala (GCC, GCU); Ser (AGC, UCC); Lys (AAG); Asn (AAC); Met (AUG); Ile (AUC); Thr (ACC); Trp (UGG); Cys (UGC); Tyr (UAU, UAC); Leu (CUG); Phe (UUC); Arg (CGC, AGG, AGA); Gln (CAG); His (CAC); and Pro (CCC).

Fluorescent molecules are useful in fluorescence resonance energy transfer, FRET, which involves a donor molecule and an acceptor molecule. To optimize the efficiency and detectability of FRET between a donor and acceptor molecule, several factors need to be balanced. The emission spectrum of the donor should overlap as much as possible with the excitation spectrum of the acceptor to maximize the overlap integral. Also, the quantum yield of the donor moiety and the extinction coefficient of the acceptor should be as high as possible to maximize Ro, which represents the distance at which energy transfer efficiency is 50%. However, the excitation spectra of the donor and acceptor should overlap as little as possible so that a wavelength region can be found at which the donor can be excited efficiently without directly exciting the acceptor because fluorescence arising from direct excitation of the acceptor can be difficult to distinguish from fluorescence arising from FRET. Similarly, the emission spectra of the donor and acceptor should overlap as little as possible so that the two emissions can be clearly distinguished. High fluorescence quantum yield of the acceptor moiety is desirable if the emission from the acceptor is to be measured either as the sole readout or as part of an emission ratio. One factor to be considered in choosing the donor and acceptor pair is the efficiency of fluorescence resonance energy transfer between them. The efficiency of FRET between the donor and acceptor is at least 10%, or at least 25%, or at least 50%, preferably at least 75%, more preferably at least 80%, more preferably still at least 85%, even more preferably at least 85%, and more preferably still at least 90%.

The term "fluorescent property" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference in any one of these properties between wild type Aequorea GFP and a spectral variant, or a mutant thereof, is useful. A measurable difference can be determined by determining the amount of any quantitative fluorescent property, e.g., the amount of fluorescence at a particular wavelength, or the integral of fluorescence over the emission spectrum. Determining ratios of excitation amplitude or emission amplitude at two different wavelengths ("excitation amplitude ratioing" and "emission amplitude ratioing", respectively) are particularly advantageous because the ratioing process provides an internal reference and cancels out variations in the absolute brightness of the excitation source, the sensitivity of the detector, and light scattering or quenching by the sample.

As used herein, the term "fluorescent protein" refers to any protein that can fluoresce when excited with an appropriate electromagnetic radiation, except that chemically tagged proteins, wherein the fluorescence is due to the chemical tag, and polypeptides that fluoresce only due to the presence of certain amino acids such as tryptophan or tyrosine, which fluoresce when exposed to ultraviolet light, are not considered fluorescent proteins for purposes of the present invention. In general, a fluorescent protein useful for preparing a composition of the invention or for use in a method of the invention is a protein that derives its fluorescence from autocatalytically forming a chromophore. A fluorescent protein can contain amino acid sequences that are naturally occurring or that have been engineered (i.e., variants or mutants). When used in reference to a fluorescent protein, the term "mutant" or "variant" refers to a protein that is different from a reference fluorescent protein. Aequorea GFP is widely used in cell biology as a protein module that can be fused to host proteins to make the latter fluorescent (Tsien, Ann. Rev. Biochem. 67:509-544, 1998). For example, GFP is commonly used to characterize subcellular localization and trafficking properties of proteins, to which the GFP is fused. For example, a spectral variant of Aequorea GFP can be derived from the naturally occurring GFP by engineering mutations such as amino acid substitutions into the reference GFP protein. For example ECFP (SEQ ID NO: 6) is a spectral variant of GFP that contains substitutions with respect to GFP (compare SEQ ID NOS: 2 and 6). Other spectral variants include, for example, EGFP (SEQ ID NO: 4) and EYFP (SEQ ID NO: 8).

Many cnidarians use green fluorescent proteins as energy transfer acceptors in bioluminescence. The term "green fluorescent protein" is used broadly herein to refer to a protein that fluoresces green light, for example, Aequorea GFP (SEQ ID NO:2). GFPs have been isolated from the Pacific Northwest jellyfish, Aequorea victoria, the sea pansy, Renilla reniformis, and Phialidium gregarium (Ward et al., Photochem. Photobiol. 35:803-808, 1982; Levine et al., Comp. Biochem. Physiol. 72B:77-85, 1982). Similarly, reference is made herein to "red fluorescent proteins", which fluoresce red, "cyan fluorescent proteins," which fluoresce cyan, and the like. RFPs, for example, have been isolated from the coral, Discosoma (Matz et al., supra, 1999).

A variety of Aequorea GFP-related fluorescent proteins having useful excitation and emission spectra have been engineered by modifying the amino acid sequence of a naturally occurring GFP from A. victoria (see Prasher et al., Gene 111:229-233, 1992; Heimet al., Proc. Natl. Acad. Sci., USA 91:12501-12504, 1994; U.S. Ser. No. 08/337,915, filed Nov. 10, 1994; International application PCT/US95/14692). As used herein, reference to a "related fluorescent protein" refers to a fluorescent protein that has a substantially identical amino acid sequence when compared to a reference fluorescent protein. In general, a related fluorescent protein, when compared to the reference fluorescent protein sequence, has a contiguous sequence of at least about 150 amino acids that shares at least about 85% sequence identity with the reference fluorescent protein, and particularly has a contiguous sequence of at least about 200 amino acids that shares at least about 95% sequence identity with the reference fluorescent protein. Thus, reference is made herein to an "Aequorea-related fluorescent protein" or to a "GFP-related fluorescent protein," which is exemplified by the various spectral variants and GFP mutants that have amino acid sequences that are substantially identical to A. Victoria GFP (SEQ ID NO:2), to a "Discosoma-related fluorescent protein" or a "DsRed-related fluorescent related protein," which is exemplified by the various mutants that have amino acid sequences substantially identical to that of DsRed (SEQ ID NO:12), and the like, for example, a Renilla-related fluorescent protein or a Phialidium-related fluorescent protein.

The term "naturally-occurring" is used to refer to a protein, nucleic acid molecule, cell, or other material that occurs in nature. For example, a polypeptide or polynucleotide sequence that is present in an organism, including in a virus. A naturally occurring material can be in its form as it exists in nature, and can be modified by the hand of man such that, for example, is in an isolated form.

The amino acid sequences of GFP variants disclosed herein are numbered so as to correspond to the amino acid sequence of wild-type GFP. The amino acid sequence of all sequences related to GFP is numbered with the first Ser after the initial Met numbered as number 2. For example, the initial two amino acids in the amino acid sequence of wild-type GFP are Met—Ser, so that Met is numbered 1 and Ser is numbered 2. Since the wild-type GFP amino acid sequence serves as a reference sequence for GFP variants, the first Ser is numbered 2 in GFP variants. Thus, even if a Val has been inserted after the initial Met, the Val is numbered 1A and the Ser following the inserted Val is numbered 2, so that the Ser and all subsequent amino acids have amino acid sequence numbers corresponding to the corresponding amino acid of wild-type GFP. The numbering of amino acid variants, including amino acid substitutions, corresponds to that of wild-type GFP, so that, for example, the numbering of a mutation of an amino acid residue corresponding to A206, L221, F223, or a combination thereof of SEQ ID NO:2, when applied with respect to, for example, SEQ ID NO:6 or SEQ ID NO: 10, the initial Ser of SEQ ID NO: 6 or SEQ ID NO: 10 is given the number 2 and all subsequent amino acids in the sequences are numbered sequentially from that number 2.

The term "mutant" or "variant" also is used herein in reference to a fluorescent protein to refer to a fluorescent protein that contains a mutation with respect to a corresponding wild type fluorescent protein. In addition, reference is made herein the a "spectral variant" or "spectral mutant" of a fluorescent protein to indicate a mutant fluorescent protein that has a different fluorescence characteristic with respect to the corresponding reference fluorescent protein (e.g., wild type fluorescent protein or synthetic fluorescence protein). For example, CFP, YFP, ECFP (SEQ ID NO:6), EYFP-V68L/Q69K (SEQ ID NO: 10), mCFP, mYFP and the like are GFP spectral variants. CFP has mutations N146I, M153T, and V163A with respect to SEQ ID NO:2, and YFP has mutations S65G, V68L, Q69K, S72A, and T203Y respect to SEQ ID NO:2 (Tsien, Ann. Rev. Biochem. 67:509-544, 1998).

Some fluorescent proteins have a reduced propensity to oligomerize as compared to a naturally occurring amino acid sequence or to a particular synthetic amino acid sequence. Such fluorescent proteins may be termed "non-oligomerizing proteins" or "non-oligomerizing fluorescent proteins." Non-oligomerizing fluorescent proteins may be variants of a naturally occurring, or a synthetic, fluorescent protein, and have a mutation (e.g., an insertion, deletion or substitution) in their amino acid sequence as compared to the naturally occurring or to the particular synthetic amino acid sequence. For example, variants of GFP having a reduced propensity to oligomerize are termed "monomeric GFP" variants (mGFP) and may be, for example, variants of CFP (mCFP), YFP (mYFP) or other fluorescent proteins related to GFP, having a mutation of an amino acid residue corresponding to A206, L221, F223, or a combination thereof of SEQ ID NO:2, for example, an A206K mutation, an L221K mutation, an F223R mutation, or an L221K and F223R mutation of SEQ ID NO:2; or an A206K mutation, an L221K mutation, an F223R mutation, or an L221K and F223R mutation of SEQ ID NO:6 or SEQ ID NO:10. Similarly, variants of DsRed may have a reduced propensity to oligomerize, and so be termed monomeric RFP (mRFP); such monomeric RFP variants differ from DsRed (SEQ ID NO: 12) in at least one amino acid, including a I125R mutation.

The term "loop domain" refers to an amino acid sequence of an Aequorea-related fluorescent protein that connects the amino acids involved in the secondary structure of the eleven strands of the P-barrel or the central α-helix (residues 56-72). The term "fluorescent protein moiety," when used in reference to a fluorescent protein, refers to a portion of the amino acid sequence of the fluorescent protein that, when the amino acid sequence of the fluorescent protein substrate is optimally aligned with the amino acid sequence of a naturally occurring fluorescent protein, lies between the amino terminal and carboxy terminal amino acids, inclusive, of the amino acid sequence of the naturally occurring fluorescent protein, and comprises a chromophore, which fluoresces upon exposure to an appropriate wavelength of light.

The present invention provides compositions and methods that are generally useful for non-destructively detecting and monitoring protein kinase and phosphatase activities and protein-protein interactions in individual living eukaryotic cells, including mammalian cells, and provide a means to obtain spatial and temporal resolution on the order of a few micrometers and seconds, or better. As disclosed herein, protein kinase and phosphatase activities can be monitored using chimeric substrates (chimeric phosphorylation indicators) that incorporate reporter molecules such as fluorescent proteins or luminescent complexes, whose properties change significantly as a function of the phosphorylation state of the substrate. Protein interactions are detected by resonance energy transfer using fluorescent proteins or lanthanide complexes to label the putative partners. The compositions of the invention are adaptable to modification using methods such as high throughput combinatorial generation and screening techniques and, therefore, readily can be varied to allow monitoring of any desired kinase, phosphatase, or protein interaction. Accordingly, the present invention provides chimeric phosphorylation indicators having various structures as disclosed herein.

In a first embodiment, a chimeric phosphorylation indicator contains, in operative linkage, a donor molecule, a phosphorylatable domain, a phosphoaminoacid binding domain, and an acceptor molecule, wherein the phosphoaminoacid binding domain specifically binds to a phosphoaminoacid when present in the phosphorylatable domain, the donor molecule and the acceptor molecule exhibit a detectable resonance energy transfer when the donor is excited, and the phosphorylatable domain and phosphoaminoacid binding domain do not substantially emit light to excite the acceptor. In a second embodiment, a chimeric phosphorylation indicator contains a phosphorylatable polypeptide and a fluorescent protein. In one aspect of the second embodiment, the phosphorylatable polypeptide comprises an N-terminal portion and a C-terminal portion, and the fluorescent protein is operatively inserted between the N-terminal portion and C-terminal portion of the phosphorylatable polypeptide. In a second aspect of the second embodiment, a phosphoaminoacid binding domain is operatively linked to the phosphorylatable polypeptide, the fluorescent protein comprises an N-terminal portion and a C-terminal portion, and the phosphorylatable polypeptide and operatively linked phosphoaminoacid binding domain is operatively inserted between the N-terminal portion and C-terminal portion of the fluorescent protein. As disclosed herein, the chimeric phosphorylatable indicators of the invention are useful for detecting kinase or phosphatase activity, including in a cell.

For example, a chimeric phosphorylation indicator having features of the invention may comprise, in an orientation from the amino terminus to carboxy terminus, mCFP, a polypeptide linker, an FHA2 phosphoaminoacid binding domain (SEQ ID NO: 57), a PKC substrate phosphorylatable domain comprising (SEQ ID NO: 44) and having an amino end and a carboxy end, said PKC substrate phosphorylatable domain being flanked on both its amino end and its carboxy end by a polypeptide linker, and mYFP.

Protein complementation assays, in which each potential partner is fused to a fragment of a reporter protein, have a much greater dynamic range between fully interacting and noninteracting states because the reporter enzyme fragments are completely dead before reassembly. In addition, in energy transfer methods, the donor and acceptor do not have to touch each other, and the response is instantaneous, fully reversible, and has minimal effect on the kinetics or affinity of the partners' binding. Such assays also can be complementary to spectroscopic techniques as described below.

FRET-based (cameleon-type) strategies is an established strategy for monitoring certain conformational changes in a natural or chimeric proteins. In a FRET-based strategy, the protein of interest is sandwiched between GFP mutants that are capable of FRET (Tsien, Ann. Rev. Biochem. 67:509-544, 1998; Heim, Meth. Enzymol. 302:408-423, 1999). Changes in conformation of the central protein affect the distance or relative orientation between the flanking GFPs, altering the efficiency of FRET, which can readily be imaged in single cells. This strategy has been successfully employed to monitor 1) protease-mediated cleavage of peptide linkers; 2) $Ca^{2+}$-induced binding of calmodulin to peptides from myosin light chain kinase; 3) $Zn^{2+}$ binding to the $Zn^{2+}$ finger from the transcription factor zif268; 4) cAMP-induced dissociation of the regulatory and catalytic subunits of PKA (Zaccolo et al., Nat. Cell Biol. 2:25-29, 2000); 5) cGMP-mediated changes in the conformation of cGMP-dependent protein kinase; and 6) agonist and antagonist binding to nuclear hormone receptors.

As disclosed herein, the FRET strategy has been extended to monitor phosphorylation of a consensus substrate for a kinase (Pearson and Kemp, Meth. Enzymol. 200:62-81, 1991; Kemp and Pearson, Trends Biochem. Sci. 15:342-346, 1990) or phosphatase (Blumenthal, in "Peptides and Protein Phosphorylation" (Kemp, ed; CRC Press 1990), pages 135-143). Such a chimera (FIG. 1A) can include (in order from N-terminus to C-terminus) a GFP mutant such as ECFP, a phosphorylatable domain, a domain capable of binding the phosphoaminoacid in the peptide, and a second GFP mutant such as a pH-insensitive EYFP (see FIG. 1A; see, also, Miyawaki et al., Proc. Natl. Acad. Sci., USA 96:2135-2140, 1999). Phosphorylation of the substrate domain permits the formation of an intramolecular complex with the operatively linked phosphoaminoacid binding domain (PAABD), thereby allowing for an increased FRET between the two fluorescent proteins.

The following abbreviations are used herein: CICR, calcium-induced calcium release; CKAR, C kinase activity reporter; FRET, fluorescence resonance energy transfer; PDBU, phorbol dibutyrate; mCFP, monomeric Cyan Fluorescent Protein; mYFP, monomeric Yellow Fluorescent Protein; MyrPalm, myristoylated and palmitoylated; $PIP_2$, phosphoinositide bisphosphate, PAABD phosphoaminoacid binding domain.

The modular nature of the chimeric phosphorylation indicators facilitates the insertion or substitution of various components, as desired. For example, a Discosoma RFP, DsRed, can be substituted for EYFP(SEQ ID NO:8) and ECFP (SEQ ID NO:6) can be substituted with EGFP in the structure exemplified in FIG. 1A. In addition, the ordering of the donor and acceptor molecules can be interchanged, as can the order of the phosphorylatable domain and the PAABD. In addition, the junctions between the components can be varied using peptide linkers such as those exemplified herein to optimize the responsiveness of the indicators.

A fluorescent protein useful in a constructing a chimeric phosphorylation indicator of the invention can be any fluorescent protein, including, for example, a green fluorescent protein (GFP) such as an Aequorea victoria GFP, a Renilla reniformis GFP, a Phialidium gregarium GFP; a red fluorescent protein (RFP) such as a Discosoma RFP; or a fluorescent protein related to a GFP or an RFP, such as a cyan fluorescent protein (CFP), a yellow fluorescent protein (YFP), an enhanced GFP (EGFP; SEQ ID NO:4), an enhanced CFP (ECFP; SEQ ID NO:6), an enhanced YFP (EYFP; SEQ ID NO:8), a DsRed fluorescent protein (SEQ ID NO:12), citrine, which has an amino acid sequence as set forth in SEQ ID NO:10 except containing a Q69M mutation.

A fluorescent protein useful in a constructing a chimeric phosphorylation indicator of the invention also can be a non-oligomerizing fluorescent protein, in which the propensity of the fluorescent protein to oligomerize is reduced or eliminated. The propensity of a fluorescent protein to oligomerize can be reduced or eliminated by operatively linking a first monomer of a fluorescent protein to at least a second monomer of the fluorescent protein, thereby forming an intramolecular 'dimer', 'trimer' or the like. Such operatively linked homopolymers, which have a substantially reduced ability to form intermolecular oligomers, are exemplified by two monomers of DsRed (SEQ ID NO:12) operatively linked by a peptide linker (SEQ ID NO:13), and by two monomers of a mutant DsRed, which has an amino acid sequence of SEQ ID NO:12, and including an I125R mutation, operatively linked by the peptide linker of SEQ ID NO:13. The propensity of a fluorescent protein to oligomerize also can be reduced or eliminated by introducing one or more mutations into the fluorescent protein. Such mutations are exemplified by a mutation of one or a combination of amino acid residues A206, L221 or F223 of Aequorea GFP (SEQ ID NO:2), or a mutation of another fluorescent protein that corresponds to a mutation of A206, L221 or F223 of SEQ ID NO:2, for example, by the mutations A206K, L221K, F223R of GFP (SEQ ID NO:2), or by the mutations L221K and F223R of ECFP (SEQ ID NO:6) and EYFP-V68L/Q69K (SEQ ID NO:10), which are spectral variants of Aequorea GFP. In addition, spectral variants of GFP, including CFP and YFP and variants thereof have been used to measure the associative properties of host proteins by FRET. FRET between CFP and YFP also has been exploited to create biosensors for calcium ion, and to determine the associative properties of growth factor receptors and G protein-coupled receptors.

The availability of a wide range of variously-colored "spectral mutants" of GFP has provided a potential means for monitoring the associative properties of proteins via FRET. FRET is a quantum mechanical phenomenon of radiationless energy transfer between two fluorophores, that is dependent on the proper spectral overlap of a donor and an acceptor, their distance from each other, and the relative orientation of the chromophores' transition dipoles. Using standard molecular biology technology, fusions can be generated between proteins of interest and spectral mutants of fluorescent proteins, which can then serve effectively as donor and acceptor FRET partners. As indicated above, the GFP spectral mutants have most of the requisite properties to serve as useful FRET partners, except for their homoaffinity and propensity for dimerization. Thus, while the number of FRET-based assays using GFP and its variants is increasing (see, for example, Mitra et al., Gene 173:13-17, 1996; Hartman and Vale, Science 286:782-785, 1999; Zacharias et al., Curr. Opin. Neurobiol. 10:416-421, 2000), the propensity of the GFP-related fluorescent proteins to associate with each other can complicate characterization of protein associations reported by FRET, which should be due solely to interactions of the proteins with no participation from the fluorophore to which they are linked.

A luminescent molecule also can be useful in a chimeric phosphorylation indicator. For example, a lanthanide, which can be in the form of a chelate, including a lanthanide complex containing the chelate. Thus, the luminescent molecule can be a terbium ion ($Tb^{3+}$) chelate, for example, a chelate of $Tb^{3+}$ and triethylenetetraamine hexaacetic acid (TTHA), and can further include carbostyril 124 operatively linked to the $Tb^{3+}$ chelate. Where the chimeric phosphorylation indicator is to be contacted with a cell, for example, to detect the presence of a kinase or phosphatase in the cell, the luminescent molecule can further include a membrane translocating domain such as that set forth as SEQ ID NO:18. Such a membrane translocating domain or other molecule to be linked to the luminescent molecule can be operatively linked using, for example, a tetracysteine motif such as that set forth in SEQ ID NO:17.

Lanthanide chelates are ideal donors for luminescence resonance energy transfer (LRET) to RFPs such as DsRed, and provides four major advantages over conventional FRET (Selvin, IEEE J. Sel. Top. Quant. Electron. 2:1077-1087, 1996; Li and Selvin, J. Am. Chem. Soc. 117:8132-8138, 1995): 1) Because the emission spectrum of lanthanide chelates consists of sharp lines rather than broad peaks, it is easy to separate the donor lanthanide emission from that of any conventional acceptor. 2) Because the LRET-sensitized emission from the acceptor has millisecond kinetics, it can be easily discriminated from directly-excited emission, which has nanosecond kinetics. These two advantages mean that even very low degrees of LRET (i.e., interactions at distances much greater than the Forster distance, Ro) can be detected. 3) The background autofluorescence also has lifetimes in nanoseconds and can likewise be easily eliminated by pulsed excitation and gated detection. Thus, much lower concentrations of probes and labeled proteins should be sufficient. 4) The lanthanide emission is essentially unpolarized, so that the dependences of LRET on the orientations of the donor and acceptor are respectively eliminated and greatly reduced.

A problem with intracellular LRET is that few methods have been established for introducing extremely polar lanthanide chelates into intact cells and site-specifically labeling proteins there. Nonpolar lanthanide chelates such as Tris (3-β-diketonates) are available, but they lack sufficient kinetic stability for use in the presence of intact proteins and cells. Known chelates that are stable enough are extremely hydrophilic polyaminocarboxylates, which have never been demonstrated to cross cell membranes unaided. As such, the lanthanide complexes used in the chimeric phosphorylation indicators of the invention can be conjugated to a membrane translocating peptide such as the Antennapedia hydrophobic signal peptides (Rojas et al., Nat. Biotechnol. 16:370-375, 1998), VP22 of herpes virus (Elliot and O'Hare, Cell 88:223-233, 1997), or the TAT protein, which can mediate import of protein multimers and large polyanions such as antisense nucleic acids of at least 55 bases (Derossi et al., Trends Cell Biol. 8:84-87, 1998).

Figure 5A:
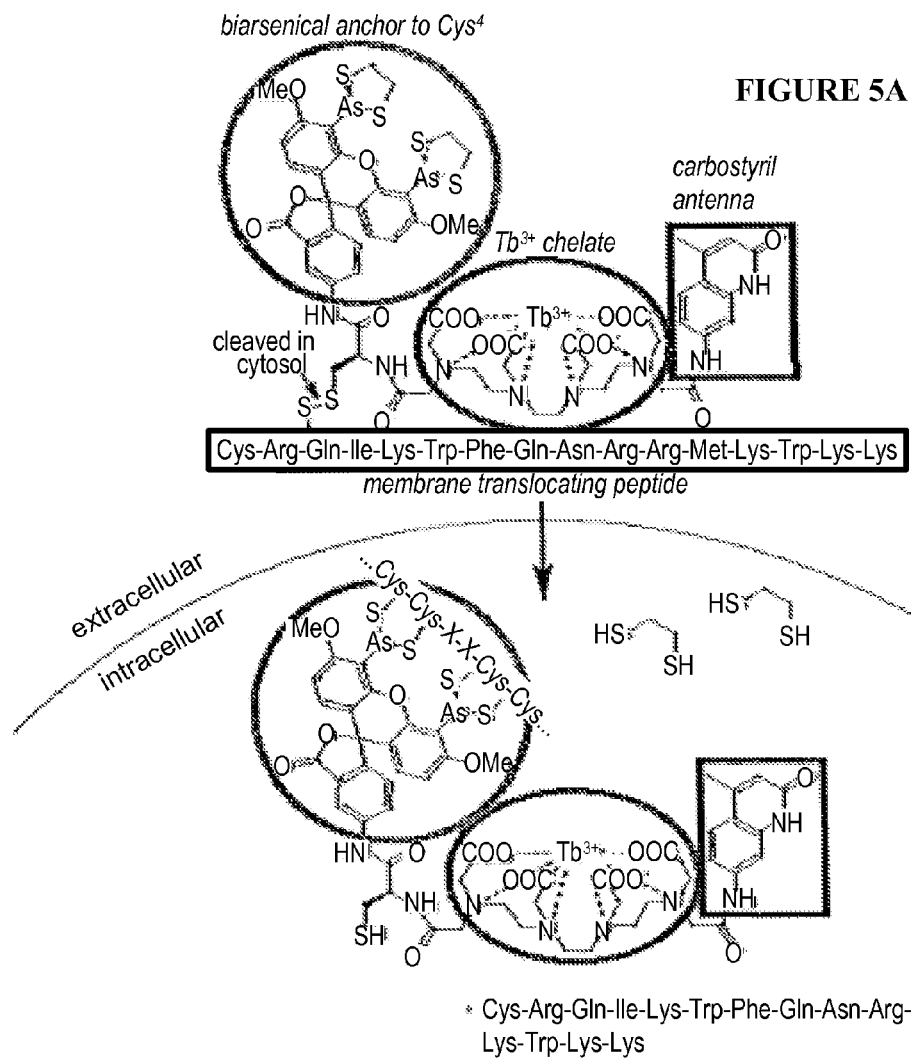
FIGS. 5A and 5B illustrates labeling of live cells using an engineered construct.

The site-specific attachment of the lanthanide chelates to recombinant proteins in intact cells ca be accomplished by linking the lanthanide complex to a biarsenical reagent, which can selectively find and bind a particular tetracysteine motif engineered into a host protein (Griffin et al., Science 281:269-272, 1998). Such a structure is exemplified in FIG. 5A, wherein one end of a $Tb^{3+}$ chelate is attached to the sensitizer or antenna chromophore, e.g., a carbostyril dye (Li and Selvin, supra, 1995), and the other end is attached to the biarsenical reagent and the membrane-translocating peptide via the simplest heterotrifunctional linker, L-cysteine. The biarsenical reagent is not a fluorescent dye, as previously described, so that it does not quench or interfere with the sensitizer or $Tb^{3+}$, and such that the fluorescein moiety is methylated twice to force it into the colorless spiro form. The linkage to the membrane-translocating peptide (in this case penetratin-1 from Antennapedia; Derossi et al., supra, 1998) is via a disulfide bond, which will be cleaved in the reducing environment of the cytosol. Thus the translocating peptide will be discarded before the biarsenical unit attaches the $Tb^{3+}$ complex to the tetracysteine-containing host protein.

Figure 5B:
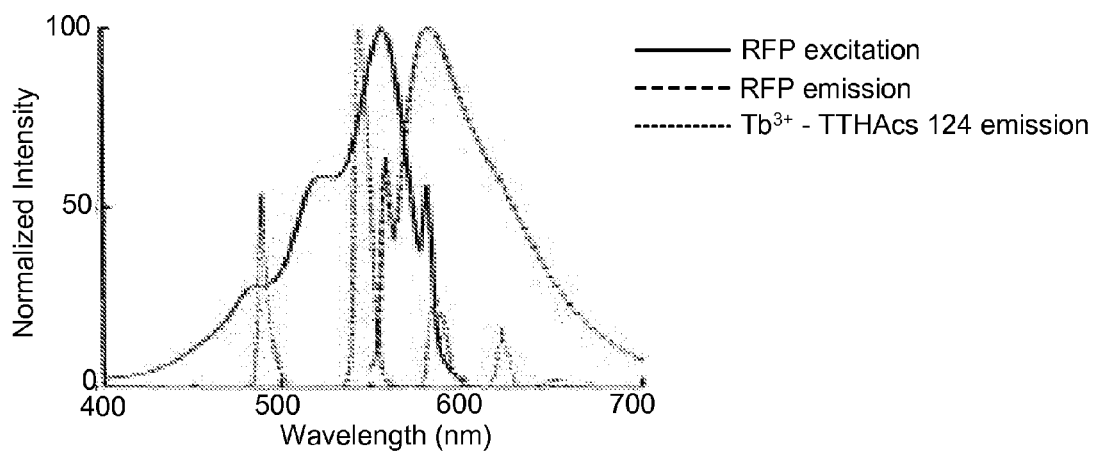

DsRed or a mutant thereof can be an acceptor molecule for LRET from the $Tb^{3+}$ chelate, as the spectral overlap between $Tb^{3+}$ emission and the RFP excitation spectrum is very good (see FIG. 5B). The $Tb^{3+}$ chelate is excited via the carbostyril antenna either with a pulsed nitrogen laser at 337 nm or a mercury-xenon flashlamp at 365 nm. Emissions from both the $Tb^{3+}$ donor and the RFP acceptor are collected in time-resolved manner, which is easy because the relevant time scale is milliseconds. If there is a significant amount of $Tb^{3+}$ donor very far from the RFP acceptor, because either the donor has not found its target protein or the latter is not bound to its partner bearing the RFP, the corresponding emission will have a very long lifetime characteristic of free $Tb^{3+}$ complex. When the $Tb^{3+}$ complex and the RFP are associated, the lifetime of the $Tb^{3+}$ complex is somewhat shortened, whereas the RFP develops a component of similar lifetime. Both components can be quantified, as they are easily separated due to the narrow emission lineshape of the $Tb^{3+}$.

The phosphorylatable domain in a chimeric phosphorylation indicator of the invention can be any molecule that can be phosphorylated by a specific kinase, for example, a serine/threonine kinase or a tyrosine kinase, or that can contain a phosphate group and can be dephosphorylated by a specific phosphatase. Thus, the phosphorylatable domain can be a synthetic peptide, a peptide portion of a naturally-occurring kinase or phosphatase substrate, a peptidomimetic, a polynucleotide, or the like. By way of example, a serine/threonine kinase domain can include an amino acid sequence as that set forth in SEQ ID NO:20 or SEQ ID NO:32, and a tyrosine kinase phosphorylatable domain can include an amino acid sequence as that set forth in SEQ ID NO:23 or SEQ ID NO:25. In preferred embodiments, the phosphorylatable domain contains a PKC substrate, such as, for example, SEQ ID NO: 44, or any one of SEQ ID NOs: 46-55.

The phosphoaminoacid binding domain (PAABD) in a chimeric phosphorylation indicator of the invention can be an PAABD that specifically binds the particular phosphoaminoacid that is present in the indicator or that can be formed due to phosphorylation of the indicator by a kinase. For example, where the phosphorylatable domain is a serine/threonine kinase domain, the phosphoaminoacid binding domain is selected such that it can bind a phosphoserine or phosphoserine or both, for example, the 14-3-3% (1-232) peptide. Where the phosphorylatable domain is a tyrosine kinase domain, the phosphoaminoacid binding domain is selected such that it can bind a phosphotyrosine, for example, a Src homology domain 2 (SH2). In preferred embodiments, where he phosphorylatable domain is a PKC phosphorylatable domain, the phosphoaminoacid binding domain may be an FHA1 or an FHA2 domain (Durocher et al., FEBS Letters 513:58-66 (2002)).

Figure 2:
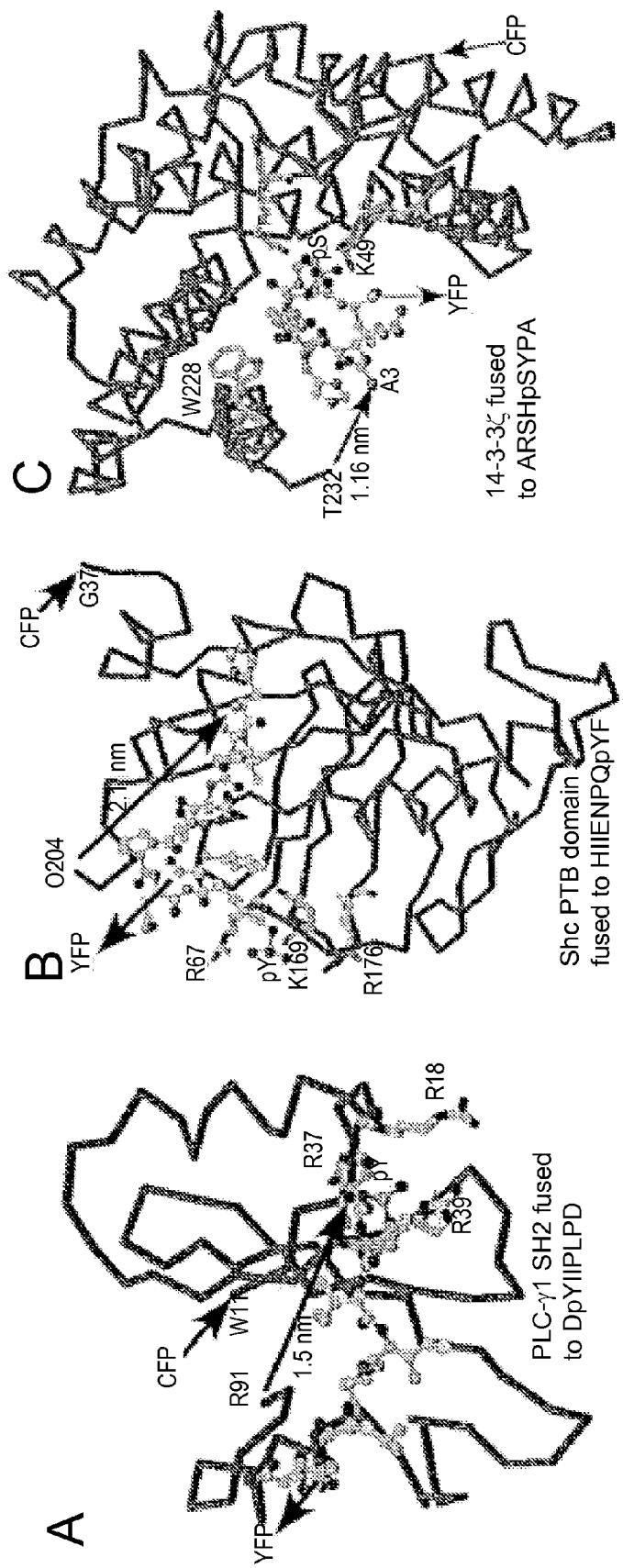
FIGS. 2A to 2C show the structures of various phosphoaminoacid-binding domains complexed to phosphorylated peptides, fused together and bracketed by CFP and YFP to form chimeric indicators as illustrated in FIG. 1A. The dark gray lines represent the protein, with a few key residues involved in binding the peptide shown in stick form, and the phosphopeptide shown in ball-and-stick representation. Heavy arrows indicate linkers that can connect the protein to the peptide or either of them to CFP or YFP (the arrow direction indicates amino to carboxy). The required length in real space of the linker between protein and peptide is indicated. By rearrangement of these linkers (not shown), indicators of the generic structures illustrated in FIGS. 1B and 1C can be constructed analogously.

The SH2 or PTB domains, which bind phosphotyrosine in certain contexts, are the best known and most well understood PAABDs. For example, the NMR structure of an SH2 domain from phospholipase-C-complexed with a phosphopeptide from the PDGF receptor (Pascal and Singer, supra, 1994) suggests these two modules can be fused and sandwiched between a donor and acceptor molecule such as CFP and YFP (see FIG. 2A). Similarly, the structure of a PTB domain from She binding a partner peptide from TrkA (Zhou et al., supra, 1995) indicates that these elements also can be used in a chimeric phosphorylation indicator (see FIG. 2B).

Phosphoserine/phosphothreonine binding domains also have been described, including those of the 14-3-3 proteins. For example, 14-3-3ξ recognizes a consensus sequence R(R/K)(F/R/S/N)(R/H/K) pSer (W/Y/F/L)P (SEQ ID NO:42; Yaffe et al., supra, 1997) that can encompass consensus sites for several important protein kinases such as PKA, PKG, and PKC (Pearson and Kemp, supra, 1991; Kemp and Pearson, supra, 1990). FIG. 2C exemplifies of how kinase activity can be reported using a chimeric phosphorylatable indicator comprising a 14-3-3 protein fused to a domain that is phosphorylatable on a Ser residue.

As disclosed herein, PAABDs also can be identified, for example, by screening phage display libraries using binding to immobilized phosphoaminoacids for affinity selection, or can be evolved from known orthophosphate-binding or sulfate-binding proteins, or from phosphatases by reduction of their catalytic activity. A simple example of the latter approach was the replacement of a catalytic aspartate residue in the tyrosine phosphatase, PTP1B, thus converting it into a "substrate-trap", i.e., a high-affinity binder of phosphotyrosine-containing peptides with a very slow hydrolytic rate (Flint et al., Proc. Natl. Acad. Sci., USA 94:1680-1685, 1997). It should be recognized that a small residual phosphatase activity can be quite beneficial because it can provide a backup mechanism to gradually reset the chimeric phosphorylation indicator back to the nonphosphorylated state, if it is not a substrate for an endogenous phosphatase.

As disclosed herein, FRET can increase or decrease upon phosphorylation or dephosphorylation of a chimeric phosphorylation indicator. For example, using chimeras of GFP-CaM binding peptide-BFP-permuted CaM, FRET from BFP to GFP was strong in the absence of $Ca^{2+}$, presumably because the CaM-binding peptide was flexible enough to allow the two fluorescent proteins to dimerize, whereas, upon elevation of $Ca^{2+}$, dimerization and FRET were disrupted, perhaps because $(Ca^{2+})_4$-CaM binding forced the peptide into a more extended conformation (Perschini et al., Cell Calcium 22:209-216, 1997). As such, substitution of the CaM-binding peptide and CaM by a phosphorylatable domain and a PAABD can be used to generate sensors in which kinase (or phosphatase) activity decreases FRET (see FIG. 1B), the having an opposite response from the cameleon-type indicators described above (see, also, FIG. 1A). Similarly, the connectivity of the spacers in the structures shown in FIG. 2 can be modified to generate such Perschini-type chimeric phosphorylatable indicators.

The present invention also provides a chimeric phosphorylation indicator containing a phosphorylatable polypeptide and a fluorescent protein. These indicators were modeled on chimeras in which a CaM or a Zn-finger motif was inserted in place of Y145 of EYFP, whereupon binding of $Ca^{2+}$ or $Zn^{2+}$ enhanced the fluorescence by 7 or 1.7-fold respectively (Baird et al., Proc. Natl. Acad. Sci., USA 96:11241-11246, 1999). A GFP with β-lactamase inserted between residues 172 and 173 increased fluorescence-1.5 fold upon addition of β-lactamase-inhibitory protein (Selvin, supra, 1996). The application of this strategy to phosphorylation detection is exemplified in FIG. 1C, wherein a phosphorylatable peptide and PAABD are inserted within position 145 of EYFP. a conformational change in the insert can modulate the fluorescence efficiency of the EYFP reporter. This strategy utilizes only one fluorescent protein, and can give very large responses, including changes in pH-sensitive fluorescence at one wavelength rather than a change in ratio of emissions at two wavelengths.

Accordingly, in one embodiment of a chimeric phosphorylation indicator containing a phosphorylatable polypeptide and a fluorescent protein, a phosphoaminoacid binding domain is operatively linked to the phosphorylatable polypeptide, the fluorescent protein comprises an N-terminal portion and a C-terminal portion, and the phosphorylatable polypeptide and operatively linked phosphoaminoacid binding domain is operatively inserted between the N-terminal portion and C-terminal portion of the fluorescent protein. The fluorescent protein can be any fluorescent protein, including, a GFP, an RFP, or a fluorescent protein related to a GFP or an RFP, and is exemplified by an EYFP in which the phosphorylatable polypeptide and operatively linked phosphoaminoacid binding domain is operatively inserted between amino acid positions 145 and 146 of the EYFP or is substituted for amino acid 145. In preferred embodiments, the fluoreacent protein may be a YFP or a CFP, and is preferably a CFP and a YFP, more preferably a monomeric CFP (mCFP) and a monomeric YFP (mYFP) (Zacharias et al., Science 296:913-916 (2002)).

Figure 3:
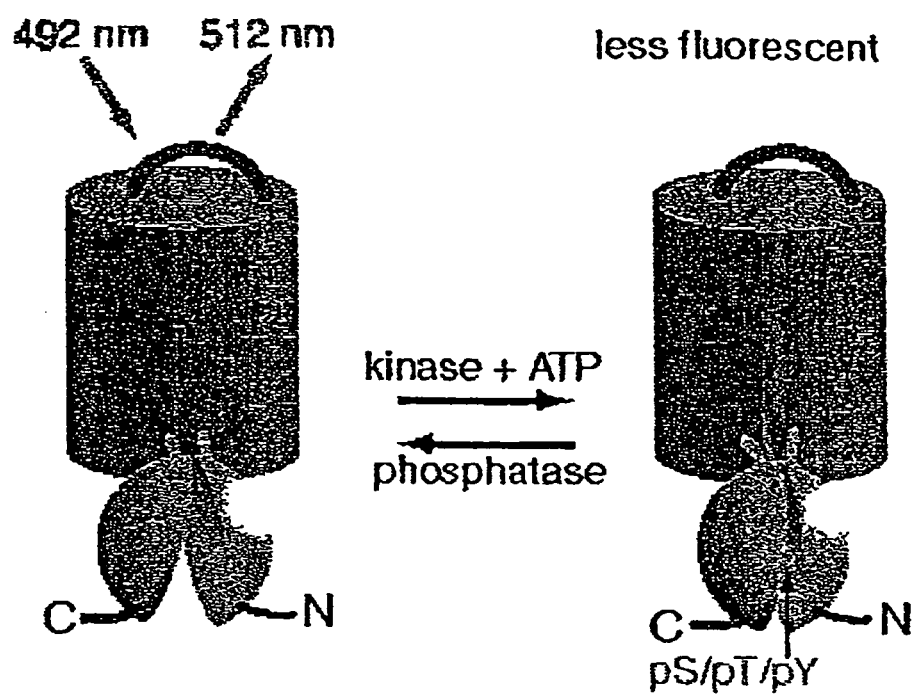
FIG. 3 provides a schematic structure of a circularly permuted GFP (cpGFP; cylinder) inserted within a protein (clamshell) whose conformation changes upon phosphorylation. The tube (arc) at the top of the cpGFP cylinder indicates a spacer linking the original N-terminus and C-terminus of GFP. Linkers connecting the new N-terminus and C-terminus of the cpGFP to the insertion site within the phosphorylatable protein are indicated by tubes. The N-terminus and C-terminus of the chimera are the same as those of the phosphorylatable protein alone, and also are indicated by tubes. The circle in the protein indicates the phosphorylated amino acid. In this example, phosphorylation favors a closed conformation, which pries open a cleft in the cpGFP, diminishing cpGFP fluorescence.
Figure 4:
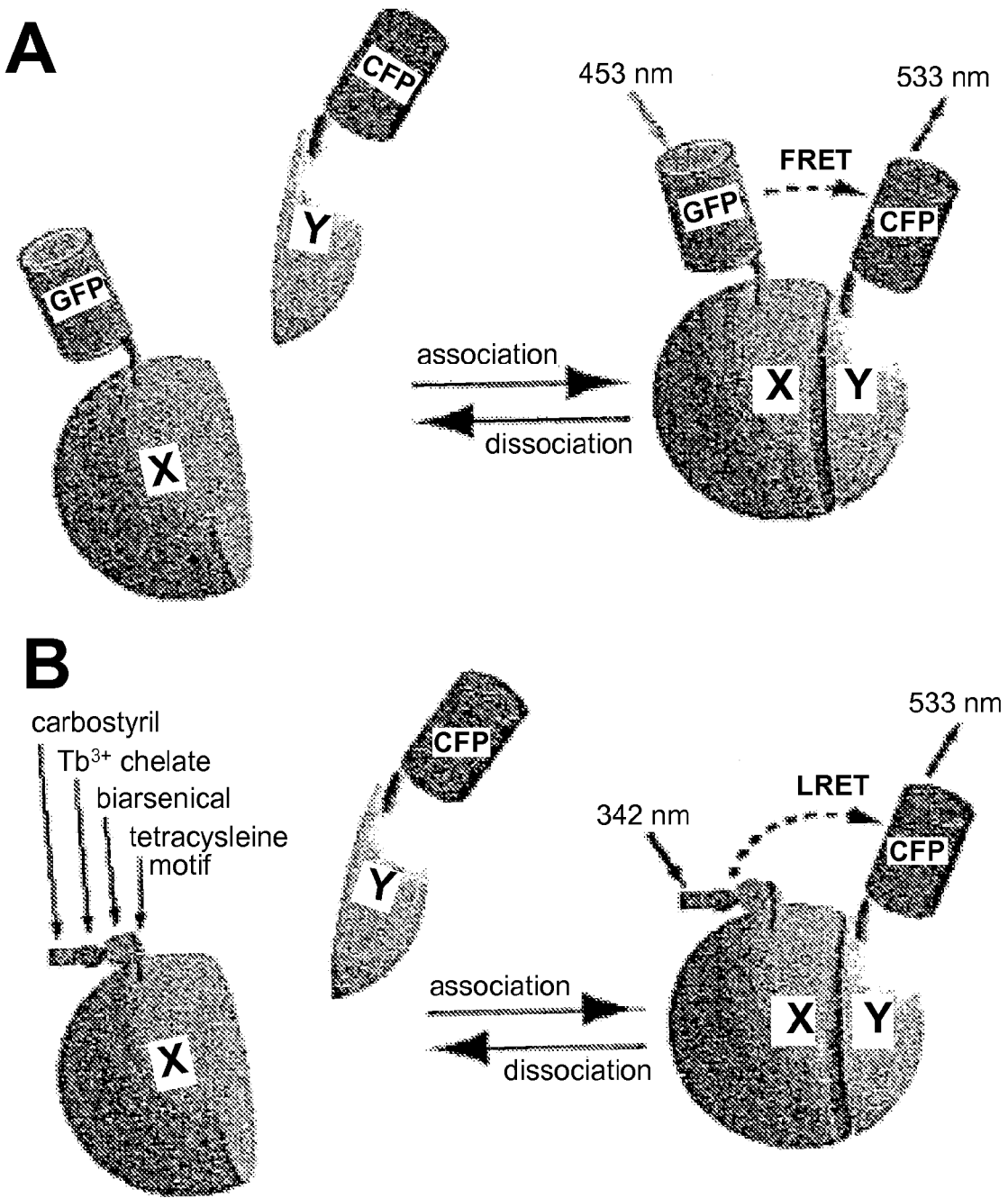
FIGS. 4A and 4B illustrate detection by resonance energy transfer of heterodimer formation between proteins X and Y.

For many kinases and phosphatases, an artificial substrate, which can be operatively linked to PAABDs and a fluorescent protein, may not be a good surrogate for the normal endogenous substrates. As such, a fluorescent protein such as GFP, particularly a circularly permuted GFP (cpGFP), can be operatively inserted into the endogenous substrate, thus generating a chimeric phosphorylation indicator (see FIG. 3). Preferably, the fluorescent protein is inserted at a hinge region or turn, such that phosphorylation can significantly change the local conformation, which is transmitted to the fluorescent protein, thereby modifying its fluorescence as discussed above. Accordingly, in another embodiment of a chimeric phosphorylation indicator containing a phosphorylatable polypeptide and a fluorescent protein, the phosphorylatable polypeptide comprises an N-terminal portion and a C-terminal portion, and the fluorescent protein is operatively inserted between the N-terminal portion and C-terminal portion of the phosphorylatable polypeptide.

Aequorea GFP-related fluorescent proteins include, for example, wild type (native) Aequorea victoria GFP (Prasher et al., supra, 1992; see, also, SEQ ID NO:2), allelic variants of SEQ ID NO:2, for example, a variant having a Q80R substitution (Chalfie et al., Science 263:802-805, 1994); and spectral variants of GFP such as CFP, YFP, and enhanced and otherwise modified forms thereof (U.S. Pat. Nos. 6,150,176; 6,124,128; 6,077,707; 6,066,476; 5,998,204; and 5,777,079), including GFP-related fluorescent proteins having one or more folding mutations, and fragments of the proteins that are fluorescent, for example, an A. victoria GFP from which the two N-terminal amino acid residues have been removed. Several of these fluorescent proteins contain different aromatic amino acids within the central chromophore and fluoresce at a distinctly shorter wavelength than the wild type GFP species. For example, the engineered GFP proteins designated P4 and P4-3 contain, in addition to other mutations, the substitution Y66H; and the engineered GFP proteins designated W2 and W7 contain, in addition to other mutations, Y66W.

Folding mutations in Aequorea GFP-related fluorescent proteins improve the ability of the fluorescent proteins to fold at higher temperatures, and to be more fluorescent when expressed in mammalian cells, but have little or no effect on the peak wavelengths of excitation and emission. If desired, these mutations can be combined with additional mutations that influence the spectral properties of GFP to produce proteins with altered spectral and folding properties, and, particularly, with mutations that reduce or eliminate the propensity of the fluorescent proteins to oligomerize. Folding mutations, with respect to SEQ ID NO:2, include the substitutions F64L, V68L, S72A, T44A, F99S, Y145F, N146I, M153T, M153A, V163A, I167T, S175G, S205T, and N212K.

Fluorescent proteins fused to target proteins can be prepared using recombinant DNA methods, and used as markers to identify the location and amount of the target protein produced. Accordingly, the present invention provides fusion proteins comprising a non-oligomerizing fluorescent protein moiety and a polypeptide of interest. The polypeptide of interest can be of any length, for example, about 15 amino acid residues, about 50 residues, about 150 residues, or up to about 1000 amino acid residues or more, provided that the fluorescent protein component of the fusion protein can fluoresce or can be induced to fluoresce when exposed to electromagnetic radiation of the appropriate wavelength. The polypeptide of interest can be, for example, a peptide tag such as a polyhistidine sequence, a c-myc epitope, a FLAG epitope, and the like; can be an enzyme, which can be used to effect a function in a cell expressing a fusion protein comprising the enzyme or to identify a cell containing the fusion protein; can be a protein to be examined for an ability to interact with one or more other proteins in a cell, or any other protein as disclosed herein or otherwise desired.

Fluorescent characteristics of Aequorea GFP-related fluorescent proteins depend, in part, on the electronic environment of the chromophore. In general, amino acids that are within about 0.5 nm of the chromophore influence the electronic environment of the chromophore. Therefore, substitution of such amino acids can produce fluorescent proteins with altered fluorescent characteristics. In the excited state, electron density tends to shift from the phenolate towards the carbonyl end of the chromophore. Therefore, placement of increasing positive charge near the carbonyl end of the chromophore tends to decrease the energy of the excited state and cause a red-shift in the absorbance and emission wavelength maximum of the protein. Decreasing a positive charge near the carbonyl end of the chromophore tends to have the opposite effect, causing a blue-shift in the protein's wavelengths. Similarly, mutations have been introduced into DsRed to produce mutants having altered fluorescence characteristics (see Example 2).

Amino acids with charged (ionized D, E, K, and R), dipolar (H, N, Q, S, T, and uncharged D, E and K), and polarizable side groups (e.g., C, F, H, M, W and Y) are useful for altering the ability of fluorescent proteins to oligomerize, especially when they substitute an amino acid with an uncharged, non-polar or non-polarizable side chain (see Examples 1 and 3). As disclosed herein, substitution of hydrophobic residues that were predicted to be involved in self-association of GFP with positively-charged residues reduced or eliminated dimerization. However, other non-conservative amino acid substitutions also can be introduced similarly or at neighboring positions in the interacting regions of the proteins, thus disrupting the localized structure of the protein, provided the substitutions do not undesirably affect the fluorescent properties of the proteins. Thus, many fluorescent protein variants have a reduced propensity to oligomerize, and may be termed "non-oligomerizing" fluorescent protein variants. For example, DsRed variants including an I125R mutation in an amino acid sequence of or similar to SEQ ID NO:12, have a reduced propensity to oligomerize. As discussed above, a non-oligomerizing fluorescent protein may be, for example, a monomeric GFP (mGFP), a monomeric CFP (mCFP) or a monomeric YFP (mYFP) having a mutation of an amino acid residue corresponding to A206, L221, F223, or a combination thereof of SEQ ID NO:2, for example, an A206K mutation, an L221K mutation, an F223R mutation, or an L221K and F223R mutation of SEQ ID NO:2; or an A206K mutation, an L221K mutation, an F223R mutation, or an L221K and F223R mutation of SEQ ID NO:6 or SEQ ID NO:10. A non-oligomerizing fluorescent protein may also be related to DsRed, for example, and may be an I125R DsRed mutant (SEQ ID NO:12, including an I125R mutation).

The present invention also relates to polynucleotides encoding a chimeric phosphorylation indicator of the invention. In one embodiment, the polynucleotide encodes a chimeric phosphorylation indicator, which contains, in operative linkage, a donor molecule, a phosphorylatable domain, a phosphoaminoacid binding domain, and an acceptor molecule, wherein the phosphoaminoacid binding domain specifically binds to a phosphoaminoacid when present in the phosphorylatable domain, the donor molecule and the acceptor molecule exhibit a detectable resonance energy transfer when the donor is excited, and the phosphorylatable domain and phosphoaminoacid binding domain do not substantially emit light to excite the acceptor. In another embodiment, the polynucleotide encodes a chimeric phosphorylation indicator containing a phosphorylatable polypeptide and a fluorescent protein, wherein the phosphorylatable polypeptide includes an N-terminal portion and a C-terminal portion, and the fluorescent protein is operatively inserted between the N-terminal portion and C-terminal portion of the phosphorylatable polypeptide. In still another embodiment, the polynucleotide encodes a chimeric phosphorylation indicator containing a phosphoaminoacid binding domain operatively linked to a phosphorylatable polypeptide and a fluorescent protein, wherein the fluorescent protein includes an N-terminal portion and a C-terminal portion, and wherein the phosphorylatable polypeptide and operatively linked phosphoaminoacid binding domain is operatively inserted between the N-terminal portion and C-terminal portion of the fluorescent protein.

Also provided is a vector containing a polynucleotide of the invention, wherein the polynucleotide encodes a chimeric phosphorylation indicator comprising, in an orientation from the amino terminus to carboxy terminus, mCFP, a polypeptide linker, an FHA2 phosphoaminoacid binding domain (SEQ ID NO: 57), a PKC substrate phosphorylatable domain comprising (SEQ ID NO: 44) and having an amino end and a carboxy end, said PKC substrate phosphorylatable domain being flanked on both its amino end and its carboxy end by a polypeptide linker, and mYFP.

Also provided is a vector containing a polynucleotide of the invention, including an expression vector, as well as host cells that contain a polynucleotide of the invention or a vector containing such a polynucleotide. In one embodiment, a polynucleotide of the invention is operatively linked to an expression control sequence, for example, a transcription regulatory element, a translation regulatory element, or a combination thereof. In another embodiment, the polynucleotide is operatively linked to a nucleotide sequence encoding a membrane translocating domain or a cell compartmentalization domain.

A vector generally contains elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, Meth. Enzymol., Vol. 185, Goeddel, ed. (Academic Press, Inc., 1990); Jolly, Canc. Gene Ther. 1:51-64, 1994; Flotte, J. Bioenerg. Biomemb. 25:37-42, 1993; Kirshenbaum et al., J. Clin. Invest. 92:381-387, 1993).

A vector for containing a polynucleotide encoding a chimeric phosphorylation indicator can be a cloning vector or an expression vector, and can be a plasmid vector, viral vector, and the like. Generally, the vector contains a selectable marker independent of that encoded by a polynucleotide of the invention, and further can contain transcription or translation regulatory elements, including a promoter sequence, which can provide tissue specific expression of a polynucleotide operatively linked thereto, which can, but need not, be the polynucleotide encoding the chimeric phosphorylation indicator, thus providing a means to select a particular cell type from among a mixed population of cells containing the introduced vector and recombinant nucleic acid molecule contained therein.

Where the vector is a viral vector, it can be selected based on its ability to infect one or few specific cell types with relatively high efficiency. For example, the viral vector also can be derived from a virus that infects particular cells of an organism of interest, for example, vertebrate host cells such as mammalian host cells. Viral vectors have been developed for use in particular host systems, particularly mammalian systems and include, for example, retroviral vectors, other lentivirus vectors such as those based on the human immunodeficiency virus (HIV), adenovirus vectors, adeno-associated virus vectors, herpesvirus vectors, vaccinia virus vectors, and the like (see Miller and Rosman, BioTechniques 7:980-990, 1992; Anderson et al., Nature 392:25-30 Suppl., 1998; Verma and Somia, Nature 389:239-242, 1997; Wilson, New Engl. J. Med. 334:1185-1187 (1996)).

Recombinant production of a chimeric phosphorylation indicator involves expressing a polypeptide encoded by a polynucleotide. The sequence of the polynucleotide can be confirmed using routine methods, including, for example, PCR methods (see, for example, U.S. Pat. No. 4,683,195; Mullis et al., Cold Spring Harbor Symp. Quant. Biol. 51:263, 1987; Erlich, ed., "PCR Technology" (Stockton Press, NY, 1989)). The construction of expression vectors and the expression of a polynucleotide in transfected cells involves the use of molecular cloning techniques also well known in the art (see Sambrook et al., In "Molecular Cloning: A Laboratory Manual" (Cold Spring Harbor Laboratory Press 1989); "Current Protocols in Molecular Biology" (eds., Ausubel et al.; Greene Publishing Associates, Inc., and John Wiley & Sons, Inc. 1990 and supplements). Expression vectors contain expression control sequences operatively linked to a polynucleotide sequence of interest, for example, that encoding a non-oligomerizing fluorescent protein, as indicated above. The expression vector can be adapted for function in prokaryotes or eukaryotes by inclusion of appropriate promoters, replication sequences, markers, and the like. An expression vector can be transfected into a recombinant host cell for expression of a chimeric phosphorylation indicator, and host cells can be selected, for example, for high levels of expression in order to obtain a large amount of isolated protein. A host cell can be maintained in cell culture, or can be a cell in vivo in an organism.

An expressed chimeric phosphorylation indicator can be operatively linked to a polypeptide of interest, for example, a peptide tag, which can be used to facilitate isolation of the indicator. For example, a polyhistidine tag containing, for example, six histidine residues, can be incorporated at the N-terminus or C-terminus of the chimeric phosphorylation indicator, which then can be isolated in a single step using nickel-chelate chromatography (see Example 1). Additional peptide tags, including a c-myc peptide, a FLAG epitope, or any ligand (or cognate receptor), including any peptide epitope (or antibody, or antigen binding fragment thereof, that specifically binds the epitope are well known in the art and similarly can be used. (see, for example, Hopp et al., Biotechnology 6:1204, 1988; U.S. Pat. No. 5,011,912).

Kits also are provided to facilitate and, where desired, standardize the compositions of the invention and the uses thereof. A kit can contain one or more compositions of the invention, for example, one or a plurality of chimeric phosphorylation indicators, or one or a plurality of polynucleotides that encode the indicators. In addition, the kit can contain instructions for using the components of the kit, particularly the compositions of the invention that are contained in the kit.

Such kits can be particularly useful where they provide a plurality of different chimeric phosphorylation indicators because the artisan can conveniently select one or more indicators having the properties desired for a particular application. Similarly, a kit containing a plurality of polynucleotides encoding different chimeric phosphorylation indicators provides numerous advantages. For example, the polynucleotides can be engineered to contain convenient restriction endonuclease or recombinase recognition sites, thus facilitating operative linkage of the polynucleotide to a regulatory element or to a polynucleotide encoding a phosphorylatable domain or PAABD of interest.

The present invention further relates to a method for detecting a kinase or phosphatase in a sample. In one embodiment, a method of the invention is performed, for example, contacting the sample with a chimeric phosphorylatable indicator, which contains, in operative linkage, a donor molecule, a phosphorylatable domain, a phosphoaminoacid binding domain, and an acceptor molecule, wherein the phosphoaminoacid binding domain specifically binds to a phosphoaminoacid when present in the phosphorylatable domain, the donor molecule and the acceptor molecule exhibit a detectable resonance energy transfer when the donor is excited, and the phosphorylatable domain and phosphoaminoacid binding domain do not substantially emit light to excite the acceptor; exciting the donor molecule; and determining a fluorescence or luminescence property in the sample, wherein the presence of a kinase or phosphatase in the sample results in a change in the degree of FRET or LRET, thereby detecting the kinase or phosphatase in the sample. The change in the degree of FRET or LRET can be an increased amount of FRET or LRET, or can be a decreased amount of FRET or LRET, and the change can be indicative of the presence of a kinase in the sample, or, where the phosphorylatable domain is phosphorylated prior to contacting the sample with a chimeric phosphorylatable indicator, can be indicative of a phosphatase in the sample.

Fluorescence in a sample generally is measured using a fluorimeter, wherein excitation radiation from an excitation source having a first wavelength, passes through excitation optics, which cause the excitation radiation to excite the sample. In response, a non-oligomerizing fluorescent protein in the sample emits radiation having a wavelength that is different from the excitation wavelength. Collection optics then collect the emission from the sample. The device can include a temperature controller to maintain the sample at a specific temperature while it is being scanned, and can have a multi-axis translation stage, which moves almicrotiter plate holding a plurality of samples in order to position different wells to be exposed. The multi-axis translation stage, temperature controller, auto-focusing feature, and electronics associated with imaging and data collection can be managed by an appropriately programmed digital computer, which also can transform the data collected during the assay into another format for presentation. This process can be miniaturized and automated to enable screening many thousands of compounds in a high throughput format. These and other methods of performing assays on fluorescent materials are well known in the art (see, for example, Lakowicz, "Principles of Fluorescence Spectroscopy" (Plenum Press 1983); Herman, "Resonance energy transfer microscopy" In "Fluorescence Microscopy of Living Cells in Culture" Part B, Meth. Cell Biol. 30:219-243 (ed. Taylor and Wang; Academic Press 1989); Turro, "Modern Molecular Photochemistry" (Benjamin/Cummings Publ. Co., Inc. 1978), pp. 296-361).

In another embodiment, a method for detecting a kinase or phosphatase in a sample is performed by contacting the sample with a chimeric phosphorylatable indicator containing a phosphorylatable polypeptide and a fluorescent protein, determining a fluorescence property in the sample, wherein the presence of kinase or phosphatase activity in the sample results in a change in the fluorescence property as compared to the fluorescent property in the absence of a kinase or phosphatase activity, thereby detecting the kinase or phosphatase in the sample. The chimeric phosphorylation indicator can containing a phosphorylatable polypeptide that includes an N-terminal portion and a C-terminal portion, such that the fluorescent protein is operatively inserted between the N-terminal portion and C-terminal portion of the phosphorylatable polypeptide; or the chimeric phosphorylation indicator can contain a phosphoaminoacid binding domain operatively linked to a phosphorylatable polypeptide, which is operatively inserted between an N-terminal portion and a C-terminal portion of the fluorescent protein.

The sample to be examined for kinase activity can be any sample, including, for example, a sample containing a synthetic product to be examined for kinase or phosphatase activity. In one embodiment, the sample is a biological sample, which can be cell, tissue or organ sample, or an extract of such a sample. In another embodiment, the method is performed on an intact cell, which can be in cell culture or can be in a tissue sample. For such a method, the chimeric phosphorylatable indicator can contain a targeting sequence such as a cell compartmentalization domain that can target the chimeric phosphorylatable indicator to cytosol, endoplasmic reticulum, mitochondrial matrix, chloroplast lumen, medial trans-Golgi cisternae, a lumen of a lysosome, or a lumen of an endosome. A membrane translocating domain can be a particularly useful cell compartmentalization domain is a membrane translocating domain, which can facilitate translocation of the chimeric phosphorylation indicator into an intact cell.

The phosphorylatable polypeptide in a chimeric phosphorylation indicator comprising a fluorescent protein and a phosphorylatable polypeptide can be unphosphorylated or phosphorylated at an amino acid position specific for a kinase or a phosphatase, depending on whether the method is for detecting a kinase or phosphatase. A method of the invention also can be used to detect an absence of kinase or phosphatase activity in the sample is due to the presence of a kinase inhibitor or phosphatase inhibitor. As such, the method is useful for identifying a kinase inhibitor or a phosphatase inhibitor.

The following examples are intended to illustrate, but not limit, the present invention.

EXAMPLE 1

Preparation and Characterization of a Chimeric Reporter Protein for a Serine/Threonine Protein Kinase This example provides a method for preparing a chimeric protein kinase A (PKA; cAMP-dependent protein kinase) reporter protein, and demonstrates that such a chimeric reporter molecule can detect serine/threonine kinase activity.

Plasmid Construction

The PKA chimeric reporter protein was constructed by fusing the enhanced cyan fluorescence protein (1-227; ECFP; SEQ ID NO:6; K26R/F64L/S65T/Y66W/N146I/M153T/V163A/N164H), a truncated version of 14-3-3τ, a modified kemptide and citrine, which is an improved yellow fluorescence protein having a sequence as set forth in SEQ ID NO:10, except containing a Q69M mutation. 14-3-3τ (1-232) was amplified using the cDNA of 14-3-3τ (see GenBank Accession No. D87662) in pcDNA3 vector as the template.

For PCR, the forward primer had the sequence (SEQ ID NO:26) 5'-GGGCATGCATATGGAGAAGACTGAGCT-GATCCAG-3', and incorporates a Sph I site. The reverse primer had the sequence (SEQ ID NO:27) 5'-CGCG-GAGCTCGCTGCCGCCG-GTGCCGCCCAGGCTG-GCGCGACGGAGGCTGCCGCCGGTGCCGC-CTGCAGAGT CTGATGTCCAAAGTGTTAGG-3-', which introduces a short linker peptide (AGGTGGS; SEQ ID NO:19), the kemptide sequence (LRRASLG; SEQ ID NO:32), a second short linker peptide (GTGGSEL; SEQ ID NO:21) and a Sac I site.

PCR was performed using 50 ng of template, 300 nM of each primer, 500 nM of each dNTP, 2.5 Unit of Taq polymerase (Gibco) in 1×PCR reaction buffer (Boehringer Mannheim) with nanopure water (50 µl total volume). PCR was performed as follows: 95° C., 5 min; 2 cycles of (95° C., 1 min; 40° C., 1 min; 72° C., 2.5 min); 5 cycles of (95° C., 1 min; 43° C., 1 min; 72° C., 2.5 min); 5 cycles of (95° C., 1 min; 45° C., 1 min; 72° C., 2.5 min); 15 cycles of (95° C., 1 min; 52° C., 1 min; 72° C., 2.5 min; 72° C., 7 min), then hold at 25° C.

The amplification product was purified using the Qiagen gel purification kit, then digested with Sph I and Sac I overnight. The digested mixture was purified using Qiagen PCR purification kit, and the purified fragment was ligated into Sph I/Sac I-digested pRSET$_B$ (Invitrogen) containing the cDNA sequence for ECFP and citrine (from Yellow cameleon 3.3). The construct was within the Bam HI/Eco RI sites of pRSET$_B$, and is behind a polyhistidine tag for bacterial expression. The resulting plasmid was amplified, sequenced and mutagenized using the QuickChange™ site-directed mutagenesis kit (Stratagene) to introduce one amino acid change in the kemptide sequence, generating the plasmid C4kY2.1-pRSET$_B$.

Primers for mutagenesis had the following sequence:

```
5'-CGTCGCGCCAGCCTGCCAGGCACCGGCGGCAG  (SEQ ID NO: 28)
C.3', and

5'-GCTGCCGCCGGTGGCTGGCAGGCTGGCGCGAC  (SEQ ID NO: 29)
G-3'.
```

The S475A mutant was generated similarly using the following primers:

```
GCCTCCGTCGCGCCGCACTGCCAGGCACCGGC;  (SEQ ID NO: 30)
and

GCCGGTGCCTGGCAGTGCGGCGCGACGGAGGC.  (SEQ ID NO: 31)
```

For mammalian expression, both C4kY2.1 and C4kY2.1 (S475A) were cloned into the vector pcDNA3 behind a Kozak sequence for mammalian expression.

Protein Expression, Phosphorylation and In Vitro Spectroscopy

C4kY2.1-pRSET$_B$ and C4kY2.1 (S475A)-pRSET$_B$ each were transformed into E. coli strain BL21(DE3). A single colony was picked and grown in 100 to 500 ml LB medium containing 0.1 mg/ml ampicillin at 37° C. to an optical density of 0.4-0.8 at 600 nm, then induced with 0.1 mg/ml isopropyl thiogalactoside (IPTG) at 25° C. for 12 to 24 hr. Cells were harvested by centrifugation, then the bacterial pellet was suspended in 4 to 10 ml B-PER™ II Bacterial Extraction Reagent (Pierce) and lysed by gentle shaking at 25° C. for 15 min in the presence of protease inhibitors (Complete™ EDTA-free Protease Inhibitor tablet (Roche), 1 mM phenylmethylsulfonyl fluoride). The lysate was clarified by centrifugation at 12,000 g for 30 min at 4° C.

Binding of the His$_6$ (SEQ ID NO:64) tag to Ni-NTA agarose (Qiagen) was carried out in a batch mode. The supernatant was filtered through a 0.22 μM syringe filter, then transferred to a new tube, to which 0.3 to 1 ml of the 50% (v/v) Ni-NTA slurry was added. The suspension was mixed gently on a rotary shaker at 4° C. for 1 hr. The lysate-Ni-NTA mixture was loaded into a column, which was washed with 10 volumes of TNS300 buffer (Tris-HCl, pH 7.4, 300 mM NaCl) and 10 volumes of TNS300 containing 10 mM imidazole. The chimeric protein was eluted with 1 to 3 ml of elution buffer (100 mM imidazole in TNS300) and dialyzed in TNS300 buffer at 4° C. for 12 to 24 hr. When necessary, the protein was concentrated using a YM-30 Microcon or Centricon concentrator (Fisher).

Chimeric proteins were phosphorylated with the catalytic subunit of PKA (New England Biolabs; 2.5 U/μl) in PKA kinase reaction buffer (50 mM Tris-HCl, pH 7.5, 10 mM MgCl$_2$, 1 mg/ml BSA) in the presence of an optional amount of adenosine triphosphate, ATP (200 μM to 1 mM) at 25° C. Fluorescence was monitored using an excitation wavelength of 434 nm before and after adding ATP to the rest of the components. Experiments were performed in a Perkin-Elmer Spectrofluorometer LS50B. Emission spectra (excitation 380 nm, emission 430 to 650 nm) were collected and 536/476 emission ratios calculated at each time point.

For in vitro kinase assay, different constructs were incubated with 7.5 unit of catalytic subunit of PKA and 6.5 nM (1.2 μCi) γ-$^{32}$P)-ATP (6000 Ci/mmol, New England Nuclear) in PKA kinase reaction buffer, in a total volume of 30 μl at 25° C. for 30 min to 12 hr. Ten μl of the reaction mixture was spotted onto a phosphocellulose disk, immersed in 0.5% H$_3$PO$_4$ and washed with the PKA kinase reaction buffer three times, for 10 min each. Transfer of $^{32}$p was measured by standard scintillation counting.

For testing the specificity of the reporter, fluorescence change and transfer of $^{32}$p upon incubation with CaMKII (New England Biolabs) and PKC,βII were followed similarly. The reaction conditions for CaMKII was 5 U/μl CaMKII, 1 mM ATP or 6.5 nM (1.2 μCi) (γ-$^{32}$P)ATP (6000 Ci/mmol, NEN), 2 mM CaCl$_2$, 2.4 μM calmodulin in CaMKII buffer (20 mM Tris-HCl, pH 7.5, 10 mM MgCl$_2$, 0.5 mM dithiothreitol and 0.1 mM Na$_2$EDTA) at 25° C. for 30 min to 12 hr. The reaction conditions for PKCβII was 3 U/μl PKCβII, 1 mM ATP or 6.5 nM (1.2 μCi) (γ-$^{32}$P)-ATP (6000 Ci/mmol), 5 mM CaCl$_2$, 140 μM phosphatidylserine and 3.8 μM diacylglycerol in buffer (20 mM Tris-HCl, pH 7.5, 10 mM MgCl$_2$) at 25° C. for 30 min to 12 hr.

For testing phosphatases, the PKA-phosphorylated chimeric reporter protein was concentrated using a YM-30 Microcon concentrator and an equal volume of TNS300 buffer was added. The protein was then purified by Ni-NTA as described above. The purified protein was dephosphorylated with 2.5 U protein phosphatase 1 (PP 1; New England Biolabs) in the presence of 1 mM MnCl$_2$ in PP1 buffer (50 mM Tris-HCl, pH 7.0, 0.1 mM Na$_2$EDTA, 5 mM DTT, 0.01% Brij35) at 25° C. for 30 min to 3 hr.

Cell Culture

HeLa cells or COS-7 cells were plated onto sterilized glass coverslips in 2 cm dishes or in 10 cm plates and grown to 50-90% confluency at 37° C. in low-glucose DMEM medium. Cells were transfected with the FuGENE-6 transfection reagent (Roche). Briefly, cells on 24-mm glass coverslips in a 2 cm dish were transfected with 0.5 μg DNA (purified using the Midiprep Kit from Qiagen), 100 μl of OptiMEM1 medium and 3 μl of FuGENE-6. After a 30 min incubation at room temperature, the mixture was added to the cells.

For imaging analysis, cells were incubated for 24-72 hr at 37° C. in fetal bovine serum in low glucose DMEM, then washed twice with HBSS buffer (20 mM Hepes, pH 7.4, 2 g/l D-glucose), maintained in buffer in the dark at room temperature, with addition of forskolin (FsK; Calbiochem) and N$^6$, 2'-O-dibutyryl cyclic adenosine 3', 5' monophosphate (db-cAMP; Calbiochem). FsK was dissolved in DMSO to be used as a 50 mM stock solution. To add a DMSO solution, 500 μl of HBSS buffer was taken from the imaging dish and mixed with the DMSO solution, then added back to the imaging dish. For inhibition studies of PKA activity, cells were preincubated in DMEM medium containing 10 μM H-89 for approximately 2 hr.

Imaging Studies

Cells were imaged on a Zeiss Axiovert microscope with a cooled CCD camera (Photometrics; Tucson Ariz.), controlled by Metafluor 2.75 software (Universal Imaging; West Chester Pa.). Dual-emission ratio imaging used a 440DF30 excitation filter, a 455DRLP dichroic mirror and two emission filters (480DF30 for ECFP, 535DF25 for citrine) altered by a filter changer (Lambda 10-2, Sutter Instruments, San Rafael, Calif.). Fluorescence images were background-corrected. Exposure time was 1000 ms and images were taken every 15 sec.

Results

The protein kinase, PKA, which is involved in cell signaling, was used to exemplify a ratiometric indicator for serine/threonine phosphorylation. cAMP is one if the main second messengers and plays an important role as a signal transducer in many cellular activities, the signal being transmitted by activation of PKA. PKA regulates specific gene expression by phosphorylating specific nuclear proteins at serine/threonine residues within consensus sequences. The 14-3-3 family of proteins mediates signal transduction by binding to phosphoserine-containing proteins and, therefore, can contain a consensus sequence that could encompass consensus site for PKA. Accordingly, fusion proteins were constructed in which a GFP FRET pair were linked by a 14-3-3 protein and a substrate peptide. Upon phosphorylation, binding between 14-3-3 and the substrate can bring two GFPs into proximity such that FRET is enhanced as the readout for phosphorylation. For the GFP FRET pair, ECFP and citrine, which is an improved yellow fluorescence protein with a better stability to acid conditions, were selected. The C-terminal tail of 14-3-3 was omitted, and replaced with a flexible linker AGGTGGS (SEQ ID NO:19). Another flexible linker GGTGGSEL (SEQ ID NO:21) was inserted between the substrate peptide and citrine. A number of chimeras containing different substrate sequences, including the kemptide (LRRASLG; SEQ ID NO:32), a modified kemptide (LRRASLP; SEQ ID NO:20) and a peptide sequence derived from Raf-259 (AQRSTSTPN; SEQ ID NO:33), were generated. The C4kY2.1 reporter (FIG. 6B) gave the best response to the activation of PKA. C4kY1.1 containing the kemptide sequence also was responsive to the activation of PKA. While the 14-3-3 recognized a consensus sequence RSXSXP (SEQ ID NO:34), it was rationalized that mutagenizing the glycine at the +2 position with respect to the serine, to a proline, could increase the binding affinity. As such, the C4kY2.1 chimeric reporter protein was constructed containing a modified kemptide sequence.

In Vitro Characterization of a Chimeric Reporter Protein

The chimeric reporter protein C4kY2.1 was efficiently phosphorylated by the catalytic subunit of PKA, while the mutant C4kY2.1 (S475A) protein was not phosphorylated in the in vitro phosphorylation assay. This result indicates that phosphorylation occurs at the designated serine in the modified kemptide sequence (LRRAS$^{475}$LP; SEQ ID NO:20) containing the consensus PKA phosphorylation site (RRXS; SEQ ID NO:35).

The effect of a structural alteration due to phosphorylation on the efficiency of FRET also was examined. Excitation of the fluorophore in the ECFP at 434 nm results in fluorescence emission at 526 nm from the citrine due to FRET between the two fluorophores. When the C4kY2.1 chimeric reporter protein was phosphorylated, FRET was increased and the ratio of the emission at 526 nm and 476 nm increased from a value of 1.09 to 1.42 in a time-dependent manner. Negative controls, in which either PKA or ATP were omitted, demonstrated that FRET change is dependent on the PKA phosphorylation. The mutant C4kY2.1 (S475A), in which the designated serine was mutated to an alanine did not give any change of FRET upon incubation with PKA catalytic subunit and 1 mM ATP. This result demonstrates that the FRET change is due to a conformational change, for example, due to binding between the phosphorylated peptide and 14-3-3, which is induced by the PKA phosphorylation at the serine 475.

Following treatment of the C4kY2.1 chimera with 10 μg of trypsin for 40 min (Miyawaki and Tsien, Meth. Enzymol. 37:472-500, 2000), FRET efficiencies of phosphorylated and nonphosphorylated C4kY2.1 were calculated to be 20 and 30%, respectively. Furthermore, the PKA/ATP-dependent FRET change was reversible upon treatment with protein phosphatase 1 (PP 1), which is specific for phosphorylated serine/threonine. When the purified PKA-phosphorylated chimera was incubated with PP 1, FRET was decreased and the emission ratio of 526 nm and 476 nm decreased from a value of 1.39 to 1.14 in a time-dependent manner.

The specificity of the chimeric PKA reporter protein C4kY2.1 was examined by applying CaMKII and PKCβII to the chimera in vitro. These two kinases have the consensus sequences RXXS/T (SEQ ID NO:36) and K/RXXS/T (SEQ ID NO:37), respectively, which overlap with the kemptide sequence. The chimera was poorly phosphorylated by both kinases, and incubation of the chimera with the either kinase did not result in a significant FRET change. These results demonstrate that the C4kY2.1 chimera is specific to PKA phosphorylation in vitro.

Expression and Behavior of PKA Reporter in Mammalian Cells

When the chimeric PKA reporter C4kY2.1 was transfected into HeLa cells, the fluorescence was uniformly distributed in the cytosolic compartment, but was excluded from the nucleus, as expected for such a chimeric protein that lacked targeting signals. A similar expression pattern also was observed in COS-7 cells. To elevate the activities of PKA, transfected cells were treated with cAMP-elevating agents. Exposure of the cells to 50 μM FsK and 1 mM dibutyryl cAMP increased the 535 nm/480 nm ratio in a time-dependent manner. Typically the ratio reached a plateau at 5 min after stimulation. When C4kY2.1 (S475A) transfected cells were treated in the same condition, no change in the 535 nm/480 nm ratio was observed. This result is consistent with the intramolecular binding between 14-3-3 and the peptide phosphorylated by PKA at the serine475 being responsible for the FRET change observed.

Either FsK or dbcAMP, alone, induced the FRET change. In general, the change in the emission ratio 535 nm/480 nm was from 25% to 34%. In addition, the change and kinetics were dependent on the fluorescence intensity of the transfected cells; i.e., the brighter the cell, the bigger the FRET change and the more slowly the plateau was reached. Administration of 1 mM dbcAMP, alone, slowly increased the 535 nm/480 nm ratio, while pretreatment with 10 μM H-89, a PKA inhibitor, for 2 hr slowed down the process even more, but did not completely inhibited it. The change in the emission ratio 535 nm/480 nm in the cells pretreated with H-89 was 46%, suggesting that the pretreatment with the PKA inhibitor reduced the basal level of PKA phosphorylation inside cells prior to the stimulation, giving rise to a greater FRET change. A similar increase in the 535 nm/480 nm ratio was observed in COS-7 cells treated with FsK and with dbcAMP, although the change was smaller (about 5%) and a higher starting ratio was observed.

EXAMPLE 2

Preparation and Characterization of Chimeric Reporter Proteins for Detecting Tyrosine Kinase Activity This example provides methods for preparing a chimeric src reporter protein and a chimeric EGFR (epidermal growth factor receptor) reporter protein, and demonstrates that such chimeric reporter proteins can detect tyrosine kinase activity.

Preparation of the Chimeric Gene Encoding the Chimeric EGFR Reporter Protein

The SH2 domain from mouse p52 Shc (see Lanning and Lafuse, Immunogenetics 49:498-504, 1999; GenBank Accession No. AF054823) was amplified by PCR using the following primers:

2 EGFR.Fwd-
(5'-GCCGCCCGCATGCATTGGTTCCACGGGAAGCTG    SEQ ID NO: 38

AGCCGG-3'; and)

EGFRoptsub.Rev-
(5'-TACCATGAGCTCTGATTGCGGAG-CCATGTTC    SEQ ID NO: 39

ATGTACTCAGCTTCCTCTTCAGGCTTCCCAGATCC-

AGAGTGAGACCCCACGGGTTGCTCTAGGCACAG-

3').

The PCR reaction was assembled as: 67 µl of water, 10 µl of 10×Taq buffer (Promega), 16 µl of 25 mM $MgCl_2$, 2 µl of a 25 mM stock of dNTPs, 1.5 µl of 100 µM EGFR.Fwd primer, 1.5 µl of 100 µM EGFRoptsub.Rev primer, 1 µl of 0.1 µg/µl p52 Shc template, and 1 µl of Taq polymerase (Promega). The following cycle was used: 94° C., 2 min; 2 cycles of (95° C., 2 min; 40° C., 2 min; 72° C., 2:30 min); 28 cycles of (95° C., 1 min; 52° C., 1 min; 72° C., 2:30 min); 72° C., 10 min; 25° C. hold.

Figure 7A:
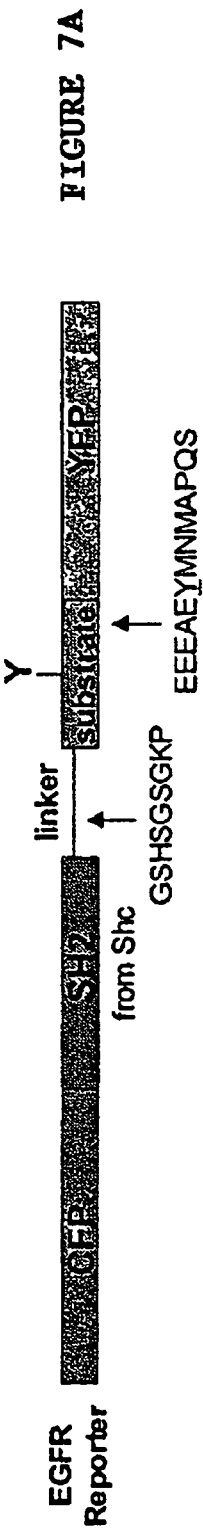
FIGS. 7A, 7B and 7C illustrate the structures of the chimeric EGFR (FIG. 7A), Src (FIG. 7B), and PKC reporter (CKAR) proteins.

PCR product was digested with Sac I and Sph I and ligated into similarly digested YC3.3 plasmid, which contained the genes for EYFP and ECFP behind an N-terminal $His_6$ (SEQ ID NO:64) tag, and is derived from the vector $pRSET_B$. This construct, called "Eopt-$pRSET_B$", was used for bacterial expression of the EGFR reporter. The structure of the chimeric EGFR reporter protein is illustrated in FIG. 7A.

For mammalian expression, the Eopt-$pRSET_B$ plasmid was cloned into the vector pcDNA3 using the Bam HI and Eco RI restriction sites. Constructs prepared in this way retained their N-terminal $His_6$ (SEQ ID NO:64) tags. The mammalian expression plasmid was named "Eopt-pcDNA3".

Preparation of the Chimeric Gene Encoding the Chimeric Src Reporter Protein

The SH2 domain from v-Src was amplified by PCR using the following primers:

3 SrcSH2.Fwd-
(5'-GCCGCTCGCATGCATTGGTATTTTGGGAAGATC    SEQ ID NO: 40

AC-3'; and)

SrcSH2.Rev-
(5'-CACCATGAGCTCAAATTCACCGTAGATCTCA-    SEQ ID NO: 41

GAACCCTCACCAGAACCCGGCTTCCCAGATCCAGATG

TAGACC-CACAGACGTTAGTCAGGCG-3').

The PCR reaction was assembled as 67 µl of water, 10 µl of 10× Taq buffer (Promega), 16 µl of 25 mM $MgCl_2$, 2 µl of a 25 mM stock of dNTPs, 1.5 µl of 100 µM SrcSH2.Fwd primer, 1.5 µl of 100 µM SrcSH2.Rev primer, 1 µl of 0.1 µg/µl v-Src template, and 1 µl of Taq polymerase (Promega). The following cycle was used: 94° C., 2 min; 2 cycles of (95° C., 2 min; 40° C., 2 min; 72° C., 2:30 min); 28 cycles of (95° C., 1 min; 52° C., 1 min; 72° C., 2:30 min); 72° C., 10 min; 25° C. hold.

Figure 7B:
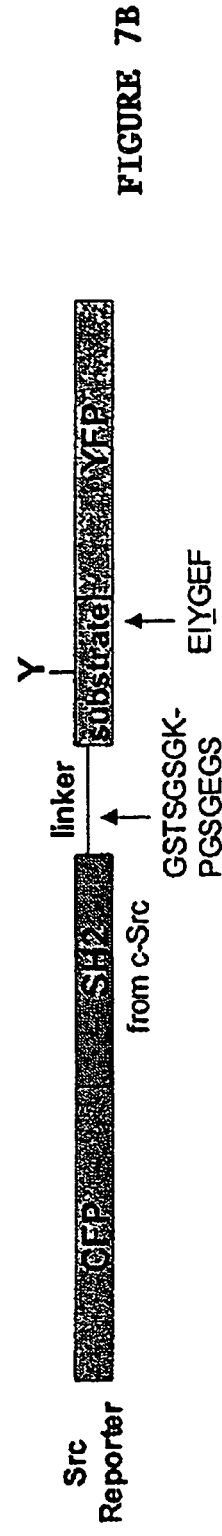

The PCR product was digested with Sac I and Sph I and ligated into YC3.3 plasmid digested with the same enzymes. This construct, called "SC-$pRSET_B$", was used for bacterial expression of the Src reporter. The structure of the chimeric Src reporter protein is illustrated in FIG. 7B.

For mammalian expression, the SC-$pRSET_B$ plasmid was cloned into the vector pcDNA3 using the Bam HI and Eco RI restriction sites. Constructs prepared in this way retained their N-terminal $His_6$ (SEQ ID NO:64) tags. The mammalian expression plasmid was named "SC-pcDNA3".

Preparation of the Chimeric EGFR Reporter Protein and Chimeric Src Reporter Protein from Bacterial Cells For bacterial expression, chemically-competent DH5α bacteria were transformed with the Eopt-$pRSET_B$ plasmid. The cells were plated on LB agar supplemented with ampicillin (50 µg/ml. A single bacterial colony was used to inoculate an overnight 1 ml culture of LB supplemented with ampicillin (50 µg/ml), then the 1 ml culture was used inoculate a 500 ml culture of LB supplemented with ampicillin (50 µg/ml). The cells were grown at 37° C. until $OD_{600}$ of about 0.4, then protein expression was induced with the addition of 500 µl of 1 M IPTG. The cells were incubated with shaking at 30° C. for 6 to 12 hr more, then harvested by centrifugation in GS-3 tubes at 4° C. for 10 min at 4000 rpm.

The cell pellet was resuspended in 10 ml of B-PERII Reagent (Pierce) and the mixture was incubated with gentle rocking at 25° C. for 10 min, then the cell debris was pelleted by centrifugation in SS-34 tubes at 4° C. for 15 min at 15,000 rpm. The supernatant was separated and combined with 1 ml of Ni-NTA agarose (Qiagen) and the suspension was incubated at 4° C. for 30 min with gentle rotation. The suspension then was transferred to a screening column and the beads were rinsed with 2×8 ml of 50 mM Tris pH 7.4/300 mM NaCl/10 mM imidazole. The chimeric protein was eluted with 5 ml of 50 mM Tris pH 7.4/300 mM NaCl/100 mM imidazole, then dialyzed overnight in 50 mM Tris pH 7.4/50 mM NaCl/10 mM $MgCl_2$ and stored in small aliquots at −20° C. The typical yield was 5 ml of 1-5 µM pure EGFR reporter protein.

The same procedure was used to prepare the chimeric Src reporter protein from bacterial cells.

Expression of the Chimeric EGFR Reporter Protein and Chimeric Src Reporter Protein in Mammalian Cells Eopt-pcDNA3 plasmid was amplified and purified using the endotoxin-free midiprep kit from Qiagen. For fluorescence measurements in living cells, mouse B82 cells, HeLa cells, or NIH3T3 cells in 2 cm dishes at 50-90% confluence were transfected with 1 µg of the Eopt-pcDNA3 plasmid using Fugene (Roche) according to standard protocols. The cells were incubated with the DNA for 10-24 h at 37° C. in 5% $CO_2$ and 10% calf (B82 cells and NIH3T3 cells) or fetal bovine serum (HeLa cells) in high glucose DMEM. The cells were then serum-starved in 0.5% calf serum (in high glucose DMEM) for 6 to 24 hr.

For biochemical analysis of the reporter expressed in mammalian cells, mouse B82 cells, HeLa cells, or NIH3T3 cells in 10 cm dishes at 50-90% confluence were transfected with 1 µg of the Eopt-pcDNA3 plasmid using Effectene (Qiagen) according to standard protocols. The cells were incubated with the DNA for 10 to 24 hr at 37° C. in 5% $CO_2$ and 10% calf (B82 cells and NIH3T3 cells) or fetal bovine serum (HeLa cells) in high glucose DMEM. The cells were then serum-starved in 0.5% calf serum (in high glucose DMEM) for 6 to 24 hr.

Expression of the chimeric EGFR reporter protein was assessed by fluorescence in vitro. The assay was performed at room temperature in 50 mM Tris, pH 7.4, 50 mM NaCl, 10 mM $MgCl_2$, 100 µM ATP and EGFR enzyme (Sigma). CFP was excited at 400 nM, and CFP and YFP emissions were measured at 75 nM and 525 nm, respectively. A cutoff filter at 420 nm was used. The YFP:CFP ratio increased only when EGFR and ATP were included in the reaction mixture.

The identical procedure was used to express the chimeric Src reporter protein in mammalian cells, except that the in vitro response was performed using 50 mM Tris, pH 7.4, 50 mM NaCl, 10 mM MgCl$_2$, 100 μM ATP and c-Src enzyme (Upstate Biotechnology). CFP was excited at 432 nM, and CFP and YFP emissions were measured at 475 nm and 525 nm, respectively.

Fluorescence Measurements of the Chimeric EGFR and Src Reporter Proteins in Mammalian Cells Live-cell imaging was performed as described for the cameleon Ca$^{+2}$ indicators (Miyawaki et al., Nature 388:882-887, 1997). EGFR was stimulated in HeLa cells and in mouse L cells by addition of 50 ng/ml of EGF (Sigma). For measuring the effect of inhibitor on the EGFR reporter, 100 nM of AG1478 (Calbiochem) was incubated with the cells in HBSS (20 mM Hepes, pH 7.4, 2 g/l D-glucose) for 30 min at room temperature prior to application of EGF.

Addition of EGF to the transfected mouse L cells resulted in an immediate increase in the emission ratio, and reached a plateau at about a 27% emission ratio change by about 2 minutes. Following wash-out of the EGF from the culture, the emission ratio decreased in a time-dependent manner, and the decrease was accelerated by the addition of the AG1478 EGFR inhibitor. No response was observed when cells were incubated with the EGFR inhibitor prior to addition of EGF, whereas the Src kinase inhibitor, PP 1, had no effect on the increase in emission ratio due to EGF.

Src activity was stimulated in HeLa cells and in NIH3T3 cells with EGF (50 ng/ml) and PDGF (50 ng/ml), respectively. To inhibit Src activity, PP1 (A.G. Scientific) was incubated with the cells at 100 nM for 30 min at room temperature. FRET was measured in the HeLa cells, and a 25% FRET decrease was measured in response to Src activation. The HeLa cells demonstrated membrane ruffling, characteristic of EGF-stimulated cells. A similar FRET decrease occurred in the NIH3T3 cells following administration of PDGF. In both HeLa cells and NIH3T3 cells, the Src inhibitor, PP 1, inhibited the FRET response, whereas the EGFR inhibitor, AG1478, had no significant effect.

Biochemical Analysis of the Chimeric EGFR or Src Reporter Proteins Expressed in Mammalian Cells Reporters expressed in mammalian cells were analyzed by immunoprecipitation (IP), western blot analysis, or fluorescence of the purified protein. For IP and western blot analysis, the following procedure was used. Following exposure to the appropriate stimulant or chemical (EGF, PDGF, or inhibitor), transfected cells in 10 cm culture dishes were rinsed twice with ice cold HBSS (20 mM Hepes, pH 7.4, 2 gil D-glucose) and lysed with 1.5 ml lysis buffer (50 mM Tris, pH 7.4, 100 mM NaCl, 1 mM EDTA, 0.1% TRITON X-100, 10 mM NaF, 2 mM sodium orthovanadate, 1 mM phenylmethylsulfonyl fluoride, 10 μg/ml pepstatin, 10 μg/ml leupeptin, and 10 μg/ml aprotinin). The suspensions were cleared by centrifugation, and the reporters were immunoprecipitated from the supernatant using a rabbit polyclonal anti-GFP antibody immobilized on protein G-Sepharose resin (Amersham). Western blot analysis was performed on samples run in 12% PAGE-SDS gels using a mouse monoclonal antiphosphotyrosine antibody (Upstate Biotechnology), a rabbit monoclonal anti-EGFR antibody (Calbiochem), or a mouse monoclonal anti-GFP antibody (Clontech) with secondary detection by anti-rabbit HRP or anti-mouse HRP.

For fluorescence analysis of purified reporters, the crude cell lysates were purified over a column of Ni-NTA agarose (Qiagen). The His$_6$ (SEQ ID NO:64) tagged reporters were eluted with 50 mM Tris pH 7.4/300 mM NaCl/100 mM imidazole and dialyzed into 50 mM Tris pH 7.4/50 mM NaCl/10 mM MgCl$_2$.

EXAMPLE 3

Identification of Chimeric Phosphorylation Indicators Using High Throughput Screening Based on the results described Examples 1 and 2, additional chimeric phosphorylation indicators can be developed and optimized, using a variety of fluorescent proteins, luminescent molecules, kinase or phosphatase substrates, PAABDs, and tetracysteine motifs. High throughput strategies are particularly useful for systematically generating and testing diverse libraries of such constructs (Zhao and Arnold, Curr. Opin. Chem. Biol. 3:284-290, 1997).

Initial high throughput diversity generation and screening are performed using the exemplified chimeric phosphorylation indicators (Examples 1 and 2), which are active in mammalian cells. Iterative cycles of variegation, for example (see U.S. Pat. No. 5,837,500), can confer additional useful features on these chimeric reporters. Diversity also can be created by a variety of other methods, including, for example, error prone PCR, oligonucleotide-directed mutagenesis with various degrees of bias towards wild-type codons (Cormack et al., Gene 173:33-38, 1996), DNA shuffling (Crameri et al., Nat. Biotechnol. 14:315-319, 1996; Minshull and Stemmer, Curr. Opin. Chem. Biol. 3:284-290, 1999), incorporation of random spacers, or "incremental truncation for the creation of hybrid enzymes" (Ostermeier et al., Nat. Biotechnol. 17:1205-1209, 1999).

High throughput screening can utilize a method such as fluorescence activated cell sorting (FACS), which can allow the identification of mutants or clones with the greatest brightness, highest expression levels under particular growth conditions, or unusual emissions spectra. FACS can be particularly useful for screening FRET constructs, in which the donor and acceptor are part of the same chimera, so that ratios of the two emissions reflect only FRET rather than variable expression levels. Chimeras having the most desirable characteristics then can be examined further to identify those that respond before and after application of a stimulus such as induction of kinase activity in a correlated way.

Although the chimeric phosphorylatable indicators can be screened in bacteria, yeast, or mammalian cells, the latter are preferred because, ultimately, the indicators are most useful for studies. of mammalian cells. Standard cultured lines such as HeLa, CHO, HEK-293, 3T3, or Jurkat are the cells of choice for the initial screening studies, although other cells, including cardiomyocytes, B cells, and the like can be used for confirmatory studies. For studies in mammalian cell lines, it is preferred that any individual cell pick up only a single chimeric sequence because the presence of fluorescent but nonresponsive proteins would fatally dilute and obscure the response of the good construct. Transfection methods such as electroporation or lipofection allow many different DNA molecules to enter each permeabilized cell and, therefore, are suitable only for screens in which nonfunctional sequences do not interfere. In comparison, a method such as retroviral infection can allow for insertion of a single chimera construct into the viral package. By working with a multiplicity of infection much less than 1, nearly all the transfectants will contain only a single introduced sequence. Cells that do not get infected will be nonfluorescent and noninterfering.

FACS can be used to discard nonfluorescent cells, and to deposit single fluorescent individuals into separate wells of microtiter plates. The cells then can be expanded so as to obtain a sufficient number of cells in each well, probably with ongoing antibiotic selection. The clones then can be read using a microplate fluorometer, before and after appropriately stimulating the cells, for example by pharmacologically activating an endogenous or coexpressed kinase or phosphatase. Alternatively, the cells can be lysed and the fluorescence read before and after adding a separately expressed and purified enzyme. DNA recovered from the wells showing the best response then can be sequenced and re-expressed.

A microscopy-based method also can be used. For example, a relatively large numbers of cells can be plated into each well of several microtiter plates and, after the cells have attached and physiologically equilibrated to the culture, a reagent can be added to stimulate the cells, which are then be re-imaged and compared to the prestimulus views. Appropriate software can highlight those cells having the greatest response to the stimulus, and a DNA sample can be obtained from the cells using a micropipet. The advantages of this strategy are that that it avoids the low survival-rate and long duration associated with growing clones from single isolated cells, and that much more diverse libraries can be examined, with hundreds to thousands of cells per well.

At least two versions of planar microfluidic cell sorting have been proposed, one using cells pumped single file by electroosmotically driven flow through a T junction molded into silicone elastomer (Fu et al., Nat. Biotechnol. 17:1109-1111, 1999), and the other using arrays of cells individually releasable by microbubble formation. These methods work with nonadherent cells and, in principle, can be used to recover live cells, not just DNA samples.

EXAMPLE 4

Design and Characterization of CKAR

Figure 7C:
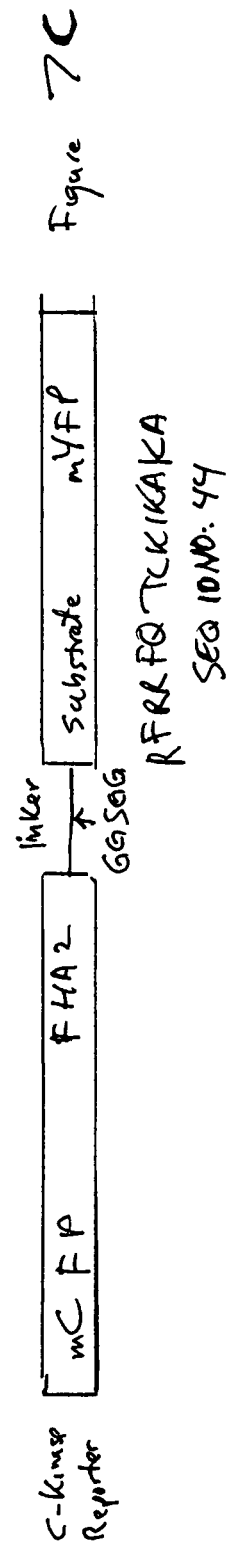

A reporter for PKC-mediated phosphorylation (C Kinase Activity Reporter, CKAR) was constructed analogously to a previously described reporter ("AKAR") for protein kinase A (Zhang et al., 2001). A schematic diagram of a CKAR is shown in FIG. 7C. As illustrated in this example, a CKAR may be composed of monomeric CFP (mCFP) and YFP (mYFP) (Zacharias et al., 2002) flanking a PKC substrate sequence tethered by a flexible linker to an FHA2 phosphothreonine binding domain from the yeast checkpoint protein rad53p (Durocher et al., 2002) (FIG. 8A). Phosphorylation of the PKC substrate sequence triggers an intramolecular clamp with the FHA2 module, causing a conformational change that alters the amount of fluorescence resonance energy transfer (FRET) from CFP to YFP (FIG. 8A). This change in FRET provides a continuous nondestructive fluorimetric readout for CKAR phosphorylation.

In designing CKAR, we focused on finding both an appropriate phosphopeptide binding domain and a specific substrate sequence. We switched from the 14-3-3τ phosphoserine-binding domain used in AKAR (Zhang et al., 2001) to FHA2 (SEQ ID NO: 57) for two reasons. 14-3-3τ is an obligate dimer, whereas FHA2 (SEQ ID NO: 57) is monomeric. Also, AKAR was not as good a substrate for phosphatases in living cells as FHA2 (SEQ ID NO: 57) or FHAI (SEQ ID NO: 56), perhaps because 14-3-3τ binds phosphoserine tightly and protects it from phosphatases, whereas AKAR analogs with FHAI (SEQ ID NO: 56) could be rapidly dephosphorylated upon cessation of PKA activity. The dissociation constants of FHA1 (SEQ ID NO: 56) and FHA2 (SEQ ID NO: 57) for their respective optimal peptides are 530 nM and 10 JLM (Durocher et al., 2002), whereas 14-3-3 binds its optimal peptide with a dissociation constant of 56 oM (Yaffe et al., 1997). The modestaffinity of FHA2 (SEQ ID NO: 57) for phosphothreonine makes CKAR reversible and allows CKAR to monitor the ongoing balance between PKC and phosphatases. We designed a specific PKC substrate sequence that would also bind FHA2 (SEQ ID NO: 57). This sequence was designed de novo based on information from oriented peptide library screens that have determined optimal substrate sequences for all PKC isoforms (Nishikawa et al., 1997; Songyang et al., 1994). We designed the substrate sequence based on three criteria: 1) consensus phosphorylation sequence for PKC, 2) minimal susceptibility to other basophilic kinases (Yaffe et al. 2001), 3) determinants that favor FHA2 binding. We decided upon the sequence GGSG-GRFRRFOTLKIKAKAGGSGG (SEQ ID NO: 43), where the underlined region is the substrate sequence RFR-RFQTLKIKAKA (SEQ ID NO: 44), flanked by a flexible linker sequence GGSGG (SEQ ID NO: 45). This sequence is predicted to be an excellent substrate for all PKC isoforms, but suboptimal for all other kinases (Nishikawa et al., 1997; Yaffe et al. 2001).

Figure 8:
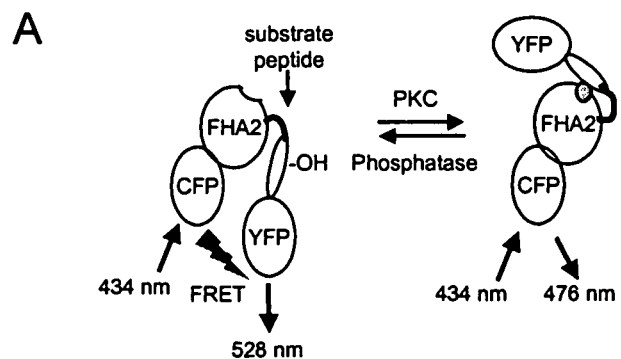
FIG. 8A illustrates the generation of C Kinase Activity Reporter (CKAR), comprised of mCFP, the FHA2 domain of Rad53p, a PKC substrate sequence, and mYFP.
FIG. 8B illustrates the stoichiometrically phosphorylation of CKAR by PKC in vitro. Inset: Coomassie-stained purified CKAR (top) and $^{32}p$ autoradiography (bottom).
FIG. 8C shows emission spectra of CKAR incubated for 30 min at 30° C. with and without purified PKCβII.
FIG. 8D illustrates that incubation of CKAR with active Calmodulin-dependent kinase II (CaMKII) or cAMP-dependent kinase (PKA) resulted in no change in FRET.
Figure 8:
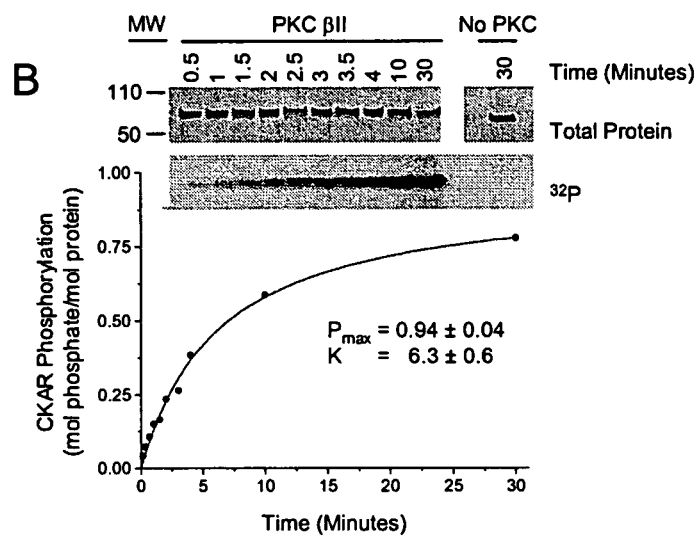
Figure 8:
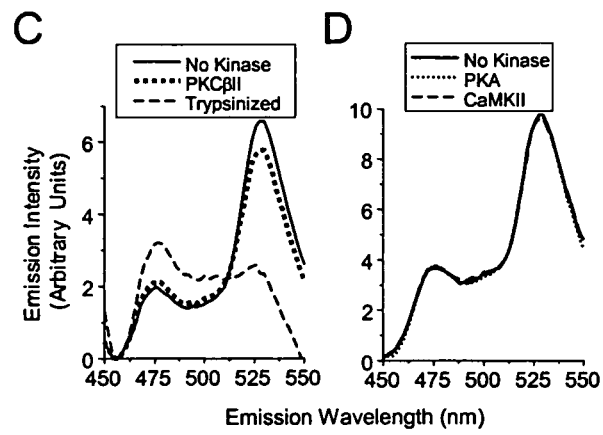

FIG. 8: Generation of C Kinase Activity Reporter (CKAR). 8A: CKAR is comprised of mCFP, the FHA2 domain of Rad53p, a PKC substrate sequence, and mYFP. The substrate sequence, when phosphorylated, binds the FHA2 phosphopeptide binding domain. This conformational change results in a change in fluorescence resonance energy transfer (FRET), reversible by phosphatases (PP). 8B: CKAR is stoichiometrically phosphorylated by PKC in vitro. Time-course of $^{32}$p incorporation into nickel-purified histidine-tagged CKAR measured by scintillation counts of excised coomassie-stained bands. Inset: Coomassie-stained purified CKAR (top) and $^{32}$p autoradiography (bottom). 8C: Emission spectra of CKAR incubated for 30 min at 30° C. with and without purified PKCβII. Excitation at 434 nm resulted in a CFP emission peak (476 nm) and YFP emission peak caused by FRET from CFP (528 nm). PKC phosphorylation resulted in decreased intensity at 528 nm and increased intensity at 476 nm, consistent with a decrease in FRET. Incubation of CKAR with trypsin for 30 min at 30° C. destroyed the YFP emission, demonstrating that FRET was caused by intramolecular energy transfer. 8D: Incubation with active Calmodulin-dependent kinase II (CaMKII) or cAMP-dependent kinase (PKA) resulted in no change in FRET.

CKAR expressed in bacterial cells as a 6×His-tagged fusion construct was purified and tested for substrate specificity in vitro. FIG. 8B shows that CKAR was stoichiometrically phosphorylated by PKC in a standard phosphorylation assay using recombinant PKC βII. In contrast, CKAR was not phosphorylated by either CaMKII or PKA using standard assays for these two kinases (data not shown), even though these two kinases are predicted to be the most likely alternatives to phosphorylate the CKAR (Yaffe et al., 2001).

Emission spectra of CKAR at the CFP excitation maximum (434 nm) before and after phosphorylation by PKC (30 minutes) show a decrease of YFP emission (528 nm) and concomitant increase in CFP emission (476 nm) upon phosphorylation (FIG. 8C). Trypsinolysis of CKAR to cleave CFP from YFP resulted in a dramatic loss of YFP emission, confirming that the YFP emission peak in intact CKAR is caused by intramolecular FRET (FIG. 8C, dashed (blue) line). In contrast, emission spectra of CKAR before and after incubation in phosphorylation reactions with active PKA and CaMKII showed no change (FIG. 8D). Thus, specific phosphorylation of CKAR by PKC results in a decrease in FRET. The absolute amounts of FRET can be estimated from FIG. 8C to be 38% before and 34% after phosphorylation, assuming that emission at 476 nm arises solely from the CFP donor and that FRET is negligible after trypsinolysis.

Construction of a C-Kinase Activity Reporter (CKAR)

CKAR was generated in the mammalian expression vector pcDNA3.1(+) (Invitrogen). CFP was amplified by Polymerase Chain Reaction (PCR) from a plasmid template to encode a HindIII restriction site followed by a consensus initiation site for translation (CGCCACC) (Kozak, 1987) prior to the initiating ATG of CFP, and a KpnI restriction site at the 3' end instead of a terminating codon. FHA2 was amplified by PCR to include KpnI and BamHI restriction sites at the 5' and 3' ends, respectively. Citrine, our preferred version of yellow fluorescent protein (Griesbeck et al., 2001), was amplified by PCR to include a 5' BamHI followed by the PKC substrate sequence and a 3' XbaI following the terminating codon. These pieces were cloned into pcDNA3.1 and confirmed by sequencing.

A parallel construct was made including the mutation A206K in both CFP (mCFP) and Citrine (mYFP) to reduce the intrinsic homoaffinity of all GFP's (Zacharias et al., 2002) and preclude intermolecular FRET by CFP-mYFP dimerization. This construct was shown to function as well as the original CKAR, and so was used for all experiments. For in vitro experiments, CKAR was amplified to include a 5' BglII site and a 3' SalI site, and cloned into pRSET$_B$ (Invitrogen) cut from BamHI to XhoI. MyrPalm-CKAR was generated by the addition of a HindIII restriction site, a consensus translational initiation site, and the 5' 30 bp of Lyn kinase to the 5' end of CKAR. This sequence encodes for myristoylation and palmitoylation, previously shown to be sufficient to target a protein to the plasma membrane (Zacharias et al., 2002).

Construction of other Plasmids

MyrPalm-CFP was made by PCR with the same 5' primer as used for MyrPalm-CKAR and a 3' primer to the C-terminus of CFP with an Xba site, and cloned into pcDNA3.1(+). YFP-PKCβII-YFP was made by PCR of mYFP from HindIII to KpnI, rat PKC☐II from KpnI to XhoI, and YFP from XhoI to XbaI, cloned sequentially into pcDNA3.1(+). CYPHR was generated by PCR of CFP from HindIII to KpnI, the PH domain of murine PLCγ1 (amino acids 10-140) from KpnI to XhoI, and mYFP from XhoI to XbaI, cloned sequentially into pcDNA3.1(+).DAGR was similarly created by PCR of the C1A and C1B domains of rat PKCβII (amino acids 37-152) from KpnI to XhoI and substitution for the PH domain in CYPHR.

Protein Expression, Kinase Assays, and In vitro Spectroscopy.

CKAR in the pRSET$_B$ vector was transformed into BL21 Gold *Escherichia coli* (Stratagene) and purified by nickel chelation chromatography as described previously (Miyawaki and Tsien, 2000). Protein yield was estimated by CFP absorption at 434 nm. Fluorescence emission spectra were measured with an excitation wavelength of 434 nm.

For kinase assays, CKAR (125 nmol) was incubated with purified PKC βII (1 U μL$^{-1}$), PKA (5 U μL$^{-1}$), or CamKII (5 U μL$^{-1}$) with appropriate buffers and cofactors including γ$^{32}$P-ATP (100 μM, 10 μCi) as described earlier for PKC (Newton, 2002a) or in manufacturers' instructions for PKA and CamKII (New England Biolabs) for varying amounts of time. Proteins were separated by SDS-PAGE, stained with Coomassie Blue, and bands corresponding to CKAR excised and $^{32}$P incorporation measured by scintillation counting. Fluorescence emission scans were obtained from samples phosphorylated in parallel with unradiolabeled ATP, with excitation at 434 nm to excite CFP.

Cell Culture

HeLa and Madin-Darby canine kidney (MDCK) cells were plated onto sterilized glass coverslips in 35 mm dishes and grown in DMEM containing 10% fetal bovine serum at 37° C. with 5% CO$_2$. At 60-80% confluency, cells were transfected with either Superfect or Polyfect (Qiagen) and allowed to grow for 12-24 hours post-transfection before imaging. For calcium imaging experiments, 0.2-1.0 μM fura Red/AM or fura-2/AM (Molecular Probes, Eugene, Oreg.) was loaded into cells for 30 min, washed once with PBS, and incubated for 30-60 minutes in fresh media before imaging.

Cell Imaging

Cells were washed once with Hank's balanced salt solution and imaged in the dark at room temperature. Images were acquired on a Zeiss Axiovert microscope with a cooled charge-coupled device camera (Photometrics, Tucson, Ariz.), controlled by MetaFluor 3.0 software (Universal Imaging, West Chester, Pa.). CFP, FRET, and Fura Red images were obtained through a 440DF20 excitation filter, a 455DRLP dichroic mirror, and three separate emission filters (480DF30 for CFP, 535DF25 for FRET, and 653DF95 for Fura Red). Citrine intensity was imaged through a 495DF10 excitation filter, 455DRLP dichroic mirror, and 535DF25 emission filter. Excitation and emission filters were switched in filter wheels (Lambda 10-2, Sutter Instruments, Inc., San Rafael, Calif.). Integration times were varied between 200 msec and 500 msec to optimize signal and minimize photobleaching. Optical filters were obtained from Chroma Technologies and Omega Optical (Brattleboro, Vt.). Because Fura Red emission overlaps Citrine/FRET emission, care was taken to limit the amount of Fura Red loaded. Measurements were restricted to cells in which CKAR expression was high enough to be unaffected by changes in Fura Red intensity.

EXAMPLE 5

CKAR Reports PKC Activity in Live Cells

We next explored whether CKAR could function as a reporter for PKC in live cells. FIG. 9A shows that CKAR expressed in MDCK cells showed a decrease in FRET upon activation of PKC with phorbol dibutyrate (PDBu). Note that the data in FIG. 9A are plotted as the ratio of cyan fluorescence (which increases as FRET decreases) to yellow emission (which decreases as FRET decreases). This decrease in FRET was rapidly reversed by the specific PKC inhibitor Gö6983. Treatment of MDCK cells with vehicle (DMSO) and then forskolin to activate PKA did not alter the FRET ratio, indicating that the sensor does not respond to PKA (FIG. 9B, red line). Similarly, no response was observed when cells were first treated with Go6983 to inhibit PKC and then treated with thapsigargin to stimulate CaMKII by calcium release (FIG. 9B, green line). These experiments performed in HeLa cells yielded the same results (data not shown). Thus, CKAR senses PKC but not PKA or CaMKII activation in live cells. We calibrated fluorescence intensity to protein concentration by imaging pure fluorescent protein of known concentration to obtain a standard curve (data not shown). Based on this calibration, we estimate CKAR concentration in cells to be 0.5 to 2 μM except where otherwise specified. This is well within the range of concentration of endogenous PKC substrates, which can be as high as 20 μM for abundant proteins such as MARCKS (Wang et al., 2002).

Figure 9:
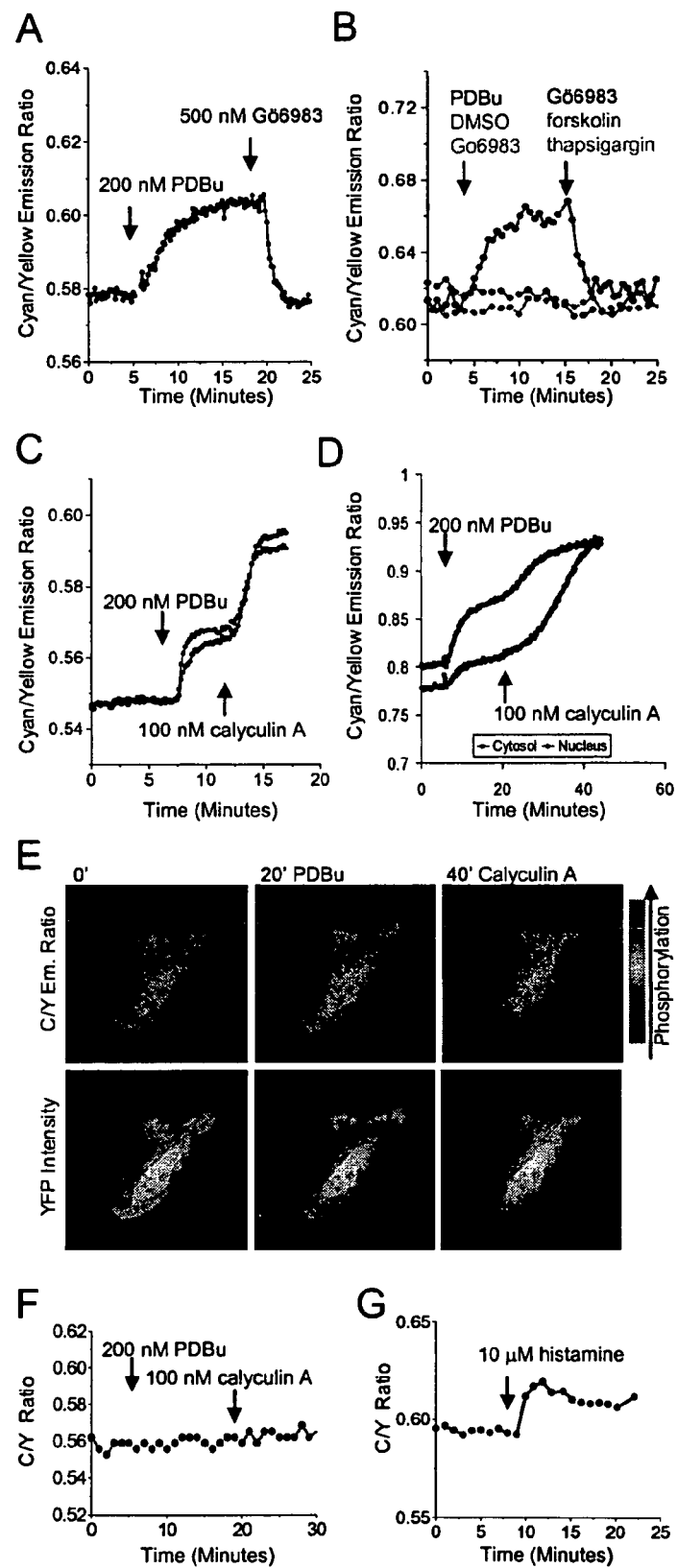
FIG. 9A illustrates that CKAR expressed in HeLa cells is phosphorylated upon stimulation of PKC with 200 nM PDBu. This is reversed by addition of 500 nM Go6983, a specific inhibitor of PKC.
FIG. 9B illustrates that CKAR phosphorylation is specific for PKC (Upper trace): PKC is activated by 200 nM PDBu and inhibited by 1 µM Go6983. Middle trace: Neither DMSO (vehicle for PDBu) nor 10 µM forskolin cause a change in FRET. Bottom trace: Pre-inhibition of PKC (1 µM Go6983) does not change basal FRET, which remains unchanged by release of intracellular calcium by thapsigargin to stimulate other calcium-sensitive kinases such as CaMKII.
FIG. 9C shows that supramaximal stimulation of PKC with 200 nM PDBu results in stable phosphorylation of CKAR, but inhibition of phosphatases with 100 nM calyculin A results in additional phosphorylation.
FIG. 9D shows that phosphorylation of CKAR in the cytosol (upper trace) and nucleus (lower trace) reveal preferential cytosolic phosphorylation after PDBu but greater and uniform phosphorylation after calyculin A treatment.
FIG. 9E shows images corresponding to FIG. 9D show phosphorylation (red-shift of pseudocolored FRET Ratio image, top) of CKAR after PDBu (20') and PDBu and calyculin (40'). YFP intensity images (bottom) indicate no change in CKAR localization over the course of the experiment.
FIG. 9F illustrates that mutation of the threonine phosphoacceptor in the designed PKC substrate of CKAR precludes FRET changes in response to either 200 nM PDBu or 250 nM calyculin.
FIG. 9G shows that 10 µM histamine resulted in rapid phosphorylation of CKAR in HeLa cells, indicating that CKAR is also sensitive to receptor-mediated activation of PKC.

FIG. 9: CKAR is a specific, reversible reporter for PKC activation in live cells. 9A: CKAR expressed in HeLa cells is phosphorylated upon stimulation of PKC with 200 nM PDBu. This is reversed by addition of 500 nM Go6983, a specific inhibitor of PKC. 9B: CKAR phosphorylation is specific for PKC. Black: PKC is activated by 200 nM PDBu and inhibited by 1 μM Go6983. Red: Neither DMSO (vehicle for PDBu) nor 10 μM forskolin cause a change in FRET. Green: Pre-inhibition of PKC (1 μM Go6983) does not change basal FRET, which remains unchanged by release of intracellular calcium by thapsigargin to stimulate other calcium-sensitive kinases such as CaMKII. All data are representative of at least 3 experiments.

We next tested whether full activation of PKC results in complete phosphorylation of CKAR or if cellular phosphatases counteract PKC activity to maintain a significant pool of unphosphorylated substrate. To maximally activate PKC, we treated MDCK cells with 200 nM phorbol esters. This resulted in a robust change in FRET (FIG. 9C; red and black lines are from two separate cells). Surprisingly, addition of the phosphatase inhibitor calyculin A (100 nM) to cells already treated with 200 nM PDBu resulted in an even larger increase in phosphorylation, indicating that maximal PKC activation does not saturate CKAR unless phosphatases are also inhibited. This phosphorylation is compartmentalized: PDBu results in preferential phosphorylation of CKAR in the cytosol over the nucleus, the further increase in phosphorylation after calyculin A results in uniform phosphorylation throughout the cell (FIG. 9D). Pseudocolor images of this FRET change are shown in FIG. 9E. Importantly, similar results were observed with CKAR expression ranging from 0.8 to 8 μM (data not shown), indicating that substrate buffering of PKC activity does not greatly alter CKAR responses at the concentrations used in this work. 9C: Supramaximal stimulation of PKC with 200 nM PDBu results in stable phosphorylation of CKAR, but inhibition of phosphatases with 100 nM calyculin A results in additional phosphorylation. Data are from two cells in the same field of view. 9D: Phosphorylation of CKAR in the cytosol (red) and nucleus (black) reveal preferential cytosolic phosphorylation after PDBu but greater and uniform phosphorylation after calyculin A treatment. 9E: Images corresponding to FIG. 9D show phosphorylation (red-shift of pseudocolored FRET Ratio image, top) of CKAR after PDBu (20') and PDBu and calyculin (40'). YFP intensity images (bottom) indicate no change in CKAR localization over the course of the experiment. 9F: Mutation of the threonine phosphoacceptor in the designed PKC substrate of CKAR precludes FRET changes in response to either 200 nM PDBu or 250 nM calyculin. 9G: CKAR is also sensitive to receptor-mediated activation of PKC. 10 μM histamine resulted in rapid phosphorylation of CKAR in HeLa cells.

To confirm that changes in FRET result from phosphorylation of CKAR at the intended amino acid, we changed the phosphoacceptor threonine in the PKC substrate sequence to alanine. FIG. 9F shows that this variant does not respond to either PDBu or calyculin A, consistent with the designed site of phosphorylation.

We next explored whether CKAR was sensitive enough to respond to physiological activation of PKC. FIG. 9G shows that histamine treatment of HeLa cells resulted in a small but reproducible change in FRET.

EXAMPLE 6

Membrane-tethered CKAR Detects Oscillations in Substrate Phosphorylation

We reasoned that because PKC activity is highest at membranes, a membrane-targeted CKAR would be a better substrate for PKC in intact cells. Thus we fused the 10 amino-terminal residues of Lyn kinase to CKAR. This sequence contains signals for myristoylation and palmitoylation (Zacharias et al., 2002), effectively targeting CKAR to the plasma membrane (FIG. 10A). FIG. 10B reveals that this myristoylated and palmitoylated CKAR (MyrPalm-CKAR) undergoes a FRET change upon treatment of HeLa cells with PDBu similar to that observed for cytosolic CKAR. However, unlike cytosolic CKAR, the PDBu-induced FRET change of the membrane-tethered CKAR was only modestly sensitive to calyculin A (FIG. 10B; compare to FIG. 9C). Thus, tethering CKAR at the site of action of PKC alters the phosphorylation/dephosphorylation equilibrium to favor phosphorylation.

We next examined the effect of receptor-mediated activation of PKC on membrane-tethered CKAR. FIG. 10C shows that in some cells, histamine stimulation of HeLa cells triggered a sustained series of transient phosphorylations. These were terminated after 20 minutes by inhibition of PKC with 1 μM Gö6983. Each phosphorylation "spike" displayed a rapid rise followed by a slower decline (FIG. 10D, expanded time scale of FIG. 10C), consistent with a burst of kinase activity followed by dephosphorylation to a baseline equilibrium between kinase and phosphatase activities. Oscillations were extremely variable in amplitude, period, and duration, and the data shown are representative of sustained, regular oscillations seen in a minority of cells (5-10%). Either inhibition of PKC with 1 μM Gö6983 (FIG. 10E) or mutation of the phosphoacceptor threonine to alanine (FIG. 10F) prevented a FRET change upon stimulation with 10 μM histamine, consistent with accurate reporting of phosphorylation by Myr-Palm-CKAR.

Figure 10:
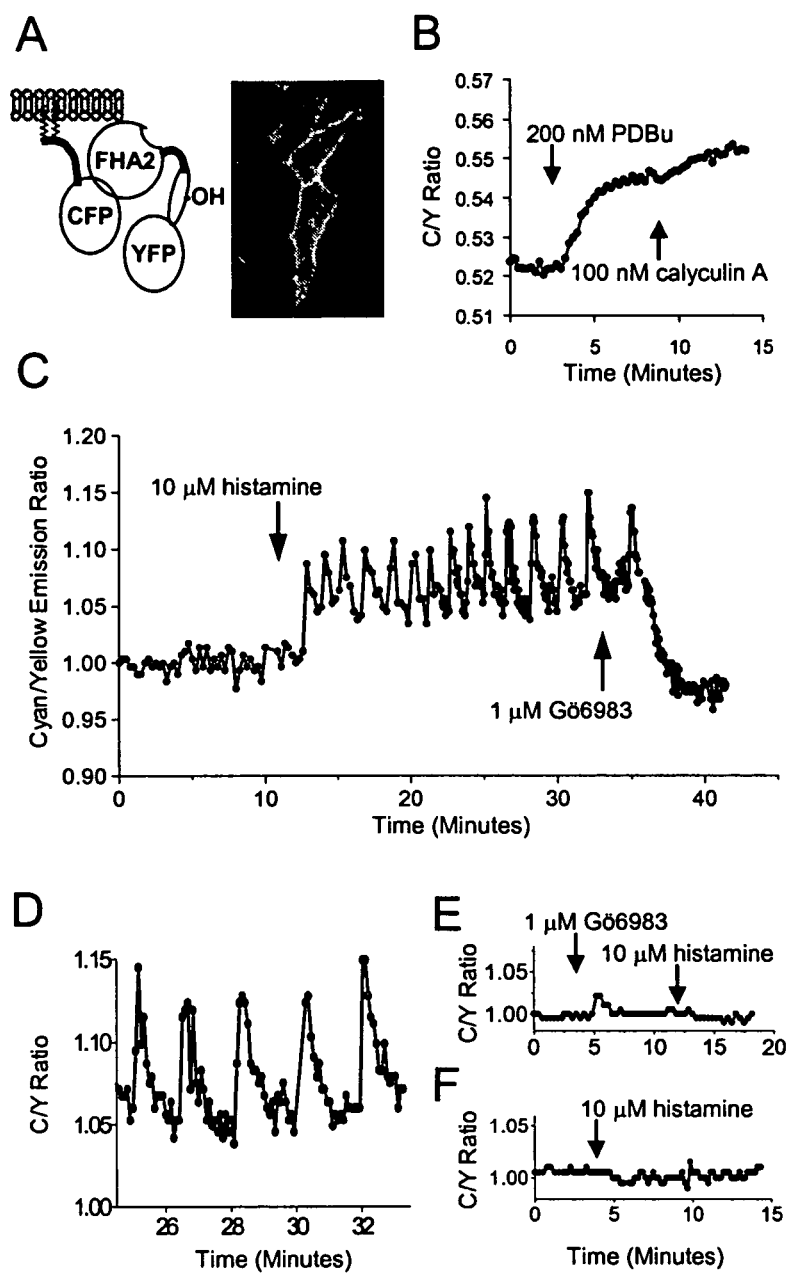
FIG. 10A illustrates targeting of CKAR to plasma membrane by fusion of the 10 amino acid amino-terminus of the kinase Lyn to the amino-terminus of CKAR, encoding myristoylation and palmitoylation. Inset is an image of MyrPalm-CKAR expressed in HeLa cells showing effective targeting of CKAR to the plasma membrane.
FIG. 10B illustrates supramaximal stimulation of PKC with 200 nM PDBu, which results in nearly complete phosphorylation of CKAR, as inhibition of phosphatases with 100 nM calyculin A results in only slight additional phosphorylation.
FIG. 10C shows oscillation of MyrPalm-CKAR phosphorylation after 10 µM histamine, and that this oscillatio is inhibited by 1 µM Gö6983.
FIG. 10D shows the data of FIG. 10C at an expanded time-scale.
FIG. 10E illustrates that pretreatment with 1 µM Gö6983 prevents MyrPalm-CKAR phosphorylation by 10 µM histamine.
FIG. 10F shows that mutation of the threonine phosphoacceptor to alanine (T413A) makes MyrPalm-CKAR unresponsive to 10 µM histamine.

FIG. 10: Targeting CKAR to plasma membrane. 10A: CKAR was targeted to plasma membrane by fusion of the 10 amino acid amino-terminus of the kinase Lyn to the amino-terminus of CKAR, encoding myristoylation and palmitoylation. Inset is an image of MyrPalm-CKAR expressed in HeLa cells showing effective targeting of CKAR to the plasma membrane. 10B: Supramaximal stimulation of PKC with 200 nM PDBu results in nearly complete phosphorylation of CKAR, as inhibition of phosphatases with 100 nM calyculin A results in only slight additional phosphorylation. 10C: MyrPalm-CKAR phosphorylation oscillates after 10 μM histamine, and is inhibited by 1 μM Gö6983. 10D: Expanded time-scale of FIG. 10C. 10E: Pretreatment with 1 μM Gö6983 prevents MyrPalm-CKAR phosphorylation by 10 μM histamine. 10F: Mutation of the threonine phosphoacceptor to alanine (T413A) makes MyrPalm-CKAR unresponsive to 10 μM histamine. All data are representative of at least 3 experiments. Oscillatory phosphorylation, while highly variable, was detected in 10-20% of cells studied, observed in over 30 cells in more than 12 different experiments.

The striking rhythmicity of histamine-induced oscillations in substrate phosphorylation led us to explore whether they reflected the well-characterized histamine-evoked calcium oscillations in HeLa cells. We measured histamine-evoked phosphorylation and $Ca^{2+}$ changes simultaneously with Myr-Palm-CKAR and the $Ca^{2+}$ indicator Fura Red. FIG. 11A shows that the oscillations in CKAR phosphorylation (black line) are phase-locked with $Ca^{2+}$ oscillations (red line). Quantitative analysis of the peaks reveals that phosphorylation lags approximately 10-15 sec behind $Ca^{2+}$ elevations (FIG. 11B). To eliminate the possibility of spectral overlap from Fura Red causing illusory FRET changes in these experiments, we measured histamine-induced calcium spikes with Fura Red in cells expressing the Thr to Ala mutant MyrPalm-CKAR, and saw almost no overlap of Fura Red signal into the cyan and yellow emission channels (FIG. 11C). Although oscillations are highly variable in HeLa cells, we noted that MyrPalm-CKAR phosphorylation was always coupled to $Ca^{2+}$ (examined in at least 15 cells from 8 separate experiments), whether the $Ca^{2+}$ increases were regular, sustained oscillations or brief, irregular transients.

In contrast to the oscillatory phosphorylation response of membrane-tethered MyrPalm-CKAR, the data in FIG. 9F showed that response of cytosolic CKAR is not oscillatory. To confirm this result, we simultaneously measured CKAR phosphorylation and $Ca^{2+}$ oscillations within the same cell. FIG. 11D shows that calcium-controlled oscillatory PKC phosphorylation does not propagate through the cytosol (FIG. 11D). Thus the balance between PKC and phosphatases oscillates only at the membrane, where PKC is most active.

Figure 11:
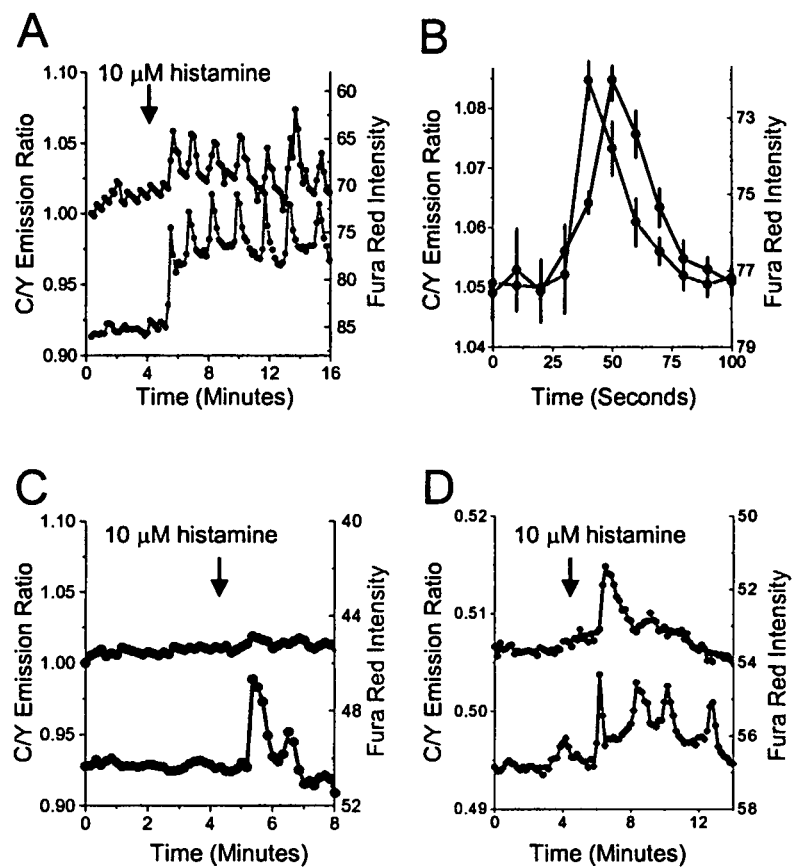
FIG. 11A illustrates that MyrPalm-CKAR oscillatory phosphorylation corresponds directly to calcium oscillations, showing calcium (Fura Red intensity, RED) and MyrPalm-CKAR phosphorylation (CFP-YFP FRET, BLACK) measurements.
FIG. 11B ilustrates the results of averaging the calcium and phosphorylation peaks shown in FIG. 11A.
FIG. 11C illustrates FRET changes in HeLa cells expressing MyrPalm-CKAR T413A after histamine stimulation.
FIG. 11D shows that histamine stimulation resulting in calcium oscillations does not result in oscillatory phosphorylation of cytosolic CKAR.

FIG. 11: MyrPalm-CKAR oscillatory phosphorylation corresponds to calcium oscillations. FIG. 11A Calcium (Fura Red intensity, red) and MyrPalm-CKAR phosphorylation (CFP-YFP FRET, black) show that MyrPalm-CKAR phosphorylation corresponds directly to calcium transients.

FIG. 11B Averaging the calcium and phosphorylation peaks in FIG. 11A illustrates a consistent lag of 10-20 seconds in MyrPalm-CKAR phosphorylation after initiation of calcium transients. The time of each Fura Red intensity spike was normalized and the Fura Red intensities and FRET ratios averaged for each image acquisition surrounding that fixed time. FIG. 11C Histamine stimulation of HeLa cells expressing MyrPalm-CKAR T413A shows that FRET changes are almost entirely independent of spectral overlap from Fura Red signals and instead depend on the phosphoacceptor T413 in the PKC substrate of MyrPalm-CKAR. FIG. 11D: Histamine stimulation resulting in calcium oscillations does not result in oscillatory phosphorylation of cytosolic CKAR. All data are representative of at least 3 experiments. Phase-locked calcium and phosphorylation oscillations have been noted in 15 different cells from 8 experiments.

EXAMPLE 7

Correlation of Activity with Translocation

The preceding results show phase-locked oscillations of PKC activity and calcium release. We next addressed whether this $Ca^{2+}$-controlled activity reflected $Ca^{2+}$-controlled membrane association or whether it reflected $Ca^{2+}$-controlled changes in membrane affinity independent of dissociation of PKC from the membrane. (Nalefski and Newton, 2001; Oancea and Meyer, 1998). To measure translocation in HeLa cells, we developed a novel FRET assay that does not require complex optics such as total internal reflection fluorescence (Codazzi et al., 2001) or subjective discrimination of "membrane" and "cytosol" regions in acquired images (Oancea and Meyer, 1998). We fused the amino-terminus of Lyn kinase to mCFP to encode for myristoylation and palmitoylation (Myr-Palm-mCFP), and coexpressed this with a PKC that had mYFP fused at both amino- and carboxy-terminii (FIG. 12A). When PKC translocates from the cytosol to the membrane upon generation of calcium and DAG, the average distance between CFP and YFP decreases, causing increased FRET. YFP was fused to both ends of PKC to increase the probability of FRET upon PKC translocation. This method allows for whole cell monitoring of PKC translocation to the site of MyrPalm-CFP. FIG. 12B shows that histamine stimulation of HeLa cells results in repetitive transient translocations (black line) that are phase-locked with calcium oscillations imaged with the fluorescent dye Fura Red (red line), consistent with a visible redistribution of mYFP-tagged PKC to membrane (data not shown). Oscillatory translocation was observed in the absence of Fura Red, indicating that FRET and not spectral overlap from Fura Red is responsible for the increase in measured yellow to cyan emission ratio (data not shown).

Figure 12:
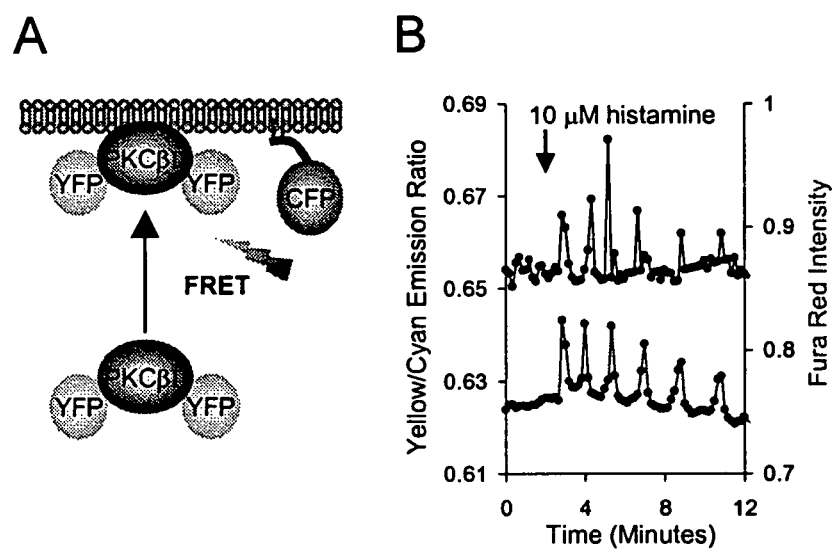
FIG. 12A illustrates how YFP fused to both termini of PKC functions as a FRET acceptor for CFP fused to the myristoylation and palmitoylation sequence from Lyn (MyrPalm-CFP).
FIG. 12B illustrates that the addition of 10 µM histamine to HeLa cells causes rapid, oscillating translocation of YFP-PKC-YFP to plasma membrane (BLACK) corresponding to oscillating calcium transients imaged by Fura-Red in the same cell (RED).

FIG. 12. Histamine induces oscillations of PKC translocation. FIG. 12A: YFP fused to both termini of PKC functions as a FRET acceptor for CFP fused to the myristoylation and palmitoylation sequence from Lyn (MyrPalm-CFP). Translocation of YFP-PKC-YFP to a membrane containing Myr-Palm-CFP results in increased FRET. FIG. 12B: Addition of 10 µM histamine to HeLa cells causes rapid, oscillating translocation of YFP-PKC-YFP to plasma membrane (black) corresponding to oscillating calcium transients imaged by Fura Red in the same cell (red). Data are representative of 3 experiments.

$Ca^{2+}$ Oscillations are Uncoupled from Diacylglycerol Production

To explore whether DAG oscillates in phase with calcium, we designed a probe for PLC activity. The most direct readout for DAG is translocation of the DAG-binding C1 domain (Oancea and Meyer, 1998). Unfortunately, GFP-tagged C1 domains from PKC β, γ or δ are insoluble in HeLa cells, and do not translocate effectively (data not shown). Instead, we took advantage of methodologies to detect $IP_3$ as a measure of PLC activity. As shown previously (Hirose et al., 1999; van der Wal et al., 2001), the PH domain of PLCδ, which binds $PIP_2$, translocates from the membrane to the cytosol upon PLC activation and cleavage of $PIP_2$. We adopted a novel strategy to measure translocation of this PH domain that reports translocation from membrane to cytosol upon PLC activation. Fusion of both CFP and YFP to the PH domain of PLCδ (which we call CYPHR, for Cyan/Yellow PH domain Reporter) allows us to measure both intramolecular and intermolecular FRET.

Figure 13:
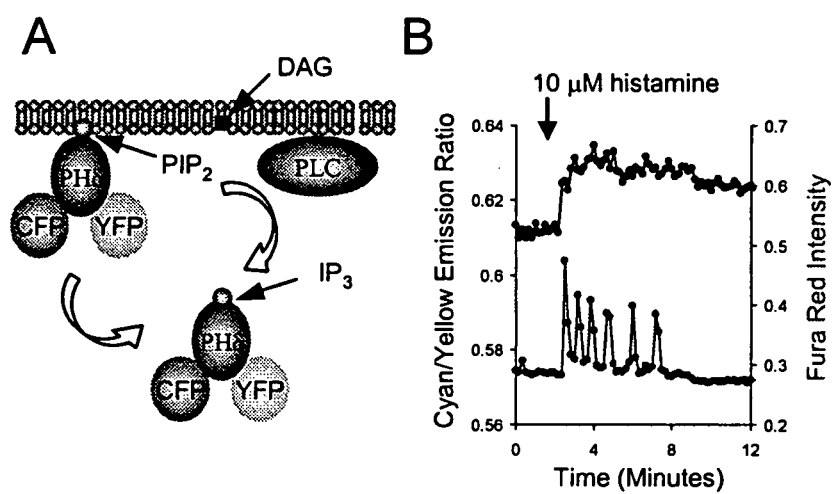
FIG. 13A illustrates the ability of CYPHR, a CFP-PHδ-YFP fusion construct to report PLC activity by reduced intermolecular FRET upon translocation from membrane.
FIG. 13B illustrates that CYPHR reports constant PLC activity (BLACK) during calcium oscillations (RED).

FIG. 13. Translocation of the PH domain of PLCδ reported by FRET reveals oscillations of PLC activity. FIG. 13A: CYPHR, a CFP-PHδ-YFP fusion construct reports PLC activity by reduced intermolecular FRET upon translocation from membrane. The PH domain of PLCδ1 which binds $PIP_2$ in the plasma membrane, translocates to cytosol upon $PIP_2$ hydrolysis. Translocation from membrane (2 dimensions) to cytosol (3 dimensions) results in a decreased effective concentration, and hence lower intermolecular FRET. FIG. 13B: CYPHR reports constant PLC activity (black) during calcium oscillations (red). Data are representative of 4 experiments.

Whereas changes in intramolecular FRET are unpredictable, intermolecular FRET depends on the concentration of fluorophore: because the effective concentration of fluorophore is lower when diffusing in 3-dimensional cytosol than when diffusing in a 2-dimensional membrane, the dilution experienced by the PH domain upon PLC activation is reported as a decrease in FRET (FIG. 13A). Decreased FRET corresponded to visible translocation from membrane to cytosol (data not shown).

CYPHR expressed in HeLa cells reports a sustained PLC activity during histamine-evoked calcium oscillations (FIG. 13B), implying a CICR mechanism of oscillation instead of dynamic uncoupling. This is consistent with earlier reports of the insensitivity of histamine-evoked calcium oscillations in HeLa cells to $IP_3$ concentration (Sauve et al., 1991) and contrasts with systems showing phase-locked oscillations of $IP_3$ and calcium (Hirose et al., 1999; Nash et al., 2001). Indeed, a GFP-tagged PH domain exhibits oscillatory translocation in phase with ATP-evoked calcium oscillations in MDCK cells, an example of the dynamic uncoupling mechanism of oscillating PLC activity (Hirose et al., 1999).

Figure 14:
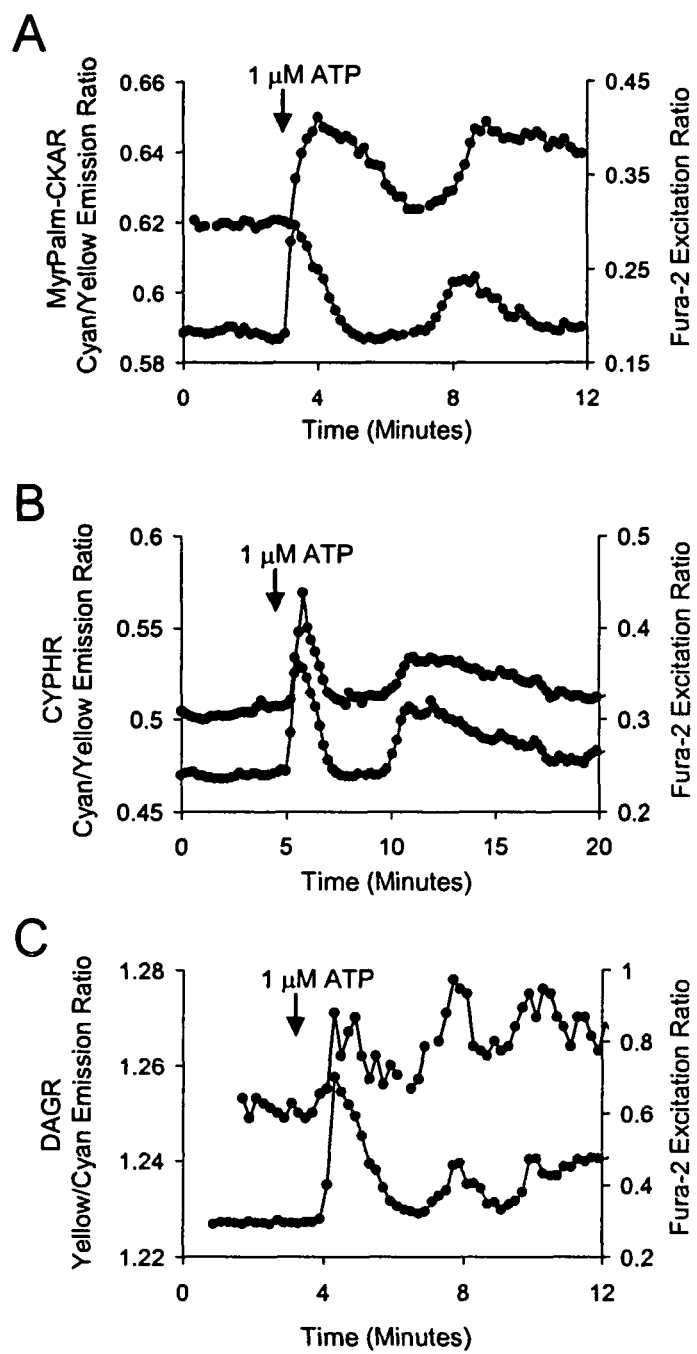
FIG. 14A illustrates that 10 µM ATP, used to induce calcium transients that are seen to be phase-locked with responses of MyrPalm-CKAR, may be used to show that phosphorylation via Phospholipase C and oscillations of PKC activity in MDCK cells.
FIG. 14B illustrates that CYPHR may be used to report PLC activity in MDCK cells.
FIG. 14C illustrates that DAGR may be used to report DAG levels in MDCK cells.

FIG. 14. Phospholipase C controls oscillations of PKC activity in MDCK cells. 10 µM ATP induces calcium transients phase-locked with responses of FIG. 14A: MyrPalm-CKAR (reports phosphorylation), FIG. 14B: CYPHR (reports PLC activity), and FIG. 14C: DAGR (reports DAG). All data are representative of 3-5 experiments.

Consistent with these findings, MyrPalm-CKAR, DAGR (DAG reporter, identical to CYPHR but with a PKCβ C1 domain replacing the PH domain), and CYPHR report transient responses of phosphorylation, DAG and PLC activity phase-locked with calcium transients in MDCK cells (FIGS. 14A, B, and C). DAGR visibly translocated from cytosol to membrane upon ATP stimulation or PDBu addition to MDCK cells (data not shown) consistent with its characterization as a DAG sensor (Oancea et al., 1998) This differs markedly from histamine-evoked oscillations of phosphorylation in HeLa cells, in which PLC activity reported by CYPHR is independent of calcium transients. We conclude that histamine-evoked PKC responses in HeLa and ATP-evoked PKC responses in MDCK cell represent two distinct mechanisms for temporal control of PKC activation.

CKAR: A Specific Reporter Useful for Monitoring the Dynamic Interplay Between Phosphorylation and Dephosphorylation of PKC Substrates CKAR was successfully designed to be a specific, reversible reporter of phosphorylation by PKC (FIGS. 8 and 9). Specificity was achieved by de novo design of a substrate sequence using information from oriented peptide library screens identifying determinants that dictate kinase substrate specificity (Yaffe et al., 2001). Reversibility was achieved by choosing an FHA2 domain to bind phosphothreonine with modest affinity, 10 p.M (Durocher et al., 2002).

The use of CKAR, for example as demonstrated in the Examples above, shows that PKC-mediated phosphorylation signals depend on the spatiotemporal context of second messengers, kinase, substrate and phosphatase. As shown in the Examples, the phosphorylation state of the reporter CKAR reflects coincidence of the second messengers calcium and DAG that together activate PKC, so that the C-Kinase reporter CKAR may be used to monitor the phosphorylation state of cells or of a sample. Tight spatial coupling of kinase and phosphatase activities allows for highly dynamic phosphorylation: when CKAR is tethered to membranes, its phosphorylation is phase-locked with calcium oscillations in both HeLa and MDCK cells, independent of constant (HeLa) or oscillating (MDCK) DAG generation. This temporal fidelity of the PKC signal pathway, from second messenger to substrate phosphorylation, allows precise control of cellular regulation by creating high temporal bandwidth for PKC signals and is likely to be of critical importance to many cellular processes.

The foregoing results demonstrate that a genetically engineered reporter may be used for monitoring the activity of endogenous PKC. Thus, with a PKC reporter having features of the invention, such as a PKC reporter as used in the Examples, the presence and/or activity of a c-kinase in a cell or sample may be detected, measured, and monitored over time and under different conditions if desired. For example, with this PKC reporter, the inventors have shown that substrate phosphorylation is under the dynamic control of second messenger levels, which directly regulate the intrinsic activity of PKC, and cellular phosphatase activity, which rapidly terminates signaling by PKC. It has further been shown that in HeLa and MDCK cells, histamine and ATP trigger sustained oscillatory phosphorylation of membrane-tethered reporter and that these oscillations are phase-locked with $Ca^{2+}$ oscillations.

PKC Translocation, CYPHR, and DAGR

We also devised new FRET-based reporters for PKC translocation, $PIP_2$-to-$IP_3$ hydrolysis, and diacylglycerol. These reporters not only translocate to and from the plasma membrane but also alter the ratio of yellow to cyan emissions in response to the appropriate signals. These indicators may have significant value in flow cytometry, complex tissues, or high-throughput screening, where quantitative monitoring of translocation of a GFP-tagged C1 domain, PKC, or PH domain to the plasma membrane is difficult.

Subcellular Specificities of CKAR Phosphorylation

We found that CKAR is only partially phosphorylated in vivo when localized to the cytosol, even with maximal activation of PKC by phorbol esters (FIG. 9C). Presumably, this phosphorylation arises from diffusional collision of CKAR with PKC at the membrane, where it becomes phosphorylated, and then diffuses back into the cytosol. The lower level of phosphorylation seen in the nucleus (FIGS. 9D and 9E) indicates a different balance of kinase and phosphatase there, either through impaired accessibility to active PKC or higher nuclear phosphatase activity. This is consistent with nuclear exclusion noted for most PKC isoforms (Kajimoto et al., 2001; Shirai et al., 1998a). In contrast, targeting CKAR to the plasma membrane, the site of activation of PKC, results in nearly complete phosphorylation of the reporter as revealed by the minimal effect of phosphatase inhibition on the phosphorylation of membrane-tethered CKAR (FIG. 10B). This likely reflects the increased probability of phosphorylating a substrate co-localized with PKC. These data indicate a spatial gradient in the kinase/phosphatase balance, plasma membrane>cytosol>nucleus. Such radial gradients were predicted some time ago (Brown and Kholodenko, 1999) but were not observable until the advent of genetically encoded phosphorylation reporters. It is interesting in this regard that not only are there an abundance of kinases tethered to their substrates (Jaken and Parker, 2000), but also there are a growing number of scaffolds that tether both a phosphatase and a kinase in the same complex (Coghlan et al., 1995) Westphal et al., 1998).

Calcium Oscillations Dictate Substrate Phosphorylation by Conventional PKCs:

HeLa cells, like many electrically non-excitable cell types, undergo repetitive cycles of calcium release and reuptake upon stimulation with some agonists, resulting in periodic spikes of free intracellular calcium. Conventional isoforms of PKC can translocate in phase with these spikes, leading to an oscillatory translocation, ostensibly producing bursts of PKC activity (Oancea and Meyer, 1998; Tanimura et al., 2002). It was not known, however, if PKC-mediated substrate phosphorylation and phosphatase activity were kinetically competent to result in distinct spikes of phosphorylation during individual calcium oscillations. We find that when CKAR is targeted to plasma membrane by acylation (FIG. 10A-E), regular, pulsatile phosphorylation oscillations occur in phase with calcium oscillations (FIG. 11).

Oscillations in PKC activity that are phase-locked with calcium oscillations can occur either through a predominantly calcium-mediated activation of conventional PKC isozymes or through concurrent oscillations in DAG and calcium. While the first of these possibilities is consistent with any model of calcium oscillations, the second is inconsistent with "CICR" (calcium-induced calcium release) (Harootunian et al., 1991; Nash et al., 2001; Thomas et al., 1996), which postulates no feedback of calcium to PLC activity, and thus does not predict nor account for oscillations of DAG and $IP_3$. Instead, a model of concurrently oscillating calcium and DAG implies an oscillator mechanism in "dynamic uncoupling" of receptor occupation from PLC activity (Harootunian et al., 1991; Hirose et al., 1999). These distinct modes of calcium oscillation are proposed to constitute disparate signals transduced by the same PLC-mediated pathway (Nash et al., 2001).

Previous work has shown oscillatory conventional PKC translocation during both CICR (Oancea and Meyer, 1998) and dynamic uncoupling (Codazzi et al., 2001) mediated calcium oscillations, as evidenced by sustained and oscillating DAG, respectively. Though we are unable to measure DAG directly in HeLa cells, our results are consistent with a CICR mechanism of calcium oscillation as PLC activity does not oscillate (FIG. 13), in agreement with previous results (Sauve et al., 1991), and inconsistent with oscillations of DAG.

These results show oscillatory PKC translocation, consistent with a requirement for both calcium and DAG for maximal membrane binding (FIG. 12); active PKC at membranes at least partially translocates to cytosol upon calcium reuptake, as DAG alone cannot maintain full PKC membrane affinity. It is important to note that translocation does not directly reflect activation, as weakly membrane-bound PKC is not fully active (Johnson et al., 2000; Newton and Keranen, 1994; Orr and Newton, 1992). Thus, in contrast to previous work showing such calcium-controlled PKC activity, we now have a direct readout of PKC substrate phosphorylation. The revelation of oscillatory substrate phosphorylation indicates a high temporal fidelity for PKC signals: changes in PKC activation are rapidly transduced to substrate phosphorylation or dephosphorylation by a close coupling of PKC and phosphatases. This temporal specificity is evident only when CKAR is targeted to membranes, as a cytosolic CKAR does not experience oscillatory phosphorylation, even in the presence of calcium oscillations (FIG. 13D). This is most likely because PKC activity is membrane-limited, allowing for enhanced phosphorylation of a membrane-bound substrate; a cytosolic substrate must rely on diffusion to membrane-bound PKC to become phosphorylated. Only a tight spatial coupling of kinase, phosphatase, and substrate allows such remarkably high temporal fidelity of phosphorylation signals.

An intriguing corollary of this result is the possibility of temporal PKC isoform specificity. In both CICR and dynamic uncoupling, DAG is present when cytosolic calcium is elevated, so conventional PKC oscillations are independent of DAG. In contrast, novel PKC isoforms, unresponsive to calcium, may differentiate between sustained and oscillatory DAG. Thus novel PKC's are equipped to discriminate CICR from dynamic uncoupling. However, without the advantage of a calcium-enhanced "search" for DAG (Nalefski and Newton, 2001), it is unknown if novel PKC's respond fast enough to maintain temporal fidelity of DAG oscillations. It will be important to test each PKC isoform for oscillatory translocation in both CICR and dynamic uncoupling calcium oscillations to illuminate differences in the temporal signals of individual PKC isoforms.

It is widely accepted that the outcome of PKC activity depends on the amount and duration of activation, but the importance of oscillatory phosphorylation is unclear. Such oscillations may be a mechanism of encoding signal specificity, or they may be a necessary consequence of calcium oscillations, unrelated to effects downstream of PKC. However, calcium oscillations increase both the sensitivity and specificity of calcium signals (De Koninck and Schulman, 1998; Dolmetsch et al., 1998; Li et al., 1998), setting precedent for such temporal decoding by the cell. As tools and techniques become available to better identify and assay the phosphorylation of physiological substrates of PKC, it will be important to evaluate if the same is true of oscillatory phosphorylation.

All patents, patent applications and publications cited herein, including all peptide and nucleotide sequences included therein and including publications listed as GenBank Accession Nos., are hereby incorporated by reference herein in their entireties.

Although the invention has been described with reference to the above examples, it will be understood that modifications and variations are encompassed within the spirit and scope of the invention. Accordingly, the invention is limited only by the following claims.

What is claimed is:

1. A chimeric phosphorylation indicator comprising a first fluorescent protein, a phosphoaminoacid binding domain (PAABD) comprising the forkhead-associated (FHA)2 sequence set forth in SEQ ID NO: 57, a protein kinase C (PKC)-phosphorylatable domain, and a second fluorescent protein,
wherein the phosphorylatable domain is operably linked to the PAABD;
wherein the first fluorescent protein and the second fluorescent protein are in operable linkage through the phosphorylatable domain and the PAABD;
wherein the first fluorescent protein is different from the second fluorescent protein;
wherein at least one of said first or said second fluorescent protein comprises a non-oligomerizing fluorescent protein;
wherein the first fluorescent protein and the second fluorescent protein are selected from the group consisting of an Aequorea green fluorescent protein (GFP; SEQ ID NO: 2), a Discosoma red fluorescent protein (RFP; SEQ ID NO: 12), an enhanced GFP (EGFP; SEQ ID NO:4), an enhanced CFP (ECFP; SEQ ID NO:6), an ECFP(1-227) (amino acids 1 to 227 of SEQ ID NO:6), an EYFP-V68L/Q69K (SEQ ID NO: 10), an enhanced YFP (EYFP; SEQ ID NO:8), citrine (SEQ ID NO: 10 with Q69M), an I125R DsRed mutant (SEQ ID NO:12 with I125R) and a fluorescent protein (SEQ ID NO:2) having a mutation of an amino acid residue selected from A206K, L221K, F223R, or a combination thereof;
wherein the first fluorescent protein and the second fluorescent protein exhibit a detectable resonance energy transfer when the first fluorescent protein is excited; and
wherein the PKC-phosphorylatable domain and phosphoaminoacid binding domain emit weak or no fluorescent light.

2. The chimeric phosphorylation indicator of claim 1, wherein the PKC-phosphorylatable domain comprises an amino acid sequence selected from the group consisting of PKC-phosphorylatable amino acid sequences RFRRFQTLKIKAKA (SEQ ID NO:44), KKKKKRFSFKKSFKLSGFSFKKNLL (SEQ ID NO: 46), KKRFSFKKFKL (SEQ ID NO: 47), KRFSSKKSFKLSGFSFKKNKKEA (SEQ ID NO: 48), KRFSSKKSFKLSGFSFKKSKKEA (SEQ ID NO: 49), KKFSSKKPFKLSGFSFR (SEQ ID NO: 50), ETTSSFKKFFTHGTSFKKSKEDD (SEQ ID NO: 51), KLFSSSGLKKLSGKKQKGKRGGG (SEQ ID NO: 52), EGITPWASFKKMVTPKKRVRRPS (SEQ ID NO: 53), EGVSTWESFKRLVTPRKKSKSKL (SEQ ID NO: 54) and RTPS (SEQ ID NO: 55).

3. The chimeric phosphorylation indicator of claim 1, wherein the PKC-phosphorylatable domain comprises the amino acid sequence RFRRFQTLKIKAKA (SEQ ID NO:44).

4. The chimeric phosphorylation indicator of claim 1, wherein the PKC substrate phosphorylatable domain is adjacent a polypeptide linker.

5. The chimeric phosphorylation indicator of claim 4, wherein the polypeptide linker comprises the sequence GGSGG (SEQ ID NO: 45), GHGTGSTGSGSS (SEQ ID NO: 61), RMGSTSGSTKGQL (SEQ ID NO: 62), or RMGSTSGSGKPGSGEGSTKGQL (SEQ ID NO: 63).

6. The chimeric phosphorylation indicator of claim 1, comprising, in an orientation from the amino terminus to carboxy terminus, mCFP, a polypeptide linker, an FHA2 phosphoaminoacid binding domain (SEQ ID NO: 57), a PKC substrate phosphorylatable domain comprising (SEQ ID NO: 44) and having an amino end and a carboxy end, said PKC substrate phosphorylatable domain being flanked on both its amino end and its carboxy end by a polypeptide linker, and mYFP.

7. The chimeric phosphorylation indicator of claim 1, wherein at least one amino acid of the phosphorylatable domain is phosphorylated.

8. The chimeric phosphorylation indicator of claim 1, further comprising a cell compartmentalization domain.

9. The chimeric phosphorylation indicator of claim 8, wherein the cell compartmentalization domain is a membrane targeting domain.

10. The chimeric phosphorylation indicator of claim 9, wherein the membrane targeting domain comprises an amino acid sequence to which a lipid molecule may covalently bind.

11. A chimeric phosphorylation indicator comprising a luminescent molecule, a phosphoaminoacid binding domain (PAABD) comprising the forkhead-associated FHA2 sequence set forth in SEQ ID NO: 57, a protein kinase C (PKC)-phosphorylatable domain comprising the amino acid sequence RFRRFQTLKIKAKA (SEQ ID NO:44), and a non-oligomerizing fluorescent protein;
wherein the phosphorylatable domain is operably linked to the PAABD;
wherein the luminescent molecule and non-oligomerizing fluorescent protein are in operable linkage through the phosphorylatable domain and the PAABD;
wherein the non-oligomerizing fluorescent protein is selected from the group consisting of an Aequorea green fluorescent protein (GFP; SEQ ID NO:2), a Discosoma red fluorescent protein (RFP; SEQ ID NO: 12), an enhanced GFP (EGFP; SEQ ID NO:4), an enhanced CFP (ECFP; SEQ ID NO:6), an ECFP(1-227) (amino acids 1 to 227 of SEQ ID NO:6), an EYFP-V68L/Q69K (SEQ ID NO: 10), an enhanced YFP (EYFP; SEQ ID NO:8), citrine (SEQ ID NO: 10 with Q69M), an I125R DsRed mutant (SEQ ID NO:12 with I125R) and a fluorescent protein (SEQ ID NO:2) having a mutation of an amino acid residue selected from A206K, L221K, F223R, or a combination thereof; wherein the luminescent molecule and the fluorescent protein exhibit a detectable luminescent resonance energy transfer (LRET) when the luminescent molecule emits energy, and wherein the PKC-phosphorylatable domain and phosphoaminoacid binding domain emit weak or no fluorescent light.

12. A chimeric phosphorylation indicator comprising a first fluorescent protein, a phosphoaminoacid binding domain (PAABD), a protein kinase C (PKC)-phosphorylatable domain comprising the amino acid sequence RFRRFQTLKIKAKA (SEQ ID NO:44) and a second fluorescent protein; wherein the phosphorylatable domain is operably linked to the PAABD; wherein the first fluorescent protein and the second fluorescent protein are in operable linkage through the phosphorylatable domain and the PAABD; wherein the first fluorescent protein is different from the second fluorescent protein;
wherein at least one of said first or and said second fluorescent protein comprises a non-oligomerizing fluorescent protein;
wherein the first fluorescent protein and the second fluorescent protein are selected from the group consisting of an Aequorea green fluorescent protein (GFP; SEQ ID NO: 2), a Discosoma red fluorescent protein RFP; SEQ ID NO: 12), an enhanced GFP (EGFP; SEQ ID NO:4), an enhanced CFP (ECFP; SEQ ID NO:6), an ECFP(1-227) (amino acids 1 to 227 of SEQ ID NO:6), an EYFP-V68L/Q69K (SEQ ID NO: 10), an enhanced YFP (EYFP; SEQ ID NO:8), citrine (SEQ ID NO: 10 with Q69M), an I125R DsRed mutant (SEQ ID NO:12 with I125R) and a fluorescent protein (SEQ ID NO:2) having a mutation of an amino acid residue selected from A206K, L221K, F223R, or a combination thereof; wherein the first and the second fluorescent proteins exhibit a detectable resonance energy transfer when the first fluorescent protein is excited, and wherein the PKC-phosphorylatable domain and phosphoaminoacid binding domain emit weak or no fluorescent light.

13. The chimeric phosphorylation indicator of claim 4, wherein the polypeptide linker comprises a polypeptide having between 3 amino acid residues to 50 amino acid residues.

14. The chimeric phosphorylation indicator of claim 4, wherein the polypeptide linker comprises a polypeptide having between 4 amino acid residues to 30 amino acid residues.

15. The chimeric phosphorylation indicator of claim 4, wherein the polypeptide linker comprises a polypeptide having between 5 amino acid residues to 15 amino acid residues.

16. The chimeric phosphorylation indicator of claim 1, wherein the first fluorescent protein and the second fluorescent proteins are each selected from the group consisting of a GFP (SEQ ID NO: 2), an RFP (SEQ ID NO:12), a fluorescent protein having at least 95% sequence identity to the GFP set forth in SEQ ID NO:2 and a fluorescent protein having at leaset 95% sequence identity to the RFP set forth in SEQ ID NO:12.

17. The chimeric phosphorylation indicator of claim 11, wherein the fluorescent protein is selected from the group consisting of a GFP (SEQ ID NO: 2), an RFP (SEQ ID NO:12) and a fluorescent protein having at least 95% sequence identity to the GFP set forth in SEQ ID NO:2 and a fluorescent protein having at leaset 95% sequence identity to the RFP set forth in SEQ ID NO:12.

18. The chimeric phosphorylation indicator of claim 12, wherein the first and second fluorescent protein is selected from the group consisting of a GFP (SEQ ID NO: 2), an RFP (SEQ ID NO: 12) and a fluorescent protein acids having at least 95% sequence identity to a the GFP set forth in SEQ ID NO: 2 and a fluorescent protein having at least 95% sequence identity to the RFP set forth in SEQ ID NO: 12.

19. The chimeric phosphorylation indicator of claim 1, wherein the GFP (SEQ ID NO: 2) has a mutation of amino acid residue at A206, L221, F 223 or a combination thereof.

20. The chimeric phosphorylation indicator of claim 11, wherein the GFP (SEQ ID NO: 2) has a mutation of amino acid residue at A206, L221, F 223 or a combination thereof.

21. A chimeric phosphorylation indicator comprising a first fluorescent protein, a phosphoaminoacid binding domain (PAABD) comprising the forkhead-associated (FHA)2 sequence set forth in SEQ ID NO: 57, a protein kinase C (PKC)-phosphorylatable domain, and a second fluorescent protein, wherein the phosphorylatable domain is operably linked to the PAABD;

wherein the first fluorescent protein and the second fluorescent protein are in operable linkage through the phosphorylatable domain and the PAABD;

wherein the first fluorescent protein and the second fluorescent protein are different;

wherein at least one of said first or said second fluorescent protein comprises a non-oligomerizing fluorescent protein;

wherein the first fluorescent protein and second fluorescent protein are selected from the group consisting of an Aequorea green fluorescent protein (GFP; SEQ ID NO: 2) and a Discosoma red fluorescent protein (RFP; SEQ ID NO: 12), wherein the first fluorescent protein and the second fluorescent protein exhibit a detectable resonance energy transfer when the first fluorescent protein is excited; and wherein the PKC-phosphorylatable domain and phosphoaminoacid binding domain emit weak or no fluorescent light.

22. The chimeric phosphorylation indicator of claim 21, wherein the fluorescent protein comprising a contiguous sequence of at least 150 amino acids having at least 90% sequence identity to the GFP (SEQ ID NO:2) or the RFP (SEQ ID NO:12).

23. A chimeric phosphorylation indicator comprising a first fluorescent protein, a phosphoaminoacid binding domain (PAABD) comprising the forkhead-associated (FHA)2 sequence set forth in SEQ ID NO: 57, a protein kinase C (PKC)-phosphorylatable domain, and a second fluorescent protein, wherein the phosphorylatable domain is operably linked to the PAABD;

wherein the first fluorescent protein and the second fluorescent protein are in operable linkage through the phosphorylatable domain and the PAABD;

wherein the first fluorescent protein and the second fluorescent protein are different; wherein at least one of said first or said second fluorescent protein comprises a non-oligomerizing fluorescent protein;

wherein the first fluorescent protein and second fluorescent protein are each selected from the group consisting of an Aequorea green fluorescent protein (GFP; SEQ ID NO: 2) and a Discosoma red fluorescent protein (RFP; SEQ ID NO: 12), a fluorescent protein having at least 95% sequence identity to the GFP set forth in SEQ ID NO:2 and a fluorescent protein having at least 95% sequence identity to the RFP set forth in SEQ ID NO: 12, wherein the first protein and the second fluorescent protein exhibit a detectable resonance energy transfer when the first fluorescent protein is excited; and wherein the PKC-phosphorylatable domain and phosphoaminoacid binding domain emit weak or no fluorescent light.

\* \* \* \* \*